US007534560B2

(12) United States Patent
Lu et al.

(10) Patent No.: US 7,534,560 B2
(45) Date of Patent: May 19, 2009

(54) SIMPLE CATALYTIC DNA BIOSENSORS FOR IONS BASED ON COLOR CHANGES

(75) Inventors: Yi Lu, Champaign, IL (US); Juewen Liu, Urbana, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 68 days.

(21) Appl. No.: 10/144,679

(22) Filed: May 10, 2002

(65) Prior Publication Data
US 2003/0215810 A1 Nov. 20, 2003

(51) Int. Cl.
C12Q 1/68 (2006.01)
C07H 21/04 (2006.01)
C12M 3/00 (2006.01)
G01N 33/20 (2006.01)
G01N 33/50 (2006.01)

(52) U.S. Cl. .................. 435/6; 536/23.1; 536/24.5; 435/287.2; 436/74; 436/94

(58) Field of Classification Search .................. 435/6; 536/23.1, 24.31, 24.5
See application file for complete search history.

(56) References Cited

U.S. PATENT DOCUMENTS

| 4,703,017 | A | 10/1987 | Campbell et al. |
| 4,855,240 | A | 8/1989 | Rosenstein et al. |
| 5,459,040 | A | 10/1995 | Hammock et al. |
| 5,472,881 | A | 12/1995 | Beebe et al. |
| 5,580,967 | A | 12/1996 | Joyce |
| 5,593,835 | A | 1/1997 | Rando et al. |
| 5,631,148 | A | 5/1997 | Urdea |
| 5,663,064 | A | 9/1997 | Burke et al. |
| 5,807,718 | A | 9/1998 | Joyce et al. |
| 5,807,967 | A | 9/1998 | Snow et al. |
| 5,910,408 | A | 6/1999 | Szostak et al. |
| 5,989,813 | A | 11/1999 | Gerdes |
| 6,040,138 | A | 3/2000 | Lockhart et al. |
| 6,110,462 | A | 8/2000 | Barbas et al. |
| 6,287,765 | B1 | 9/2001 | Cubicciotti |
| 6,316,194 | B1 | 11/2001 | Karn et al. |
| 6,361,944 | B1 * | 3/2002 | Mirkin et al. .................. 435/6 |
| 6,451,535 | B1 | 9/2002 | Jenne et al. |
| 6,485,982 | B1 | 11/2002 | Charlton |
| 6,541,617 | B1 | 4/2003 | Bamdad et al. |
| 6,630,306 | B1 | 10/2003 | Breaker |
| 6,706,474 | B1 | 3/2004 | Lu et al. |
| 6,818,455 | B2 | 11/2004 | May et al. |
| 6,849,414 | B2 | 2/2005 | Guan et al. |
| 6,890,719 | B2 | 5/2005 | Lu et al. |
| 7,192,708 | B2 | 3/2007 | Lu et al. |
| 2003/0215810 | A1 | 11/2003 | Lu et al. |
| 2004/0018515 | A1 | 1/2004 | Diener et al. |
| 2004/0126882 | A1 | 7/2004 | Ellington et al. |
| 2004/0175693 | A1 | 9/2004 | Lu et al. |
| 2005/0136500 | A1 | 6/2005 | Yang et al. |
| 2005/0282186 | A1 | 12/2005 | Lu et al. |
| 2006/0019406 | A1 | 1/2006 | Wei et al. |
| 2006/0094026 | A1 | 5/2006 | Lu et al. |
| 2006/0166222 | A1 | 7/2006 | Lu et al. |
| 2007/0037171 | A1 | 2/2007 | Lu et al. |
| 2007/0269821 | A1 | 11/2007 | Mazumdar et al. |
| 2008/0176228 | A1 | 7/2008 | Lu et al. |

FOREIGN PATENT DOCUMENTS

| EP | 121970 | 10/1984 |
| EP | 1219708 | 7/2002 |
| EP | 1 312 674 | 5/2003 |
| GB | 2339280 | 1/2000 |
| WO | WO 96/17086 | 6/1996 |
| WO | WO 97/09342 | 3/1997 |
| WO | WO 98/04740 | 2/1998 |
| WO | WO 98/27104 | 6/1998 |
| WO | WO 98/39484 | 9/1998 |
| WO | WO 98/49346 | 11/1998 |
| WO | WO 99/13338 | 3/1999 |
| WO | WO 99/27351 | 6/1999 |
| WO | WO 99/47704 | 9/1999 |
| WO | WO 00/26226 | 5/2000 |
| WO | WO 00/58505 | 10/2000 |
| WO | WO 01/00876 | 1/2001 |
| WO | WO 01/23548 | 4/2001 |
| WO | WO 01/024696 | 4/2001 |
| WO | WO 01/27612 A2 | 4/2001 |
| WO | WO 01/27612 A3 | 4/2001 |
| WO | WO 01/51665 | 7/2001 |
| WO | WO 01/73123 | 10/2001 |

(Continued)

OTHER PUBLICATIONS

Li et al. A Highly Sensitive and Selective Catalytic DNA Biosensor for Lead Ions, Journal of the American Chemical Society, 2000, vol. 122, p. 10466.*
Li et al. In vitro selection and characterization of a highly efficient Zn(II)-dependent RNA-cleaving deoxyribozyme, Nucleic Acids Research, 2000, vol. 28, p. 481.*
Lott et al. A two-metal ion mechanism operates in the hammerhead ribozyme-mediated cleavage of and RNA substrate, Proceedings of the National Academy of Sciences of the USA, 1998, vol. 95, p. 542.*
Definition of the word "ion" printed from Merriam-Webster online dictionary (www.m-w.com) on Jun. 30, 2004.*
Definition of the word "particle" printed from Merriam-Webster online dictionary (www.m-w.com) on Jun. 29, 2004.*
Breaker and Joyce, A DNA enzyme with Mg2+-dependent RNA phosphoesterase activity, Chemistry & Biology, 1995, vol. 2, p. 655.*
Faulhammer and Famulok, The Ca2+ Ion as a Cofactor for a Novel RNA-Cleaving Deoxyribozyme, Angewandte Chemie International Edition in English, 1996, vol. 35, p. 2837.*
Allara and Nuzzo, Langmuir, 1, 45 (1985).

(Continued)

Primary Examiner—Tracy Vivlemore
(74) Attorney, Agent, or Firm—Evan Law Group LLC

(57) ABSTRACT

Disclosed are compositions and methods for the sensitive and selective detection of ions using nucleic acid enzymes and DNA modified microparticles.

7 Claims, 8 Drawing Sheets

FOREIGN PATENT DOCUMENTS

| WO | WO 02/00006 | 1/2002 |
|---|---|---|
| WO | WO 02/22882 | 3/2002 |
| WO | WO 02/098364 | 12/2002 |
| WO | WO 03/062422 | 7/2003 |
| WO | WO 03/068963 | 8/2003 |
| WO | WO 03/094838 | 11/2003 |
| WO | WO 03/095648 | 11/2003 |
| WO | 2004/081235 | 9/2004 |
| WO | WO 2005/095967 | 10/2005 |
| WO | WO 2005/100602 | 10/2005 |
| WO | WO 2006/048164 | 5/2006 |
| WO | WO 2006/052419 | 5/2006 |
| WO | WO 2006/078660 | 7/2006 |
| WO | WO 2007/106118 | 9/2007 |
| WO | WO 2007/109500 | 9/2007 |
| WO | WO 2008/089248 | 7/2008 |

OTHER PUBLICATIONS

Bain & Whitesides, (1989) Angew. Chem. Rev. Ed. Eng., 28, 506-512.
Breaker, R. R.; Joyce, G. F. Chem. Biol. 1995, 2, 655-660.
Breaker, R.R. & Joyce, G.F. (1995) A DNA enzyme that cleaves RNA. Chem. Biol. 1, 223-229.
Breaker, R.R. (1997) DNA enzymes. Nat. Biotechnol. 15, 427-431.
Brust et al., (1995) Adv. Mater., 7, 795-797.
Burwell, (1974) Chemical Technology, 4, 370-377.
Cadwell, R. C.; Joyce, G. F. PCR Methods Appl. 1992, 2, 28-33.
Cadwell, R. C.; Joyce, G. F. PCR Methods Appl. 1994, 3, S136-S140.
Carmi, N., Shultz, L.A. & Breaker, R.R. (1996) In vitro selection of self-cleaving DNAs. Chem. Biol. 3, 1039-1046.
Chapman, K. B.; Szostak, J. W. Curr. Opin. Struct. Biol. 1994, 4, 618-622.
Chen et al., J. Am Chem. Soc., (1989) 111, 6402-6407.
Chen & Seeman, Nature, (1991) 350, 631-633.
Chen et al., (1994) Biochem., 33, 13540-13546.
Ciesiolka, J.; Gorski, J.; Yarus, M. RNA 1995, 1, 538-550.
Ciesiolka, J.; Yarus, M. RNA 1996, 2, 785-793.
Conaty, J.; Hendry, P.; Lockett, T. Nucleic Acids Res. 1999, 27, 2400-2407.
Conn, M. M.; Prudent, J. R.; Schultz, P. G. J. Am. Chem. Soc. 1996, 118, 7012-7013.
Cuenoud, B. & Szostak, J.W. A DNA metalloenzyme with DNA ligase activity. Nature 375. 611-614 (1995).
Dai, X.; De Mesmaeker, A.; Joyce, G. F. Science 1995, 267, 237-240.
Deo, S. & Godwin, H.A. A Selective, Ratiometric Fluorescent Sensor for $Pb^{2+}$. J. Am. Chem. Soc. 122, 174-175 (2000).
Dubois & Nuzzo, (1992) Annu. Rev. Phys. Chem., 43, 437-463.
Earnshaw & Gait, "Modified Oligoribonucleotides as site-specific probes of RNA structure and function," Biopolymers (John Wiley & Sons, Inc.) 48:39-55, 1998.
Ekland, E. H.; Szostak, J. W.; Bartel, D. P. Science 1995, 269, 364-370.
Ekland, E. H.; Bartel, D. P. Nature 1996, 382, 373-376.
Famulok, M. Curr. Opin. Struct. Biol. 1999, 9, 324-329.
Faulhammer, D.; Famulok, M. Angew. Chem., Int. Ed. Engl. 1996, 35, 2837-2841.
Frank, D. N.; Pace, N. R. Proc. Natl. Acad. Sci. U. S. A. 1997, 94, 14355-14360.
Frenz, (1973) Nature Phys. Sci., 241, 20-22.
Geyer, C. R.; Sen, D. Chem. Biol. 1997, 4, 579-593.
Grabar, K. C. et al., (1995) Anal. Chem., 67(4), 735-743.
Hennrich, G.; Sonnenschein, H.; Resch-Genger, U. J. Am. Chem. Soc. 1999, 121, 5073-5074.
Iler, The Chemistry Of Silica, Chapter 6, (Wiley 1979).
Illangasekare, M.; Yarus, M. J. Mol. Biol. 1997, 268, 631-639.
Jhaveri, et al., Designed Signaling Aptamers that Transduce Molecular Recognition to Changes in Fluorescence Intensity, Journal of the American Chemical Society; 2000; 122(11); 2469-2473.
Joyce, G. F. Curr. Opin. Struct. Biol. 1994, 4, 331-336.

Koizumi, M.; Soukup, G. A.; Kerr, J. N. Q.; Breaker, R. R. Nat. Struct. Biol. 1999, 6, 1062-1071.
Lee, M., & Walt, D. R. A fiber-optic microarray biosensor using aptamers as receptors. Anal Biochem 282(1):142-146, 2000.
Lehman, N.; Joyce, G. F. Nature 1993, 361, 182-185.
Li, J., Zheng, W., Kwon, A.H. & Lu, Y. In vitro selection and characterization of a highly efficient Zn(II)-dependent RNA-cleaving deoxyribozyme. Nucleic Acids Res. 28, 481-488 (2000).
Li, Y.; Sen, D. Nat. Struct. Biol. 1996, 2, 743-747.
Li, Y.; Breaker, R. R. Proc. Natl. Acad. Sci. U. S. A. 1999, 96, 2746-2751.
Li, Y.; Liu, Y.; Breaker, R. R. Biochemistry 2000, 39, 3106-3114.
Lohse, P. A.; Szostak, J. W. Nature 1996, 381, 442-444.
Lorsch, J. R.; Szostak, J. W. Nature 1994, 371, 31-36.
Maoz and Sagiv, (1987) Langmuir, 3, 1034-1044.
Marsh et al., (1995) Nucleic Acids Res., 23, 696-700.
Matteucci and Caruthers, (1981) J. Am. Chem. Soc., 103, 3185-3191.
Mirkin & Frank-Kameretskii, (1994) Annu. Review Biophys. Biomol. Struct., 23, 541-576.
Mucic et al., (1996) Chem. Commun. 555-557.
Nuzzo et al., J. Am. Chem. Soc., 109, 2358-2368 (1987).
Oehme, I. & Wolfbeis, O.S. Optical sensors for determination of heavy metal ions. Mikrochim. Acta 126, 177-192 (1997).
Pan, T.; & Uhlenbeck, O.C. A small metalloribozyme with a two-step mechanism. Nature 358, 560-563 (1992).
Pan, T.; Dichtl, B.; Uhlenbeck, O. C. Biochemistry 1994, 33, 9561-9565.
Pearce, D. A.; Walkup, G. K.; Imperiali, B. Bioorg. Med. Chem. Lett. 1998, 8, 1963-1968.
Piccirilli, J. A.; McConnell, T. S.; Zaug, A. J.; Noller, H. F.; Cech, T. R. Science 1992, 256, 1420-1424.
Pley, H. W.; Flaherty, K. M.; McKay, D. B. Nature 1994, 372, 68-74.
Potyrailo, R.A., Conrad, R.C., Ellington, A.D. & Hieftje, G.M. (1998). Adapting Selected Nucleic Acid Ligands (Aptamers) to Biosensors. Anal. Chem. 70: 3419-3425.
Prudent, J. R.; Uno, T.; Schultz, P. G. Science 1994, 264, 1924-1927.
Robertson, M. P.; Ellington, A. D. Nat. Biotechnol. 1999, 17, 62-66.
Robertson, M. P., Ellington, A. D. Nucleic Acids Res. 2000, 28, 1751-1759.
Roth, A.; Breaker, R. R. Proc. Natl. Acad. Sci. U. S. A. 1998, 95, 6027-6031.
Rurack, K., Kollmannsberger, M., Resch-Genger, U. & Daub, J. A Selective and Sensitive Fluoroionophore for HgII, AgI, and CuII with Virtually Decoupled Fluorophore and Receptor Units. J. Am. Chem. Soc. 122, 968-969 (2000).
Santoro, S. W.; Joyce, G. F. Proc. Natl. Acad. Sci. U. S. A. 1997, 94, 4262-4266.
Santoro, S.W., Joyce, G.F., Sakthivel, K., Gramatikova, S. & Barbas, C.F., III RNA Cleavage by a DNA Enzyme with Extended Chemical Functionality. J. Am. Chem. Soc. 122, 2433-2439 (2000).
Seeman et al., (1993) New J. Chem., 17, 739-755.
Shaiu et al., (1993) Nuc. Acids Res., 21, 99-103.
Shaw & Wang, (1993) Science, 260, 533-536.
Shekhtman et al., (1993) New J. Chem., 17, 757-763.
Smith and Feigon, Nature, (1992) 356, 164-168.
Soriaga and Hubbard, (1982) J. Am. Chem. Soc., 104, 3937-3945.
Tang and Breaker, Proc. Natl. Acad. Sci. USA, 97, 5784-5789 (2000).
Tarasow, T. M.; Tarasow, S. L.; Eaton, B. E. Nature 1997, 389, 54-57.
Timmons and Zisman, (1965) J. Phys. Chem., 69, 984-990.
Tompkins and Allara, (1974) J. Colloid Interface Sci., 49, 410-421.
Tsang, J.; Joyce, G. F. Methods Enzymol. 1996, 267, 410-426.
Tuerk, C.; Gold, L. Science 1990, 249, 505-510.
Uphoff, K. W.; Bell, S. D.; Ellington, A. D. Curr. Opin. Struct. Biol. 1996, 6, 281-288.
Vaish, N. K.; Heaton, P. A.; Fedorova, O.; Eckstein, F. Proc. Natl. Acad. Sci. U. S. A. 1998, 95, 2158-2162.
Walkup, G.K. & Imperiali, B. Design and Evaluation of a Peptidyl Fluorescent Chemosensor for Divalent Zinc. J. Am. Chem. Soc. 118, 3053-3054 (1996).
Wang et al., Biochem., (1993) 32, 1899-1904.
Wang et al., (1991) Biochem., 30, 5667-5674.
Wecker, M.; Smith, D.; Gold, L. RNA 1996, 2, 982-994.
Wells, J. Biol. Chem. (1988), 263, 1095-1098.

Whitesides (1995) Proceedings of the Robert A. Welsh Foundation 39th Conference On Chemical Research Nanophase Chemistry, Houston, Tex., pp. 109-121.
Wiegand, T. W.; Janssen, R. C.; Eaton, B. E. *Chem. Biol.* 1997, 4, 675-683.
Wilson, C.; Szostak, J. W. *Nature* 1995, 374, 777-782.
Winkler, J.D., Bowen, C.M. & Michelet, V. Photodynamic Fluorescent Metal Ion Sensors with Parts per Billion Sensitivity, *J. Am. Chem. Soc.* 120, 3237-3242 (1998).
Zhang, B.; Cech, T. R. *Nature* 1997, 390, 96-100.
Zillmann, M.; Limauro, S. E.; Goodchild, J. *RNA* 1997, 3, 734-747.
Breaker, R.R., "DNA Enzymes," Nature Biotechnology, vol. 15, No. 5, pp. 427-431, May 1997.
Breaker, R.R., et al., "A DNA Enzyme with $Mg^{2+}$-Dependent RNA Phophoesterase Activity" Chemistry & Biology, vol. 2, No. 10, pp. 655-660, Oct. 1995.
Li, J., et al., "A Highly Sensitive and Selective Catalytic DNA Biosensor for Lead Ions", American Chemical Society, vol. 122, No. 42, pp. 10466-10467, Oct. 2000.
Abstract of Joyce, G., "Design and catalytic activity of enzyumic DNA molecules"., (1998).
Aggarwal, S.K., et al., "Determination of lead in urine and whole blood by stable isotope dilution gas chromatography-mass spectrometry"., Clinical Chemistry, vol. 40, No. 8, pp. 1494-1502, (1994).
Alivisatos, A.P., et al., "Organization of "nanocrystal molecules" using DNA"., Nature, vol. 382, pp. 609-611, (1996).
Allara, D. et al., "Spontaneously organized molecular assemblies. 1.Formation, dynamics and physical properties of n-alkanoic acids adsorbed from solution on an oxidized aluminum surface"., Langmuir, vol. 1, No. 1, pp. 45-52, (1985).
Andreola, M-L., et al., "DNA aptamers selected against the HIV-1 RNase H display in vitro antiviral activity"., Biochemistry, vol. 40, No. 34, pp. 10087-10094, (2001).
Bain, C. D., et al., "Modeling organic surfaces with self-assembled monolayers"., Angew. Chem. Int. Ed. Engl., vol. 28, No. 4, pp. 506-512, (1989).
Bannon, D.I., et al., "Graphite furnace atomic absorption spectroscopic measurement of blood lead in matrix-matched standards"., Clinical Chemistry, vol. 40, No. 9, pp. 1730-1734, (1994).
Been, M.D., et al., "Self-cleaving ribozymes of hepatitis delta virus RNA"., Eur. J. Biochem., vol. 247, pp. 741-753, (1997).
Berens, C., et al., "A tetracycline-binding RNA aptamer"., Bioorganic & Medicinal Chemistry, vol. 9, pp. 2549-2556, (2001).
Biroccio, A., et al., "Selection of RNA aptamers that are specific and high-affinity ligands of the hepatitis C virus RNA-dependent RNA polymerase"., Journal of Virology, vol. 76, No. 8, pp. 3688-3696, (2002).
Blake, D.A., et al., "Antibody-based sensors for heavy metal ions"., Biosensors & Bioelectronics, vol. 16, pp. 799-809, (2001).
Blank, M., et al., "Systematic evolution of a DNA aptamer binding to rat brain tumor microvessels. Selective targeting of endothelial regulatory protein pigpen"., Journal of Biological Chemistry, vol. 276, No. 19, pp. 16464-16468, (2001).
Bock, L.C., et al., "Selection of single-stranded DNA molecules that bind and inhibit human thrombin"., Nature, vol. 355, pp. 564-566, (1992).
Bogden, J.D., et al., "Soil contamination from lead in paint chips"., Bulletin of Environmental Contamination & Toxicology, vol. 14, No. 3, pp. 289-294, (1975).
Boiziau, C., et al., "DNA aptamers selected against the HIV-1 trans-activation-responsive RNA element form RNA-DNA kissing complexes"., Journal of Biological Chemistry, vol. 274, No. 18, pp. 12730-12737, (1999).
Bowins, R.J., et al., "Electrothermal isotope dilution inductively coupled plasma mass spectrometry method for the determination of sub-ng $ml^{-1}$ levels of lead in human plasma"., Journal of Analytical Atomic Spectrometry, vol. 9, pp. 1233-1236, (1994).
Breaker, R.R., "Catalytic DNA: in training and seeking employment"., Nature Biotechnology, vol. 17, pp. 422-423, (1999).
Breaker, R.R., "DNA aptamers and DNA enzymes" Current Opinion in Chemical Biology, vol. 1, pp. 26-31, (1997).
Breaker, R.R., "DNA enzymes"., Nature Biotechnology, vol. 15, pp. 427-431, (1997).

Breaker, R.R., "Molecular Biology: Making Catalytic DNAs"., Science, vol. 290, issue 5499, pp. 2095-2096, (2000).
Breaker, R.R., et al., "A DNA enzyme that cleaves RNA"., Chemistry & Biology, vol. 1, No. 4, pp. 223-229, (1994).
Breaker, R.R., et al., "A DNA enzyme with $Mg^{2+}$-dependent RNA phosphoesterase activity"., Chemistry & Biology, vol. 2, No. 10, pp. 655-660, (1995).
Breaker, R.R., et al., "Engineered allosteric ribozymes as biosensor components"., Current Opinion in Biotechnology, vol. 13, pp. 31-39, (2002).
Brody, E.N., et al., "Aptamers as therapeutic and diagnostic agents"., Reviews in Molecular Biotechnology, vol. 74, pp. 5-13, (2000).
Broude, N.E., "Stem-loop oligonucleotides: a robust tool for molecular biology and biotechnology", Trends in Biotechnology, vol. 20, No. 6, pp. 246-256, (2002).
Brown, A.K., et al., "A lead-dependent DNAzyme with a two-step mechanism"., Biochemistry, vol. 42, No. 23, pp. 7152-7161, (2003).
Bruesehoff, P.J., et al., "Improving metal ion specificity during In Vitro selection of catalytic DNA"., Combinatorial Chemistry & High Throughput Screening, vol. 5, pp. 327-335, (2002).
Bruno, J.G., et al., "In vitro selection of DNA aptamers to anthrax spores with electrochemiluminescence detection"., Biosensors & Bioelectronics, vol. 14, pp. 457-464, (1999).
Bruno, J.G., et al., "Use of magnetic beads in selection and detection of biotoxin aptamers by electrochemiluminescence and enzymatic methods"., BioTechniques, vol. 32, No. 1, pp. 178-180, pp. 182-183, (2002).
Brust, M., et al., "Novel gold-dithiol nano-networks with non-metallic electronic properties"., Advanced Materials, vol. 7, No. 9, pp. 795-797, (1995).
Burdette, S.C., et al., "Fluorescent Sensors for $Zn^{2+}$ Based on a Fluorescein Platform: Synthesis, Properties and Intracellular Distribution"., J. Am. Chem. Soc., vol. 123, No. 32, pp. 7831-7841, (2001).
Burgstaller, P., et al., "Isolation of RNA aptamers for biological cofactors by in vitro selection"., Angew. Chem. Int. Ed. Engl, vol. 33, No. 10, pp. 1084-1087, (1994).
Burgstaller, P., et al., "Structural probing and damage selection of citrulline- and arginine-specific RNA aptamers identify base positions required for binding"., Nucleic Acids Research, vol. 23, No. 23, pp. 4769-4776, (1995).
Burke, D.H., et al., "A Novel Acidophilic RNA Motif That Recognizes Coenzyme A"., Biochemistry, vol. 37, No. 13, pp. 4653-4663, (1998).
Burke, D.H., et al., "RNA aptamers to the adenosine moiety of S-adenosyl methionine: structural inferences from variations on a theme and the reproducibility of SELEX"., Nucleic Acids Research, vol. 25, No. 10, pp. 2020-2024, (1997).
Burke, D.H., et al., "RNA aptamers to the peptidyl transferase inhibitor chloramphenicol"., Chemistry & Biology, vol. 4, No. 11, pp. 833-843, (1997).
Burmeister, J., et al., "Cofactor-assisted self-cleavage in DNA libraries with a 3'-5'-phosphoramidate bond"., Angew. Chem. Int. Ed. Engl., vol. 36, No. 12, pp. 1321-1324, (1997).
Burwell Jr., R.L., "Modified silica gels as adsorbents and catalysts"., Chemical Technology, 4, pp. 370-377, (1974).
Cadwell, R.C., et al., "Mutagenic PCR"., PCR Methods and Applications, vol. 3, pp. S136-S140, (1994).
Cadwell, R.C., et al., "Randomization of genes by PCR mutagenesis"., PCR Methods and Applications, vol. 2, pp. 28-33, (1992).
Cake, K.M., et al., "In vivo x-ray fluorescence of bone lead in the study of human lead metabolism: serum lead, whole blood lead, bone lead, and cumulative exposure"., Advances in X-Ray Analysis, vol. 38, pp. 601-606, (1995).
Camara Rica, C., et al., "Determination of trace concentrations of lead and nickel in human milk by electrothermal atomisation atomic absorption spectrophotometry and inductively coupled plasma emission spectroscopy"., The Science of the Total Environment, vol. 22, pp. 193-201, (1982).
Cao, Y.W., et al., "DNA-modified core-shell Ag/Au nanoparticles"., J. Am. Chem. Soc., vol. 123, No. 32, pp. 7961-7962, (2001).
Carmi, N., et al., "Cleaving DNA and DNA"., Proc. Natl. Acad. Sci. USA, vol. 95, pp. 2233-2237, (1998).

Carmi, N., et al., "In vitro selection of self-cleaving DNAs"., Chemistry & Biology, vol. 3, No. 12, pp. 1039-1046, (1996).

Cech, T.R., "Structure and mechanism of the large catalytic RNAs: group I and group II introns and ribonuclease P"., The RNA World, pp. 239-269, Cold Spring Harbor Laboratory Press, Cold Spring Harbor, New York, (1993).

Cech, T.R., et al., "Group I ribozymes: substrate recognition, catalytic strategies, and comparative mechanistic analysis"., Nucleic Acids and Molecular Biology, vol. 10, pp. 1-17, (1996).

Chaloin, L., et al., "Endogenous expression of a high-affinity pseudoknot RNA aptamer suppresses replication of HIV-1"., Nucleic Acids Research, vol. 30, No. 18, pp. 4001-4008, (2002).

Chapman, K.B., et al., "In vitro selection of catalytic RNAs"., Current Opinion in Structural Biology, vol. 4, pp. 618-622, (1994).

Chartrand, P., et al., "Effect of structural modifications on the activity of the leadzyme"., Biochemistry, vol. 36, No. 11, pp. 3145-3150, (1997).

Chen, J., et al., "Synthesis from DNA of a molecule with the connectivity of a cube"., Nature, vol. 350, pp. 631-633, (1991).

Chen, C-T., et al., "A highly selective fluorescent chemosensor for lead ions"., J. Am. Chem. Soc., vol. 124, pp. 6246-6247, (2002).

Chen, J-H., et al., "A specific quadrilateral synthesized from DNA branched junctions"., J. Am. Chem. Soc., vol. 111, No. 16, pp. 6402-6407, (1989).

Chen, L., et al., "Crystal structure of a four-stranded intercalated DNA: $d(C_4)$"., Biochemistry, vol. 33, No. 46, pp. 13540-13546, (1994).

Chinnapen, D.J.F., et al., "Hemin-stimulated docking of cytochrome c to a hemin—DNA aptamer complex"., Biochemistry, vol. 41, No. 16, pp. 5202-5212, (2002).

Ciesiolka, J., et al., "Selection of an RNA domain that binds $Zn^{2+}$"., RNA, vol. 1, pp. 538-550, (1995).

Ciesiolka, J., et al., "Small RNA-divalent domains"., RNA, vol. 2, pp. 785-793, (1996).

Conaty, J., et al., "Selected classes of minimised hammerhead ribozyme have very high cleavage rates at low $Mg^{2+}$ concentration"., Nucleic Acids Research, vol. 27, No. 11, pp. 2400-2407, (1999).

Conn, M.M., et al., "Porphyrin Metalation Catalyzed by a Small RNA Molecule"., J. Am. Chem. Soc, vol. 118, No. 29, pp. 7012-7013, (1996).

Connell, G.J., et al., "RNAs with dual specificity and dual RNAs with similar specificity"., Science, New Series, vol. 264, issue 5162, pp. 1137-1141, (1994).

Connell, G.J., et al., "Three small ribooligonucleotides with specific arginine sites"., Biochemistry, vol. 32, No. 21, pp. 5497-5502, (1993).

Cuenoud, B., et al., "A DNA metalloenzyme with DNA ligase activity"., Nature, vol. 375, pp. 611-614, (1995).

Czarnik, A.W., "Desperately seeking sensors"., Chemistry & Biology, vol. 2, No. 7, pp. 423-428, (1995).

Dai, X., et al., "Cleavage of an amide bond by a ribozyme"., Science, New Series, vol. 267, issued 5195, pp. 237-240, (1995).

Davis, J.H., et al., "Isolation of high-affinity GTP aptamers from partially structured RNA libraries"., Proc. Natl. Acad. Sci. USA, vol. 99, No. 18, pp. 11616-11621, (2002).

Davis, K.A., et al., "Staining of cell surface human CD4 with 2'-F-pyrimidine-containing RNA aptamers for flow cytometry"., Nucleic Acids Research, vol. 26, No. 17, pp. 3915-3924, (1998).

Definition of the word "ion" printed from Merriam-Webster online dictionary (wwww.m-w.com) on Jun. 30, 2004.

Definition of the word "particle" printed from Merriam-Webster online dictionary (www.m-w.com) on Jun. 29, 2004.

Deo, S., et al., "A Selective, Ratiometric Fluorescent Sensor for $Pb^{2+}$" J. Am. Chem. Soc., vol. 122, No. 1, pp. 174-175, (2000).

Derose, V.J., "Two Decades of RNA Catalysis"., Chemistry & Biology, vol. 9, pp. 961-969, (2002).

Didenko, V.V., "DNA probes using fluorescence resonance energy transfer (FRET): Designs and applications"., BioTechniques, vol. 31, pp. 1106-1121, (2001). We have reference, but we are missing pp. 1119-1121.

Doudna, J.A., et al., "The Chemical Repertoire of Natural Ribozymes"., Nature, vol. 418, pp. 222-228, (2002).

Dubois, L.H., et al., "Synthesis, structure, and properties of model organic surfaces"., Annu. Rev. Phys. Chem., vol. 43, pp. 437-463, (1992).

Earnshaw, D.J., et al., "Modified oligoribonucleotides as site-specific probes of RNA structure and function"., Biopolymers (Nucleic Acid Sciences), vol. 48, pp. 39-55, (1998).

Ekland, E.H., et al., "RNA-catalysed RNA polymerization using nucleoside triphosphates"., Nature, vol. 382, pp. 373-376, (1996).

Ekland, E.H., et al., "Structurally complex and highly active RNA ligases derived from random RNA sequences"., Science, vol. 269, issue 5222, pp. 364-370, (1995).

Elghanian, R., et al., "Selective colorimetric detection of polynucleotides based on the distance-dependent optical properties of gold nanoparticles"., Science, vol. 277, pp. 1078-1081, (1997).

Ellington, A.D., et al., "Aptamers as potential nucleic acid pharmaceuticals"., Biotechnology Annual Review, vol. 1, pp. 185-214, (1995).

Ellington, A.D., et al., "In vitro selection of RNA molecules that bind specific ligands"., Nature, vol. 346, pp. 818-822, (1990).

Ellington, A.D., et al., "Selection in vitro of single-stranded DNA molecules that fold into specific ligand-binding structures"., Nature, vol. 355, pp. 850-852, (1992).

Famulok, M., "Molecular Recognition of Amino Acids by RNA-Aptamers: An L-Citrulline Binding RNA Motif and Its Evolution into an L-Arginine Binder"., J. Am. Chem. Soc., vol. 116, No. 5, pp. 1698-1706, (1994).

Famulok, M., "Oligonucleotide aptamers that recognize small molecules", Current Opinion in Structural Biology. vol. 9, pp. 324-329, (1999).

Famulok, M., et al., "In Vitro Selection Analysis of Neomycin Binding RNAs with a Mutagenized Pool of Variants of the 16S rRNA Decoding Region"., Biochemistry, vol. 35, No. 14, pp. 4265-4270, (1996).

Famulok, M., et al., "Stereospecific recognition of tryptophan agarose by in vitro selected RNA"., J. Am. Chem. Soc., vol. 114, No. 10, pp. 3990-3991, (1992).

Faulhammer, D., et al., "Characterization and Divalent Metal-ion Dependence of in Vitro Selected Deoxyribozymes which Cleave DNA/RNA Chimeric Oligonucleotides"., J. Mol. Biol., vol.269, pp. 188-202, (1997).

Faulhammer, D., et al., "The $Ca^{2+}$ ion as a cofactor for a novel RNA-cleaving deoxyribozyme"., Angew. Chem., Int. Ed. Engl., vol. 35, No. 23/24, pp. 2837-2841, (1996).

Feldman, B.J., et al., "Determination of lead in blood by square wave anodic stripping voltammetry at a carbon disk ultramicroelectrode"., Analytical Chemistry, vol. 66, No. 13, pp. 1983-1987, (1994).

Ferguson, A., et al., "A novel strategy for selection of allosteric ribozymes yields riboreporter™ sensors for caffeine and aspartame"., Nucleic Acids Research, vol. 32, No. 5, pp. 1756-1766, (2004).

Fodor, S.P.A., et al., "Light-directed, spatially addressable parallel chemical synthesis"., Science, New Series, vol. 251, issue 4995, pp. 767-773, (1991).

Frank, D.N., et al., "In vitro selection for altered divalent metal specificity in the RNase P RNA"., Proc. Natl. Acad. Sci. USA, vol. 94, pp. 14355-14360, (1997).

Frens, G., et al., "Controlled Nucleation for the regulation of the particle size in monodisperse gold suspensions"., Nature Physical Science, vol. 241, pp. 20-22, (1973).

Fukusaki, E-I., et al., "DNA aptamers that bind to chitin"., Bioorganic & Medicinal Chemistry letters, vol. 10, pp. 423-425, (2000).

Geiger, A., et al., "RNA aptamers that bind L-arginine with sub-micromolar dissociation constants and high enantioselectivity"., Nucleic Acids Research, vol. 24, No. 6, pp. 1029-1036, (1996).

Geyer, C.R., et al., "Evidence for the metal-cofactor independence of an RNA phosphodiester-cleaving DNA enzyme"., Chemistry & Biology, vol. 4, No. 8, pp. 579-593, (1997).

Geyer, C.R., et al., "Lanthanide Probes for a Phosphodiester-cleaving, Lead-dependent, DNAzyme", J. Mol. Biol., vol. 275, pp. 483-489, (1998).

Giver, L., et al., "Selection and design of high-affinity RNA ligands for HIV-1 Rev"., Gene, vol. 137, pp. 19-24, (1993).

Giver, L., et al., "Selective optimization of the Rev-binding element of HIV-1".,Nucleic Acids Research, vol. 21, No. 23, pp. 5509-5516, (1993).

Godwin, H.A., et al., "A Flourescent Zinc Probe Based on Metal-Induced Peptide Folding"., J. Am. Chem. Soc., vol. 118, pp. 6514-6515, (1996).

Grabar, K., et al., "Preparation and characterization of Au colloid Monolayers"., Analytical chemistry, vol. 67, No. 4, pp. 735-743, (1995).

Granadillo, V.A., et al., "The influence of the blood levels of lead, aluminum and vanadium upon the arterial hypertension"., Clinica Chimica Acta, vol. 233, pp. 47-59, (1995).

Grate, D., et al., "Laser-mediated, site-specific inactivation of RNA transcripts"., Proc. Natl. Acad. Sci. USA, vol. 96, pp. 6131-6136, (1999).

Guschin, D., et al., "Manual manufacturing of oligonucleotide, DNA, and protein microchips"., Analytical Biochemistry, vol. 250, pp. 203-211, (1997).

Haller, A.A., et al., "In vitro selection of a 7-methyl-guanosine binding RNA that inhibits translation of capped mRNA molecules"., Proc. Natl. Acad. Sci. USA, vol. 94, pp. 8521-8526, (1997).

Harada, K., et al., "Identification of two novel arginine binding DNAs"., The EMBO Journal, vol. 14, No. 23, pp. 5798-5811, (1995).

Hartig, J.S., et al., "Reporter ribozymes for real-time analysis of domain-specific interactions in biomolecules: HIV-1 reverse transcriptase and the primer-template complex"., Angew. Chem. Int. Ed., vol. 41, No. 22, pp. 4263-4266, (2002).

He, X-x., et al., "Bioconjugated nanoparticles for DNA protection from cleavage"., J. Am. Chem. Soc., vol. 125, No. 24, pp. 7168-7169, (2003).

Hennrich, G., et al., "Redox switchable fluorescent probe selective for either Hg(II) or Cd(II) and Zn(II)" J. Am. Chem. Soc., vol. 121, No. 21, pp. 5073-5074, (1999).

Hesselberth, J., et al., "In vitro selection of nucleic acids for diagnostic applications"., Reviews in Molecular Biotechnology, vol. 74, pp. 15-25, (2000).

Hesselberth, J.R., et al., "Simultaneous detection of diverse analytes with an aptazyme ligase array", Analytical Biochemistry vol. 312, pp. 106-112, (2003).

Ho, H-A., et al., "Optical sensors based on hybrid aptamer/conjugated polymer complexes"., J. Am. Chem. Soc., vol. 126, No. 5, pp. 1384-1387, (2004).

Hock, B., "Antibodies for immunosensors, A review"., Analytica Chimica Acta, vol. 347, pp. 177-186, (1997).

Hofmann, H.P., et al., "$Ni^{2+}$-binding RNA motifs with an asymmetric purine-rich internal loop and a G-A base pair"., RNA, vol. 3, pp. 1289-1300, (1997).

Holeman, L.A., et al., "Isolation and characterization of fluorophore-binding RNA aptamers"., Folding & Design, vol. 3, pp. 423-431, (1998).

Hoogstraten, C.G., et al., "NMR solution structure of the lead-dependent ribozyme: Evidence for dynamics in RNA catalysis"., J. Mol. Biol., vol. 284, pp. 337-350, (1998).

Hoogstraten, C.G., et al., "Structural analysis of metal ion ligation to nucleotides and nucleic acids using pulsed EPR spectroscopy"., J. Am. Chem. Soc., vol. 124, No. 5, pp. 834-842, (2002).

Huizenga, D.E., et al., "A DNA aptamer that binds adenosine and ATP"., Biochemistry, vol. 34, No. 2, pp. 656-665, (1995).

Iler, R.K., "The Chemistry of Silica: Solubility, Polymerization, Colloid and Surface Properties, and Biochemistry, Chapter 6, The surface chemistry of silica"., pp. 622-729, Wiley-Interscience Publication, New York, (1979).

Illangasekare, M., et al., "Small-molecule-substrate interactions with a self-aminoacylating ribozyme"., J. Mol. Biol., vol. 268, pp. 631-639, (1997).

Imperiali, B., et al., "Peptide platforms for metal ion sensing"., Proc. SPIE-The international society for optical engineering, vol. 3858, pp. 135-143, (1999).

International Search Report dated Jan. 15, 2003 for corresponding PCT application No. PCT/US01/20557.

International Search Report dated Aug. 1, 2003 for corresponding PCT application No. PCT/US03/08483.

Iqbal, S.S., et al., "A review of molecular recognition technologies for detection of biological threat agents"., Biosensors & Bioelectronics, vol. 15, pp. 549-578, (2000).

Jagner, D., et al., "Determination of lead in microliter amounts of whole blood by stripping potentiometry"., Electroanalysis, vol. 6, pp. 285-291, (1994).

Jayasena, S.D., "Aptamers: an emerging class of molecules that rival antibodies in diagnostics"., Clinical Chemistry, vol. 45, No. 9, pp. 1628-1650, (1999).

Jenison, R., et al., "Interference-based detection of nucleic acid targets on optically coated silicon", Nature Biotechnology, vol. 19, pp. 62-65, (2001).

Jenison, R.D., et al., "High-resolution molecular discrimination by RNA"., Science, vol. 263, pp. 1425-1429, (1994).

Jenne, A., et al., "Rapid Identification and Characterization of Hammerhead-Ribozyme Inhibitors Using Fluorescence-Based Technology"., Nature Biotechnology, vol. 19, pp. 56-61, (2001).

Jenne, A., et al., "Real-time Characterization of Ribozymes by Fluorescence Resonance Energy Transfer (FRET)"., Angewandte Chemie. International Edition, vol. 38, No. 9, pp. 1300-1303, (1999).

Jhaveri, S., et al., "In vitro selection of signaling aptamers"., Nature Biotechnology, vol. 18, pp. 1293-1297, (2000).

Jhaveri, S.D., et al., "Designed signaling aptamers that transduce molecular recognition to changes in fluorescence intensity"., J. Am. Chem. Soc., vol. 122, No. 11, pp. 2469-2473, (2000).

Jin, R., et al., "What controls the melting properties of DNA-linked gold nanoparticle assemblies?"., J. Am. Chem. Soc., vol. 125, No. 6, pp. 1643-1654, (2003).

Joos, B., et al., "Covalent attachment of hybridizable oligonucleotides to glass supports"., Analytical Biochemistry, vol. 247, pp. 96-101, (1997).

Josephson, L., et al., "Magnetic nanosensors for the detection of oligonucleotide sequences"., Angewandte Chemie. International Edition, vol. 40, No. 17, pp. 3204-3206, (2001).

Joyce, G.F., "Appendix 3: Reactions Catalyzed by RNA and DNA Enzymes". The RNA World, vol. 37, pp. 687-690, Cold Spring Harbor Laboratory Press, Cold Spring Harbor, New York, (1999).

Joyce, G.F., "In vitro evolution of nucleic acids"., Current Opinion in Structural Biology., vol. 4, pp. 331-336, (1994).

Katahira, M., et al., "Two metal-binding sites in a lead ribozyme bound to competitively by $Pb^{2+}$ and $Mg^{2+}$: Induced structural changes as revealed by NMR"., European Journal of Biochemistry, vol. 255, pp. 727-733, (1998).

Kato, T., et al., "In vitro selection of DNA aptamers which bind to cholic acid"., Biochimica et Biophysica Acta, vol. 1493, pp. 12-18, (2000).

Kawakami, J., et al., "In vitro selection of aptamers that act with $Zn^{2+}$"., Journal of Inorganic Biochemistry, vol. 82, pp. 197-206, (2000).

Khan, R., et al., "Interaction of retroviral nucleocapsid proteins with transfer $RNA^{Phe}$: a lead ribozyme and $^{1}H$ NMR study"., Nucleic Acids Research, vol. 24, No. 18, pp. 3568-3575, (1996).

Khosraviani, M., et al., "Detection of heavy metals by immunoassay: Optimization and validation of a rapid, portable assay for ionic cadmium"., Environ. Sci. Technol., vol. 32, No. 1, pp. 137-142, (1998).

Kiga, D., et al., "An RNA aptamer to the xanthine/guanine base with a distinctive mode of purine recognition"., Nucleic Acids Research, vol. 26, No. 7, pp. 1755-1760, (1998).

Kim, M.H., et al., "Activation and repression of the activity of a lead ribozyme by the combination of $Pb^{2+}$ and $Mg^{2+ 1}$"., J. Biochem., vol. 122, No. 5, pp. 1062-1067, (1997).

Klußmann, S., et al., "Mirror-image RNA that binds D-adenosine"., Nature Biotechnology, vol. 14, pp. 1112-1115, (1996).

Kohama, T., et al., "Molecular Cloning and Functional Characterization of Murine Sphingosine Kinase", The Journal of Biological Chemistry, vol. 273, No. 37, pp. 23722-23728, (1998).

Koizumi, M., et al., "Allosteric selection of ribozymes that respond to the second messengers cGMP and cAMP"., Nature Structural Biology, vol. 6, No. 11, pp. 1062-1071, (1999).

Koizumi, M., et al., "Molecular Recognition of cAMP by an RNA Aptamer"., Biochemistry, vol. 39, No. 30, pp. 8983-8992, (2000).

Koizumi, M., et al., "Allosteric ribozymes sensitive to the second messengers cAMP and cGMP"., Nucleic Acids Symposium Series, No. 42, pp. 275-276, (1999).

Kruger, K., et al., "Self-splicing RNA: autoexcision and autocyclization of the ribosomal RNA intervening sequence of the Tetrahymena"., Cell, vol. 31, pp. 147-157, (1982).

Lato, S.M., et al., "In vitro selection of RNA lectins: Using combinatorial chemistry to interpret ribozyme evolution"., Chemistry & Biology, vol. 2, No. 5, pp. 291-303, (1995).

Lauhon, C.T., et al., "RNA aptamers that bind flavin and nicotinamide redox cofactors"., J. Am. Chem. Soc., vol. 117, No. 4, pp. 1246-1257, (1995).

Lebruska, L.L., "Selection and Characterization of an RNA Decoy for Transcription Factor NF-κB"., Biochemistry, vol. 38, No. 10, pp. 3168-3174, (1999).

Lee, M., et al., "A fiber-optic microarray biosensor using aptamers as receptors"., Analytical Biochemistry, vol. 282, pp. 142-146, (2000).

Lee, S-W., et al., "Ordering of quantum dots using genetically engineered viruses"., Science, vol. 296, pp. 892-895, (2002).

Legault, P., et al., "Order, dynamics and metal-binding in the lead-dependent ribozyme"., J. Mol. Biol., vol. 284, pp. 325-335, (1998).

Lehman, N., et al., "Evolution in vitro of an RNA enzyme with altered metal dependence"., Nature, vol. 361, pp. 182-185, (1993).

Lemieux, S., et al., "Modeling active RNA structures using the intersection of conformational space: application to the lead-activated ribozyme"., RNA, vol. 4, pp. 739-749, (1998).

Levy, M., et al., "ATP-Dependent Allosteric DNA Enzymes"., Chemistry & Biology, vol. 9, pp. 417-426, (2002).

Li, J., et al., "A highly sensitive and selective catalytic DNA biosensor for lead ions"., J. Am. Chem. Soc., vol. 122, No. 42, pp. 10466-10467, (2000).

Li, J., et al., "In vitro selection and characterization of a highly efficient ZN(II)-dependent RNA-cleaving deoxyribozyme"., Nucleic Acids Research, vol. 28, No. 2, pp. 481-488, (2000).

Li, J.J., et al., "Using molecular beacons as a sensitive fluorescence assay for enzymatic cleavage of single-stranded DNA"., Nucleic Acids Research, vol. 28, No. 11, e52, pp. i-vi, (2000).

Li, Y., et al., "A catalytic DNA for porphyrin metallation"., Nature Structural Biology, vol. 3, No. 9, pp. 743-747, (1996).

Li, Y., et al., "Capping DNA with DNA"., Biochemistry, vol. 19, No. 11, pp. 3106-3114, (2000).

Li, Y., et al., "Deoxyribozymes: new players in the ancient game of biocatalysis"., Current Opinion in Structural Biology, vol. 9, pp. 315-323, (1999).

Li, Y., et al., "Phosphorylating DNA with DNA"., Proc. Natl. Acad. Sci. USA, vol. 96, pp. 2746-2751, (1999).

Link, S., et al., "Alloy formation of gold-silver nanoparticles and the dependence of the plasmon absorption on their composition"., J. Phys. Chem. B, vol. 103, No. 18, pp. 3529-3533, (1999).

Liu, H-W., et al., "Determination of cadmium, mercury and lead in seawater by electrothermal vaporization isotope dilution inductively coupled plasma mass spectrometry"., Spectrochimica Acta Part B Atomic Spectroscopy 54, pp. 1367-1375, (1999).

Liu, J., et al., "A colorimetric lead biosensor using DNAzyme-directed assembly of gold nanoparticles", J. Am. Chem. Soc., vol. 125, No. 22, pp. 6642-6643, (2003).

Liu, J., et al., "Accelerated color change of gold nanoparticles assembled by DNAzymes for simple and fast colorimetric $Pb^{2+}$ detection"., J. Am. Chem. Soc., vol. 126, No. 39, pp. 12298-12305, (2004).

Liu, J., et al., "Adenosine-dependent assembly of aptazyme-functionalized gold nanoparticles and its application as a colorimetric biosensor"., Analytical Chemistry, vol. 76, No. 6, pp. 1627-1632, (2004).

Liu, J., et al., "Colorimetric biosensors based on DNAzyme-assembled gold nanoparticles"., Journal of Fluorescence, vol. 14, No. 4, pp. 343-354, (2004).

Liu, J., et al., "Highly dispersible molecular sieve carbon nanoparticles"., Chem. Mater., vol. 16, No. 22, pp. 4205-4207, (2004).

Liu, X., et al., "A fiber-optic evanescent wave DNA biosensor based on novel molecular beacons"., Analytical Chemistry, vol. 71, No. 22, pp. 5054-5059, (1999).

Liu, Z., et al., "Assemblage of signaling DNA enzymes with intriguing metal-ion specificities and pH dependences"., J. Am. Chem. Soc., vol. 125, No. 25, pp. 7539-7545, (2003).

Lohse, P.A., et al., "Ribozyme-catalysed amino-acid transfer reactions"., Nature, vol. 381, pp. 442-444, (1996).

Lorsch, J.R., et al., "In vitro evolution of new ribozymes with polynucleotide kinase activity"., Nature, vol. 371, pp. 31-36, (1994).

Lorsch, J.R., et al., "In vitro selection of RNA aptamers specific for cyanocobalamin"., Biochemistry, vol. 33, No. 4, pp. 973-982, (1994).

Lott, W.B., et al., "A two-metal ion mechanism operates in the hammerhead ribozyme-mediated cleavage of an RNA substrate"., Proc. Natl. Acad. Sci. USA, vol. 95, pp. 542-547, (1998).

Lu, Y., "New transition-metal-dependent DNAzymes as efficient endonucleases and as selective metal biosensors"., Chem. Eur. J., vol. 8, No. 20, pp. 4589-4596, (2002).

Lu, Y., et al., "New fluorescent and colorimetric DNAzyme biosensors for metal ions", Journal of Inorganic Biochemistry, vol. 96, issue 1, pp. 30, Abstract of the 11th International Conference on Biological Inorganic Chemistry; (Jul. 15, 2003).

Majerfeld, I., et al., "An RNA pocket for an aliphatic hydrophobe"., Structural Biology, vol. 1, No. 5, pp. 287-292, (1994).

Majerfeld, I., et al., "Isoleucine:RNA sites with associated coding sequences"., RNA, vol. 4, pp. 471-478, (1998).

Mannironi, C., et al., "In vitro selection of dopamine RNA ligands"., Biochemistry, vol. 36, No. 32, pp. 9726-9734, (1997).

Maoz, R., et al., "Penetration-controlled reactions in organized monolayer assemblies. 1. Aqueous permanganate interaction with monolayer and multilayer films of long-chain surfactants"., Langmuir, vol. 3, No. 6, pp. 1034-1044, (1987).

Marcus, A.H., et al., "Estimating the contribution of lead based paint to soil lead, dust lead, and childhood blood lead"., American Society for Testing and Materials Spec. STP 1226, pp. 12-23, (1995).

Marsh, T.C., et al., "A new DNA nanostructure, the G-wire, imaged by scanning probe microscopy"., Nucleic Acids Research, vol. 23, No. 4, pp. 696-700, (1995).

Matteucci, M.D., et al., "Synthesis of Deoxyoligonucleotides on a polymer support"., J. Am. Chem. Soc., vol. 103, No. 11, pp. 3185-3191, (1981).

Mecklenburg, M., et al., "A strategy for the broad range detection of compounds with affinity for nucleic acids"., Analytica Chimica Acta, vol. 347, pp. 79-86, (1997).

Mei, S.H.J., et al., "An efficient RNA-cleaving DNA enzyme that synchronizes catalysis with fluorescence signaling"., J. Am. Chem. Soc., vol. 125, No. 2, pp. 412-420, (2003).

Meli, M., et al., "Adenine-aptamer complexes: A bipartite RNA site that binds the adenine nucleic base"., The Journal of Biological Chemistry, vol. 277, No. 3, pp. 2104-2111, (2002).

Mirkin, C.A., et al., "A DNA-based method for rationally assembling nanoparticles into macroscopic materials"., Nature, vol. 382, pp. 607-609, (1996).

Mirkin, S.M., et al., "H-DNA and related structures"., Annu. Rev. Biophys. Biomol. Struct., vol. 23, pp. 541-576, (1994).

Miyawaki, A., et al. "Fluorescent indicators for $Ca^{2+}$ based on green fluorescent proteins and calmodulin"., Nature, vol. 388, pp. 882-887, (1997).

Mucic, R.C., et al., "Synthesis and characterization of DNA with ferrocenyl groups attached to their 5'-termini: electrochemical characterization of a redox-active nucleotide monolayer"., Chem. Commun., pp. 555-557, (1996).

Mullah, B., et al., "Automated synthesis of double dye-labeled oligonucleotides using tetramethylrhodamine (TAMRA) solid supports"., Tetrahedron Letters, vol. 38, No. 33, pp. 5751-5754, (1997).

Nazarenko, I.A., et al., "A closed tube format for amplification and detection of DNA based on energy transfer"., Nucleic Acids Research, vol. 26, No. 12, pp. 2516-2521, (1997).

Nazarenko, I.A., et al., "Defining a Smaller RNA Substrate for Elongation Factor Tu"., Biochemistry, vol. 34, No. 8, pp. 2545-2552, (1995).

Niemeyer, C.M., "Nanoparticles, proteins, and nucleic acids: Biotechnology meets materials science"., Angew. Chem. Int. Edition, vol. 40, pp. 4128-4158, (2001).

Nieuwlandt, D., et al., "In Vitro Selection of RNA Ligands to Substance P"., Biochemistry, vol. 34, No. 16, pp. 5651-5659, (1995).

Nissen, P., et al., "The structural basis of ribosome activity in peptide bond synthesis"., Science, vol. 289, pp. 920-930, (2000).
Nolte, A., et al., "Mirror-design of L-oligonucleotide ligands binding to L-arginine"., Nature Biotechnology, vol. 14, pp. 1116-1119, (1996).
Nutiu, R., et al., "Structure-switching signaling aptamers"., J. Am. Chem. Soc., vol. 125, No. 16, pp. 4771-4778, (2003).
Nuzzo, R.G., et al., "Spontaneously organized molecular assemblies. 3. Preparation and properties of solution adsorbed monolayers of organic disulfides on gold surfaces"., J. Am. Chem. Soc., vol. 109, No. 8, pp. 2358-2368, (1987).
O'Donnell, M.J., et al., "High-Density, Covalent Attachment of DNA to Silicon Wafers for Analysis by MALDI-TOF Mass Spectrometry"., Analytical Chemistry, vol. 69, No. 13, pp. 2438-2443, (1997).
Oehme, I., et al., "Optical sensors for determination of heavy metal ions"., Mikrochim. Acta, vol. 126, pp. 177-192, (1997).
Ohmichi, T., et al., "Role of $Nd^{3+}$ and $Pb^{2+}$ on the RNA cleavage reaction by a small ribozyme"., Biochemistry, vol. 36, No. 12, pp. 3514-3521, (1997).
Ohmichi, T., et al., "Effect of substrate RNA sequence on the cleavage reaction by a short ribozyme"., Nucleic Acids Research, vol. 26, No. 24, pp. 5655-5661, (1998).
Okazawa, A., et al., "In vitro selection of hematoporphyrin binding DNA aptamers"., Bioorganic & Medicinal Chemistry, Letters 10, pp. 2653-2656, (2000).
Ota, N., et al., "Effects of helical structures formed by the binding arms of DNAzymes and their substrates on catalytic activity"., Nucleic Acids Research, vol. 26, No. 14, pp. 3385-3391, (1998).
Pan, T., et al., "A small metalloribozyme with a two-step mechanism"., Nature, vol. 358, pp. 560-563, (1992).
Pan, T., et al., "In vitro selection of RNAs that undergo autolytic cleavage with $Pb^{2+}$"., Biochemistry, vol. 31, No. 16, pp. 3887-3895, (1992).
Pan, T., et al., "Properties of an in vitro selected $Pb^{2+}$ cleavage motif"., Biochemistry, vol. 33, No. 32, pp. 9561-9565, (1994).
Pan, W., et al., "Isolation of virus-neutralizing RNAs from a large pool of random sequences"., Proc. Natl. Acad. Sci. USA, vol. 92, pp. 11509-11513, (1995).
Park, S-J., et al., "Array-based electrical detection of DNA with nanoparticle probes"., Science, vol. 295, pp. 1503-1506, (2002).
Parsons, P.J., et al., "A rapid Zeeman graphite furnace atomic absorption spectrometric method for the determination of lead in blood"., Spectrochimica Acta, vol. 48B, No. 6/7, pp. 925-939, (1993).
Pavlov, A.R., et al., "Determination of lead in environmental water samples by a rapid and portable immunoassay"., ANYL, Book of Abstracts, 219th ACS National Meeting, San Francisco, CA, Mar. 26-30, 2000.
Pavlov, V., et al., "Aptamer-functionalized Au nanoparticles for the amplified optical detection of thrombin"., J. Am. Chem. Soc., vol. 126, No. 38, pp. 11768-11769, (2004).
Pearce, D.A., et al., "Peptidyl chemosensors incorporating a FRET mechanism for detection of Ni(II)"., Bioorganic & Medicinal Chemistry, Letters 8, pp. 1963-1968, (1998).
Pease, A.C., et al., "Light-generated oligonucleotide arrays for rapid DNA sequence analysis"., Proc. Natl. Acad. Sci. USA, vol. 91, pp. 5022-5026, (1994).
Piccirilli, J.A., et al., "Aminoacyl esterase activity of the tetrahymena ribozyme"., Science, New Series, vol. 256, issue 5062, pp. 1420-1424, (1992).
Pley, H.W., et al., "Three-dimensional structure of a hammerhead ribozyme"., Nature, vol. 372. pp. 68-74, (1994).
Potyrailo, R.A., et al., "Adapting selected nucleic acid ligands (aptamers) to biosensors"., Analytical Chemistry, vol. 70, No. 16, pp. 3419-3425, (1998).
Prudent, J.R., et al., "Expanding the scope of RNA catalysis"., Science, New Series, vol. 264, issue 5167, pp. 1924-1927, (1994).
Qiao, H., et al., "Transferability of blood lead determinations by furnace atomic absorption spectrophotometry and continuum background correction"., Clinical Chemistry, vol. 41, No. 10, pp. 1451-1454, (1995).
Rabinowitz, M., et al., "Home refinishing, lead paint, and infant blood lead levels"., American Journal of Public Health, vol. 75, No. 4, pp. 403-404, (1985).

Rajendran, M., et al., "Selecting nucleic acids for biosensor applications"., Combinatorial Chemistry and High Throughput Screening, vol. 5, No. 4, pp. 263-270, (2002).
Rakow, N.A., et al., "A colorimetric sensor array for odour visualization"., Nature, vol. 406, pp. 710-713, (2000).
Rink, S.M., et al., "Creation of RNA molecules that recognize the oxidative lesion 7,8-dihydro-8-hydroxy-2'-deoxyguanosine (8-oxodG) in DNA"., Proc. Natl. Acad. Sci. USA, vol. 95, pp. 11619-11624, (1998).
Robertson, M.P., et al., "Design and optimization of effector-activated ribozyme ligases"., Nucleic Acids Research, vol. 28, No. 8, pp. 1751-1759, (2000).
Robertson, M.P., et al., "In vitro selection of an allosteric ribozyme that transduces analytes to amplicons"., Nature Biotechnology, vol. 17, pp. 62-66, (1999).
Roth, A., et al., "An amino acid as a cofactor for a catalytic polynucleotide"., Proc. Natl. Acad. Sci. USA, vol. 95, pp. 6027-6031, (1998).
Roychowdhury-Saha, M., et al., "Flavin Recognition by an RNA Aptamer Targeted toward FAD"., Biochemistry, vol. 41, No. 8, pp. 2492-2499, (2002).
Ruckman, J., et al., "2'-Fluoropyrimidine RNA-based aptamers to the 165-amino acid form of vascular endothelial growth factor ($VEGF_{165}$) Inhibition of receptor binding and VEGF-induced vascular permeability through interactions requiring the exon 7-encoded domain"., The Journal of Biological Chemistry, vol. 273, No. 32, pp. 20556-20567, (1998).
Rurack, K., et al., "A selective and sensitive fluoroionophore for $Hg^{II}$, $Ag^{I}$, and $Cu^{II}$ with virtually decoupled fluorophore and receptor units"., J. Am. Chem. Soc., vol. 122, No. 5, pp. 968-969, (2000).
Rusconi, C.P., et al., "RNA aptamers as reversible antagonists of coagulation factor Ixa"., Nature, vol. 419, pp. 90-94, (2002).
Sabanayagam, C.R., et al., "Oligonucleotide immobilization on micropatterened streptavidin surfaces"., Nucleic Acids Research, vol. 28, No. 8, e33, pp. i-iv, (2000).
Santoro, S.W. et al., "Mechanism and utility of an RNA-cleaving DNA enzyme"., Biochemistry, vol. 37, No. 38, pp. 13330-13342, (1998).
Santoro, S.W., et al., "A general purpose RNA-cleaving DNA enzyme"., Proc. Natl. Acad. Sci. USA, vol. 94, pp. 4262-4266, (1997).
Santoro, S.W., et al., "RNA Cleavage by a DNA Enzyme with Extended Chemical Functionality"., J. Am. Chem. Soc., vol. 122, No. 11, pp. 2433-2439, (2000).
Sassanfar, M., et al., "An RNA motif that binds ATP"., Nature, vol. 364, pp. 550-553, (1993).
Schwartz, J., et al., "The risk of lead toxicity in homes with lead paint hazard"., Environmental Research, vol. 54, No. 1, pp. 1-7, (1991).
Scott, W.G., et al., "The crystal structure of an all-RNA hammerhead ribozyme: A proposed mechanism for RNA catalytic cleavage"., Cell, vol. 81, pp. 991-1002, (1995).
Scott, W.G., "RNA catalysis"., Current Opinion in Structural Biology, vol. 8, pp. 720-726, (1998).
Search results of key word search of medline, Mar. 26, 2000.
Search results of key word search on Chemical Abstracts, Mar. 24, 2000.
Search results of key word search from various databases, Mar. 24, 2000.
Seeman, N.C., et al., "Synthetic DNA knots and catenanes"., New Journal of Chemistry, vol. 17, pp. 739-755, (1993).
Seeman, N.C., et al., "Emulating biology: Building nanostructures from the bottom up"., Proc. Natl. Acad. Sci., vol. 99, suppl. 2, pp. 6451-6455, (2002).
Seeman, N.C., "DNA in a material world"., Nature, vol. 421, pp. 427-431, (2003).
Seetharaman, S., et al., "Immobilized RNA switches for the analysis of complex chemical and biological mixtures"., Nature Biotechnology, vol. 19, pp. 336-341, (2001).
Sen, D., et al., "DNA enzymes"., Current Opinion in Chemical Biology, vol. 2, pp. 680-687, (1998).
Shaiu, W-L., et al., "Atomic force microscopy of oriented linear DNA molecules labeled with 5nm gold spheres"., Nucleic Acids Research, vol. 21, No. 1, pp. 99-103, (1993).

Shaw, S.Y., et al., "Knotting of a DNA chain during ring closure"., Science, New Series, vol. 260, issue 5107, pp. 533-536, (1993).

Shekhtman, E.M., et al., "Stereostructure of replicative DNA catenanes from eukaryotic cells"., New Journal of Chemistry, vol. 17, pp. 757-763, (1993).

Sigurdsson, S.T., et al., "Small ribozymes"., RNA Structure and Function, Cold Spring Harbor Laboratory Press (Monograph 35), pp. 339-375, (1998).

Singh, K.K., et al., "Fluorescence Polarization for Monitoring Ribozyme Reactions in Real-Time"., Biotechniques, vol. 29, No. 2, pp. 344-351, (2000).

Smith, F.W., et al., "Quadruplex structure of oxytricha telomeric DNA oligonucleotides"., Nature, vol. 356, pp. 164-168, (1992).

Smith, J.O., et al., "Molecular recognition of PNA-containing hybrids: Spontaneous assembly of helical cyanine dye aggregates of PNA templates"., J. Am. Chem. Soc., vol. 121, No. 12, pp. 2686-2695, (1999).

Soriaga, M.P., et al., "Determination of the orientation of aromatic molecules adsorbed on platinum electrodes: The effect of solute concentration"., J. Am. Chem. Soc., vol. 104, No. 14, pp. 3937-3945, (1982).

Soukup, G.A., et al., "Engineering precision RNA molecular switches"., Proc. Natl. Acad. Sci. USA, vol. 96, pp. 3584-3589, (1999).

Soukup, G.A., et al., "Allosteric nucleic acid catalysts"., Current Opinion in Structural Biology, vol. 10, pp. 318-325, (2000).

Srisawat, C., et al., "Sephadex-binging RNA ligands; rapid affinity purification of RNA from complex RNA mixtures"., Nucleic Acids Research, vol. 29, No. 2 e4, pp. 1-5, (2001).

Stage-Zimmermann, T.K., et al., "Hammerhead ribozyme kinetics"., RNA, vol. 4, pp. 875-889, (1998).

Stojanovic, M.N., et al., "Aptamer-based colorimetric probe for cocaine"., J. Am. Chem. Soc., vol. 124, No. 33, pp. 9678-9679, (2002).

Stojanovic, M.N., et al., "Aptamer-based folding fluorescent sensor for cocaine"., Journal of the American Chemical Society, vol. 123, No. 21, pp. 4928-4931, (2001).

Stojanovic, M.N., et al., "Fluorescent sensors based on aptamer self-assembly"., Journal of the American Chemical Society, vol. 122, No. 46, pp. 11547-11548, (2000).

Storhoff, J.J., et al., "Programmed materials synthesis with DNA"., Chem. Rev., vol. 99, No. 7, pp. 1849-1862, (1999).

Storhoff, J.J., et al., "What Controls the Optical Properties of DNA-Linked Gold Nanoparticle Assemblies?"., J. Am. Chem. Soc., vol. 122, No. 19, pp. 4640-4650, (2000).

Storhoff, J.J., et al., "One-pot colorimetric differentiation of polynucleotides with single based imperfections using gold nanoparticle probes"., Journal of the American Chemical Society, vol. 120, No. 9, pp. 1959-1964, (1998).

Streicher, B., et al., "Lead cleavage site in the core structure of group I intron-RNA"., Nucleic Acids Research, vol. 21, No. 2, pp. 311-317, (1993).

Sugimoto, N., et al., "Site-specific cleavage reaction catalyzed by leadzyme is enhanced by combined effect of lead and rare earth ions"., FEBS Letters, vol. 393, pp. 97-100, (1996).

Sun, L.Q., et al., "Catalytic nucleic acids: From lab to applications"., Pharmacological Reviews, vol. 52, pp. 325-347, (2000).

Tahan, J.E., et al., "Electrothermal atomic absorption spectrometric determination of Al, Cu, Ge, Pb, V and Zn in clinical samples and in cartified environmental reference materials"., Analytica Chimica Acta, vol. 295, pp. 187-197, (1994).

Takagi, Y., et al., "Survey and Summary: Recent advances in the elucidation of the mechanisms of action of ribozymes"., Nucleic Acids Research, vol. 29, No. 9, pp. 1815-1834, (2001).

Tang, J., et al., "Rational design of allosteric ribozymes"., Chemical & Biology, vol. 4, No. 6, pp. 453-459, (1997).

Tang, J., et al., "Structural diversity of self-cleaving ribozymes"., Proc. Natl. Acad. Sci. USA, vol. 97, No. 11, pp. 5784-5789, (2000).

Tanner, N.K., "Biochemistry of hepatitis delta virus catalytic RNAs"., Ribozymes in the Gene Therapy of Cancer, Chapter 3, pp. 23-38, (1998).

Tao, J., et al., "Arginine-Binding RNAs Resembling TAR Identified by in Vitro Selection".,Biochemistry, vol. 35, No. 7, pp. 2229-2238, (1996).

Tarasow, T.M., et al., "RNA-catalysed carbon-carbon bond formation"., Nature, vol. 389, pp. 54-57, (1997).

Telting-Diaz, M., et al., "Mass-produced ionophore-based fluorescent microspheres for trace level determination of lead ions"., Analytical Chemistry, vol. 74, No. 20, pp. 5251-5256, (2002).

Thompson, R.B., et al., "Determination of Picomolar Concentrations of Metal Ions Using Fluorescence Anisotropy: Biosensing with a "Reagentless" Enzyme Transducer"., Analytical Chemistry, vol. 70, No. 22, pp. 4717-4723, (1998).

Timmons, C.O., et al., "Investigation of Fatty Acid Monolayers on Metals by Contact Potential Measurements", Journal of Physical Chemistry, vol. 69, No. 3, pp. 984-990, (1965).

Tompkins, H.G., et al., "The study of the gas-solid interaction of acetic acid with a cuprous oxide surface using reflection-absorption spectroscopy"., Journal of Colloid and Interface Science, vol. 49, No. 3, pp. 410-421, (1974).

Travascio, P., et al., "A ribozyme and a catalytic DNA with peroxidase activity: active sites versus cofactor-binding sites"., Chemistry & Biology, vol. 6, No. 11, pp. 779-787, (1999).

Tsang, J., et al., "In vitro evolution of randomized ribozymes"., Methods in Enzymology, vol. 267, pp. 410-426, (1996).

Tsien, R.Y., "Fluorescent and photochemical probes of dynamic biochemical signals inside living cells"., Fluorescent Chemosensors for Ion and Molecule Recognition, (ed. Czarnik, A.W.), chapter 9, pp. 130-146, American Chemical Society, (1993).

Tuerk, C., et al., "RNA pseudoknots that inhibit human immunodeficiency virus type 1 reverse transcriptase"., Proc. Natl. Acad. Sci. USA, vol. 89, pp. 6988-6992, (1992).

Tuerk, C., et al., "Systematic evolution of ligands by exponential enrichment: RNA ligands to bacteriophage T4 DNA polymerase"., Science, New Series, vol. 249, issue 4968, pp. 505-510, (1990).

Tyagi, S., et al., "Molecular Beacons: Probes that fluoresce upon hybridization"., Nature Biotechnology, vol. 14, pp. 303-308, (1996).

Tyagi, S., et al., "Multicolor molecular beacons for allele discrimination"., Nature Biotechnology, vol. 16, pp. 49-53, (1998).

Tyagi, S., et al., "Wavelength-shifting molecular beacons"., Nature Biotechnology, vol. 18, pp. 1191-1196, (2000).

Ueyama, H., "A novel potassium sensing in aqueous media with a synthetic oligonucleotide derivative. Fluorescence resonance energy transfer associated with guanine quartet-potassium ion complex formation"., J. Am. Chem. Soc., vol. 124, No. 48, pp. 14286-14287, (2002).

Uphoff, K.W., et al., "In vitro selection of aptamers: the dearth of pure reason"., Current Opinion in Structural Biology, vol. 6, pp. 281-288, (1996).

Vaish, N.K., et al., "In vitro selection of a purine nucleotide-specific hammerhead-like ribozyme"., Proc. Natl. Acad. Sci. USA, vol. 95, pp. 2158-2162, (1998).

Valadkhan, S., et al., "Splicing-related catalysis by protein-free snRNAs"., Nature, vol. 413, pp. 701-707, (2001).

Vianini, E., et al., "In vitro selection of DNA aptamers that bind L-tyrosinamide" Bioorganic & Medicinal Chemistry, vol. 9, pp. 2543-2548, (2001).

Walkup, G.K., et al., "Design and Evaluation of a Peptidyl Fluorescent Chemosensor for Divalent Zinc"., J. Am. Chem. Soc., vol. 118, No. 12, pp. 3053-3054, (1996).

Wallace, S.T., et al., In vitro selection and characterization of streptomycin-binding RNAs: recognition discrimination between antibiotics. RNA, vol. 4, pp. 112-123, (1998).

Wallis, M.G., et al., "A novel RNA mofit for neomycin recognition"., Chemistry & Biology, vol. 2, no. 8, pp. 543-552, (1995).

Wallis, M.G., et al., "In vitro selection of a viomycin-binding RNA pseudoknot"., Chemistry & Biology, vol. 4, No. 5, pp. 357-366, (1997).

Walter, F., et al., "Folding of the four-way RNA junction of the hairpin ribozyme"., Biochemistry, vol. 37, No. 50, pp. 17629-17636, (1998).

Walter, N.G., et al., "The hairpin ribozyme: structure, assembly and catalysis"., Current Opinion in Chemical Biology, vol. 2, pp. 24-30, (1998).

Wang, D.Y., et al., "A general strategy for effector-mediated control of RNA-cleaving ribozymes and DNA enzymes"., J. Mol. Biol., vol. 318, pp. 33-43, (2002).
Wang, F., et al., "Sphingosine-1-phosphate Inhibits Motility of Human Breast Cancer Cells Independently of Cell Surface Receptors"., Cancer Research, vol. 59, pp. 6185-6191, (1999).
Wang, J., "Survey and Summary: From DNA biosensors to gene chips"., Nucleic Acids Research, vol. 28, No. 16, pp. 3011-3016, (2000).
Wang, K.Y., et al., "A DNA aptamer which binds to and inhibits thrombin exhibits a new structural motif for DNA"., Biochemistry, vol. 32, No. 8, pp. 1899-1904, (1993).
Wang, Y., et al., "Assembly and characterization of five-arm and six-arm DNA branched junctions"., Biochemistry, vol. 30, pp. 5667-5674, (1991).
Wang, Y., et al., "RNA molecules that specifically and stoichiometrically bind aminoglycoside antibiotics with high affinities"., Biochemistry, vol. 35, No. 38, pp. 12338-12346, (1996).
Wecker, M., et al., "In vitro selection of a novel catalytic RNA: characterization of a sulfer alkylation reaction and interaction with a small peptide"., RNA, vol. 2, pp. 982-994, (1996).
Wedekind, J.E., et al., "Crystal structure of a lead-dependent ribozyme revealing metal binding sites relevant to catalysis"., Nature Structural Biology, vol. 6, No. 3, pp. 261-268, (1999).
Wedekind, J.E., et al., "Crystal structure of the leadzyme at 1.8 Å Resolution: Metal ion binding and the implications for catalytic mechanism and allo site ion regulation"., Biochemistry, vol. 42, No. 32, pp. 9554-9563, (2003).
Wells, R.D., "Unusual DNA structures"., Journal of Biological Chemistry, vol. 263, No. 3, pp. 1095-1098, (1988).
Werstuck, G., et al., "Controlling gene expression in living cells through small molecule-RNA interactions"., Science, vol. 282, pp. 296-298, (1998).
Whaley, S.R., et al., "Selection of peptides with semiconductor binding specificity for directed nanocrystal assembly"., Nature, vol. 405, pp. 665-668, (2000).
Whitesides, G.M., et al., "Self-assembled monolayers and lithography"., Proceedings of the Robert A. Welch Foundation 39th Conference On Chemical Research on Nanophase Chemistry, pp. 109-121, Houston, TX, Oct. 23-24, 1995.
Wiegand, T.W., et al., "High-affinity oligonucleotide ligands to human IgE inhibit binding to Fc epsilon receptor I"., The Journal of Immunology, vol. 157, pp. 221-230, (1996).
Wiegand, T.W., et al., "Selection of RNA amide synthases"., Chemistry & Biology, vol. 4, No. 9, pp. 675-683, (1997).
Williams, K.P., et al., "Bioactive and nuclease-resistant L-DNA ligand of vasopressin"., Proc. Natl. Acad. Sci. USA, vol. 94, pp. 11285-11290, (1997).
Williams, K.P., et al., "Selection of novel $Mg^{2+}$-dependent self-cleaving ribozymes" The EMBO Journal, vol. 14, No. 18, pp. 4551-4557, (1995).
Wilson, C., et al., "Functional requirements for specific ligand recognition by a biotin-binding RNA Pseudoknot"., Biochemistry, vol. 37, No. 41, pp. 14410-14419, (1998).
Wilson, C., et al., "In vitro evolution of a self-alkylating ribozyme"., Nature, vol. 374, pp. 777-782, (1995).
Wilson, C., et al., "Isolation of a fluorophore-specific DNA aptamer with weak redox activity"., Chemistry & Biology, vol. 5, No. 11, pp. 609-617, (1998).
Wilson, D.S., et al., "In vitro selection of functional nucleic acids"., Annu. Rev. Biochem. vol. 68, pp. 611-647, (1999).
Winkler, J.D., et al., "Photodynamic Fluorescent Metal Ion Sensors with Parts per Billion Sensitivity"., J. Am. Chem. Soc., vol. 120, No. 13, pp. 3237-3242, (1998).
Wittmann, C., et al., "Microbial and Enzyme sensors for environmental monitoring"., Handbook of Biosensors and Electronic Noses: Medicine, Food, and the Environment, pp. 299-332, (1997).
Xia, P., et al., "Activation of Sphingosine Kinase by Tumor Necrosis Factor-α Inhibits Apoptosis in Human Endothelial Cells"., Journal of Biological Chemistry, vol. 274, No. 48, pp. 34499-34505, (1999).
Yan, H., et al., "DNA-Templated self-assembly of protein arrays and highly conductive nanowires"., Science, vol. 301, pp. 1882-1884, (2003).

Yang, Q., et al., "DNA ligands that bind tightly and selectively to cellobiose"., Proc. Natl. Acad. Sci. USA, vol. 95, pp. 5462-5467, (1998).
Yurke, B., et al., "A DNA-fuelled molecular machine made of DNA"., Nature, vol. 406, pp. 605-608, (2000).
Zhang, B., et al., "Peptide bond formation by in vitro selected ribozymes"., Nature, vol. 390, pp. 96-100, (1997).
Zhang, P., et al., "Design of a molecular beacon DNA probe with two fluorophores"., Angewandte Chemie International Edition, vol. 40, No. 2, pp. 402-405, (2001).
Zillmann, M., et al., "In vitro optimization of truncated stem-loop II variants of the hammerhead ribozyme for cleavage in low concentrations of magnesium under non-turnover conditions"., RNA, vol. 3, pp. 734-747, (1997).
Zimmerman, J.M., et al., "In vivo selection of spectinomycin-binding RNAs"., Nucleic Acids Research, vol. 30, No. 24, pp. 5425-5435, (2002).
Zimmermann, G.R., et al., "Molecular interactions and metal binding in the theophylline-binding core of an RNA aptamer"., RNA, vol. 6, pp. 659-667, (2000).
International Search Report dated Nov. 21, 2005 for corresponding PCT application No. PCT/US2005/001060.
Supplemental International Search Report dated Jan. 10, 2006 for corresponding PCT application No. PCT/US2005/001060.
Liu, J., et al., "Size control, metal substitution, and catalytic application of cryptomelane nanomaterials prepared using cross-linking reagents"., Chem. Mater., vol. 16, No. 2, pp. 276-285, (2004).
Abstract of: Iwasaki, K., Mizota, T., Kenkyu Hokoku- Kanagawa-ken Kogyo Shikensho 1991, 62, 57.
Storhoff, J.J., et al., "Facile colorimetric detection of polynucleotides based on gold nanoparticle probes"., Proceedings of the 1998 ERDEC Scientific Conference on Chemical and Biological Defense Research, Nov. 17-20, 1998, Aberdeen Proving Ground, pp. 221-226, (1999).
Yang, Y., et al., "Measurement of lead and magnesium in distilled spirits using inductively coupled plasma optical emission spectrometry viewed from the end"., Analytical Chemistry (Fenxi Huaxue), Chinese Journal of Analytical Chemistry, vol. 25, No. 9, pp. 1114-1117, (1997).
Cake, K.M., et al., "Partition of circulating lead between serum and red cells is different for internal and external sources of lead"., American Journal of Industrial Medicine, vol. 29, pp. 440-445, (1996).
International Search Report dated Aug. 31, 2004 for corresponding PCT application No. PCT/US2004/002946.
Hazarika, P., et al., "Reversible switching of DNA-Gold nanoparticle aggregation"., Angewandte Chemie International Edition, vol. 43, No. 47, pp. 6469-6471, (2004).
International Search Report dated May 29, 2006 for PCT application No. PCT/US2005/037896 (related application).
Liu, J., et al., "Improving fluorescent DNAzyme biosensors by combining Inter- and Intramolecular quenchers"., Analytical Chemistry, vol. 75, No. 23, pp. 6666-6672, (2003).
Liu, J., et al., "Stimuli-responsive disassembly of nanoparticle aggregates for light-up colorimetric sensing"., Journal of the American Chemical Society, vol. 127, No. 36, pp. 12677-12683, (2005).
European Search Report dated Jul. 10, 2006 for PCT application No. PCT/US2003/12576.
Tanner, F.C., et al., "Transfection of human endothelial cells"., Cardiovascular Research, vol. 35, pp. 522-528, (1997).
International Search Report dated Nov. 17, 2006 for PCT application No. PCT/US2006/001627.
Liu, J., et al., "DNAzyme-directed assembly of gold nanoparticles as colorimetric sensor for a broad range of analytes", pp. 1-3, located at http://ieeenano2003.arc.nasa.gov/THM@.pdf, (2003).
Wang, D.Y., et al., "A general approach for the use of oligonucleotide effectors to regulate the catalysis of RNA-cleaving ribozymes and DNAzymes", Nucleic Acids Research, vol. 30, No. 8, pp. 1735-1742, (2002).
Levy, M., et al., "Exponential growth by cross-catalytic cleavage of deoxyribozymogens",PNAS, vol. 100, No. 11, pp. 6416-6421, (2003).

Beyer, S., et al., "A modular DNA signal translator for the controlled release of a protein by an aptamer", Nucleic Acids Research, vol. 34, No. 5, pp. 1581-1587, (2006).

Frauendorf, C., et al., "Detection of small organic analytes by fluorescing molecular switches", Bioorganic & Medicinal Chemistry, vol. 9, pp. 2521-2524, (2001).

Glynou, K., et al., "Oligonucleotide-functionalized gold nanoparticles as probes in a dry-reagent strip biosensor for DNA analysis by hybridization", Anal. Chem, vol. 75, No. 16, pp. 4155-4160, (2003).

Liu, J., et al., "Optimization of a $Pb^{2+}$-directed gold nanoparticle/DNAzyme assembly and its application as a colorimetric biosensor for $Pb^{2+}$", Chem. Mater., vol. 16, No. 17, pp. 3231-3238, (2004).

Jones, K.D., et al., "Anniversary Essays, 3. Assay development, Changes in the development of rapid assays since 1995", Medical Devicelink, found at: http://www.devicelink.com/ivdt/archive/05/04/005.html, 3 pages, (2005).

Product Description: Pall Corporation, "Immunochromatographic, lateral flow or strip tests development ideas", found at: http://www.pall.com/34445_4154.asp, 7 pages, (1998).

Liu, J., et al., "Fast colorimetric sensing of adenosine and cocaine based on a general sensor design involving aptamers and nanoparticles", Angew. Chem. Int. Ed., vol. 45, pp. 90-94, (2006).

Liu, J., et al., "A simple and sensitive "dipstick" test in serum based on lateral flow separation of aptamer-linked nanostructures", Angewandte Chemie International Edition, vol. 45, pp. 7955-7959, (2006).

Jiang, P. et al., "Fluorescent detection of zinc in biological systems: recent development on the design of chemosensors and biosensors", Coordination Chemistry Reviews, vol. 248, pp. 205-229, (2004).

Lim, M.H. et al., "Metal-based turn-on fluorescent probes for sensing nitric oxide", Accounts of Chemical Research, vol. 40, No. 1, pp. 41-51, (2007).

Yoon, S. et al., "Screening mercury levels in fish with a selective fluorescent chemosensor", Journal of the American Chemical Society, vol. 127, pp. 16030-16031, (2005).

Yang, L. et al., "Imaging of the intracellular topography of copper with a fluorescent sensor and by synchrotron x-ray fluorescence microscopy", Proceedings of the National Academy of Science, vol. 102, no. 32, pp. 11179-11184, (2005).

He, Q. et al., "A selective fluorescent sensor for detecting lead in living cells", Journal of the American Chemical Society, vol. 128, pp. 9316-9317, (2006).

Zeng, L. et al., "A selective turn-on fluorescent sensor for imaging copper in living cells", Journal of the American Chemical Society, vol. 128, pp. 10-11, (2006).

Wegner, S.V. et al., "Design of an emission ratiometric biosensor from MerR family proteins: A sensitive and selective sensor for $Hg2+$", Journal of the American Chemical Society, vol. 129, pp. 3474-3475, (2007).

Nolan, E.M. et al., "Turn-on and ratiometric mercury sensing in water with a red-emitting probe", Journal of the American Chemical Society, vol. 129, pp. 5910-5918, (2007).

Sasaki, D.Y. et al., "Metal-induced dispersion of lipid aggregates: A simple, selective, and sensitive fluorescent metal ion sensor", Angew. Chem. Int. Ed. England, vol. 34, No. 8, pp. 905-907, (1995).

Torrado, A. et al., "Exploiting polypeptide motifs for the design of selective Cu(II) ion chemosensor" Journal of the American Chemical Society, vol. 120, pp. 609-610, (1998).

Grandini, P. et al., "Exploiting the self-assembly strategy for the design of selective CuII ion chemosensors", Angew. Chem. Int. Ed, vol. 38, No. 20, pp. 3061-3064, (1999).

Klein, G. et al., "A fluorescent metal sensor based on macrocyclic chelation", Chem. Comm., pp. 561-562, (2001).

Zheng, Y. et al., "A new fluorescent chemosensor for copper ions based on tripeptide glycyl-histidyl-lysine (GHK)", Organic Letters, vol. 3, No. 21, pp. 3277-3280, (2001).

Boiocchi, M. et al., " A two-channel molecular dosimeter for the optical detection of copper(II)" Chem. Comm, pp. 1812-1813, (2003).

Zheng, Y. et al., "Peptidyl fluorescent chemsensors for the detection of divalent copper", Analytical Chemistry, vol. 75, No. 7, pp. 1706-1712, (2003).

Zheng, Y. et al., "Development of fluorescent film sensors for the detection of divalent copper", Journal of the American Chemical Society, vol. 125, pp. 2680-2686, (2003).

Roy, B.C. et al., "Synthesis of new, pyrene-containing metal-chelating lipids and sensing of cupric ions", Organic Letters, vol. 5, No. 1, pp. 11-14, (2003).

Kaur, S. et al., "Photoactive chemosensors 4: a $Cu2+$ protein cavity mimicking fluorescent chemosensor for selective $Cu2+$ recognition", Tetrahedron Letters, vol. 45, pp. 5081-5085, (2004).

Mei, Y. et al., "A selective and sensitive chemosensor for $Cu2+$ based on 8-hydroxyquinoline", Tetrahedron Letters, vol. 47, pp. 2447-2449, (2006).

Zhang, X-B. et al., "A highly selective fluorescent sensor for $Cu2+$ based on 2-(2'-hydroxyphenyl) benzoxazole in a poly(vinyl chloride) matrix", Analytica Chimica Acta, vol. 567, pp. 189-195, (2006).

Comba, P. et al., "Synthesis of new phenanthroline-based heteroditopic ligands—highly efficient and selective fluorescence sensors for copper (II) ions", European Journal of Inorganic Chemistry, pp. 4442-4448, (2006).

Kim, S. H. et al., "$Hg2+$-selective off-on and $Cu2+$-selective on-off type fluoroionophore based upon cyclam", Organic Letters, vol. 8, No. 3, pp. 371-374, (2006).

White, B. R. et al., "Fluorescent peptide sensor for the selective detection of $Cu2+$", Talanta, vol. 71, pp. 2015-2020, (2007).

Oter, O. et al., "Spectral characterization of a newly synthesized fluorescent semicarbazone derivative and its usage as a selective fiber optic sensor for copper(II)", Analytica Chimica Acta, vol. 584, pp. 308-314, (2007).

Dujols, V. et al., "A long-wavelength fluorescent chemodosimeter selective for Cu(II) ion in water", Journal of the American Chemical Society, vol. 119, pp. 7386-7387, (1997).

Yang, J-S. et al., "$Cu2+$-induced blue shift of the pyrene excimer emission: a new signal transduction mode of pyrene probes", Organic Letters, vol. 3, No. 6, pp. 889-892, (2001).

Kaur, S. et al., "Photoactive chemosensors 3: a unique case of fluorescence enhancement with Cu(II)", Chem. Comm., pp. 2840-2841, (2002).

Wu, Q. et al., "Catalytic signal amplification using a heck reaction. An example in the fluorescence sensing of Cu(II)", Journal of the American Chemical Society, vol. 126, pp. 14682-14683, (2004).

Royzen, M. et al., "Ratiometric displacement approach to Cu(II) sensing by fluorescence", Journal of the American Chemical Society, vol. 127, pp. 1612-1613, (2005).

Xu, Z. et al., "Ratiometric and selective fluorescent sensor for CuII based on internal charge transfer (ICT)", Organic Letters, vol. 7, No. 5, pp. 889-892, (2005).

Wen, Z-C. et al., "A highly selective charge transfer fluoroionophore for $Cu2+$", Chem. Commun., pp. 106-108, (2006).

Yang, H. et al., "Highly selective ratiometric fluorescent sensor for Cu(II) with two urea groups", Tetrahedron Letters, vol. 47, pp. 2911-2914, (2006).

Martinez, R. et al., "2-aza-1,3-butadiene derivatives featuring an anthracene or pyrene unit: highly selective colorimetric and fluorescent signaling of $Cu2+$ cation", Organic Letters, vol. 8, No. 15, pp. 3235-3238, (2006).

Navani, N.K. et al., "Nucleic acid aptamers and enzymes as sensors", Current Opinion in Chemical Biology, vol. 10, pp. 272-281, (2006).

Liu, J. et al., "A catalytic beacon sensor for uranium with parts-per-trillion sensitivity and millionfold selectivity", Proceedings of the National Academy of Science, vol. 104, No. 7, pp. 2056-2061, (2007).

Georgopoulos, P.G. et al., "Environmental copper: its dynamics and human exposure issues", Journal of Toxicology and Environmental Health, Part B, vol. 4, pp. 341-394, (2001).

Hetzberg, R.P. et al., "Cleavage of DNA with methidiumpropyl-EDTA-iron(II): reaction conditions and product analyses", Biochemistry, vol. 23, pp. 3934-3945, (1984).

Yazzie, M. et al., "Uranyl acetate causes DNA single strand breaks in vitro in the presence of ascorbate (Vitamin C)", Chem. Res. Toxicol., vol. 16, pp. 524-530, (2003).

Bolletta, F. et al., "A [RuII (bipy)3]-[1,9-diamino-3,7-diazanonane-4,6-dione] two-component system as an efficient on-off luminescent chemosensor for $Ni2+$ and $Cu2+$ in water, based on an ET (energy transfer) mechanism", Journal of the Chemical Society, Dalton Transactions, pp. 1381-1385, (1999).

Carmi, N. et al., "Characterization of a DNA-cleaving deoxyribozyme", Bioorganic & Medicinal Chemistry, vol. 9, issue 10, pp. 2589-2600, (2001).

Liu, J. et al., "A DNAzyme catalytic beacon sensor for paramagnetic Cu2+ ions in aqueous solution with high sensitivity and selectivity", Journal of the American Chemical Society, 2 pages, (2007), ASAP Web Release Date: Jul. 24, 2007.

Tanaka, K. et al., "Programmable self-assembly of metal ions inside artificial DNA duplexes", Nature Nanotechnology, vol. 1, pp. 190-194, (2006).

Achenbach, J.C. et al., "DNAzymes: From creation in vitro to application in vivo", Current Pharmaceutical Biotechnology, vol. 5, pp. 321-336, (2004).

Balaji, T. et al., "Optical sensor for the visual detection of mercury using mesoporous silica anchoring porphyrin moiety", The Analyst, vol. 130, pp. 1162-1167, (2005).

Caballero, A. et al., "Highly selective chromogenic and redox or fluorescent sensors of Hg2+ in aqueous environment based on 1,4-disubstituted azines", Journal of the American Chemical Society, vol. 127, pp. 15666-15667, (2005).

Chan, W.H. et al., "Development of a mercury ion-selective optical sensor based on fluorescence quenching of 5,10,15,20-tetraphenylporphyrin", Analytica Chimica Acta, vol. 444, pp. 261-269, (2001).

Chen, P. et al., "A general strategy to convert the merR family proteins into highly sensitive and selective fluorescent biosensors for metal ions", Journal of the American Chemical Society, vol. 126, pp. 728-729, (2004).

Chiuman, W. et al., "Efficient signaling platforms built from a small catalytic DNA and doubly labeled fluorogenic substrates", Nucleic Acids Research, vol. 35, No. 2, pp. 401-405, (2007).

Cruz, R.P.G. et al., "Dinucleotide junction cleavage versatility of 8-17 deoxyribozyme", Chemistry & Biology, vol. 11, pp. 57-67, (2004).

Frasco, M.F. et al., "Mechanisms of cholinesterase inhibition by inorganic mercury", the FEBS Journal, vol. 274, pp. 1849-1861, (2007).

Guo, X. et al., "A highly selective and sensitive fluorescent chemosensor for Hg2+ in neutral buffer aqueous solution", The Jouranl of the American Chemical Society, vol. 126, pp. 2272-2273, (2004).

Harris, H.H. et al., "The chemical form of mercury in fish", Science, vol. 301, pp. 1203, (2003).

Ha-Thi, M-H. et al., "Highly selective and sensitive phosphane sulfide derivative for the detection of Hg2+ in an organoaqueous medium", Organic Letters, vol. 9, No. 6, pp. 1133-1136, (2007).

Joyce, G.F. et al., "Directed evolution of nucleic acid enzymes", Annual Review Biochem., vol. 73, pp. 791-836, (2004).

Ko, S-K. et al., "In vivo monitoring of mercury ions using a rhodamine-based molecular probe", Journal of the American Chemical Society, vol. 128, pp. 14150-14155, (2006).

Kuswandi, B. et al., "Capillary optode: determination of mercury(II) in aqueous solution", Analytical Letters, vol. 32, No. 9. 4, pp. 649-664, (1999).

Kuswandi, B. et al., "Selective pool optode for mercury ion sensing in aqueous solution", Sensors and Actuators B, vol. 74, pp. 131-137, (2001).

Lee, J-S. et al., "Colorimetric detection of mercuric ion (Hg2+) in aqueous media using DNA-functionalized gold nanoparticles", Angewandte Chemie International Edition, vol. 46, pp. 4093-4096, (2007).

Liu, B. et al., "A selective fluorescent ratiometric chemodosimeter for mercury ion", Chem. Communications, pp. 3156-3158, (2005).

Liu, J. et al., "Fluorescent DNAzyme biosensors for metal ions based on catalytic molecular beacons", Methods in Molecular Biology, vol. 335, pp. 275-288, (2006).

Matsushita, M. et al., "A blue fluorescent antibody-cofactor sensor for mercury", Organic Letters, vol. 7, No. 22, pp. 4943-4946, (2005).

Miyake, Y. et al., "MercuryII-mediated formation of thymine-HgII-thymine base pairs in DNA duplexes", Journal of the American Chemical Society, vol. 128, No. 7, pp. 2172-2173, (2006).

Nolan, E.M. et al., "A "turn-on" fluorescent sensor for the selective detection of mercuric ion in aqueous media", Journal of the American Chemical Society, vol. 125, pp. 14270-14271, (2003).

Ono, A. et al., "highly selective oligonucleotide-based sensor for mercury (II) in aqueous solutions", Angew. Chem. Int. Ed., vol. 43, pp. 4300-4302, (2004).

Ostatna, V. et al., "Self-assembled monolayers of thiol-end-labeled DNA at mercury electrodes", Langmuir, vol. 22, pp. 6481-6484, (2006).

Prodi, L. et al., "An effective fluorescent achemosensor for mercury ions", Journal of the American Chemical Society, vol. 122, No. 28, pp. 6769-6770, (2000).

Silverman, S.K., "Survey and Summary: In vitro selection, characterization, and application of deoxyribozymes that cleave RNA", Nucleic Acids Research, vol. 33, No. 19, pp. 6151-6163, (2005).

Song, K.C. et al., "Fluorogenic Hg2+-selective chemodosimeter derived from 8-hydroxyquinoline", Organic Letters, vol. 8, No. 16, pp. 3413-3416, (2006).

Szurdoki, F. et al., "A combinatorial approach to discover new chelators for optical metal ion sensing", Analytical Chemistry, vol. 72, No. 21, pp. 5250-5257, (2000).

Tanaka, Y. et al., "15N-15N J-coupling across HgII: Direct observation of HgII-mediated T-T base pairs in a DNA duplex" Journal of the American Chemical Society, vol. 129, No. 2, pp. 244-245, (2007).

Jacoby, M. "Mercury Sensor—Analytical Chemistry: Colorimetric method is sensitive and selective", Chemical & Engineering News, pp. 15, May 7, 2007.

Vannela, R. et al., "In vitro selection of Hg (II) and as (V)-dependent RNA-cleaving DNAzymes", Environmental Engineering Science, vol. 24, No. 1, pp. 73-84, (2007).

Vaughan, A.A. et al., "Optical fibre reflectance sensors for the detection of heavy metal ions based on immobilized Br-PADAP", Snesors and Actuators B, vol. 51, pp. 368-376, (1998).

Virta, M. et al., "A luminescence-based mercury biosensor", Analytical Chemistry, vol. 67, No. 3, pp. 667-669, (1995).

Wang, J. et al., "Detecting Hg2+ ions with an ICT fluorescent sensor molecule: Remarkable emission spectra shift and unique selectivity", Journal of Organic Chemistry, vol. 71, pp. 4308-4311, (2006).

Wang, J. et al., "A series of polyamide receptor based PET fluorescent sensor molecules: Positively cooperative Hg2+ ion binding with high sensitivity", Organic Letters, vol. 8, No. 17, pp. 3721-3724, (2006).

Widmann, A. et al., "Mercury detection in seawater using a mercaptoacetic acid modified gold microwire electrode", Electroanalysis, vol. 17, No. 10, pp. 825-831, (2005).

Xiao, Y. et al., "Electrochemical detection of parts-per-billion lead via an electrode-bound DNAzyme assembly", Journal of the American Chemical Society, vol. 129, pp. 262-263, (2007).

Yang, W. et al., "Solid phase extraction and spectrophotometric determination of mercury in tobacco and tobacco additives with 5-(p-aminobenzylidene)-thiothiorhodanine", Journal of the Brazilian Chemical Society, vol. 17, No. 5, pp. 1039-1044, (2006).

Yang, Y-K. et al., "A rhodamine-based fluorescent and colorimetric chemodosimeter for the rapid detection of Hg2+ ions in aqueous media", Journal of the American Chemical Society, vol. 127, pp. 16760-16761, (2005).

Zhang, X-B. et al "An optical fiber chemical sensor for mercury ions based on a porphyrin dimmer", Analytical Chemistry, vol. 74, No. 4, pp. 821-825, (2002).

Zhao, Y. et al., "A "turn-on" fluorescent sensor for selective Hg(II) detection in aqueous media based on metal-induced dye formation", Inorganic Chemistry, vol. 45, No. 25, pp. 10013-10015, (2006).

Zhao, Y. et al., "Tuning the sensitivity of a foldamer-based mercury sensor by its folding energy", Journal of the American Chemical Society, vol. 128, No. 31, pp. 9988-9989, (2006).

Zhao, Y. et al., "Detection of Hg2+ in aqueous solutions with a foldamer-based fluorescent sensor modulated by surgactant micelles", Organic Letters, vol. 8, No. 21, pp. 4715-4717, (2006).

Zuker, M., "Mfold web server for nucleic acid folding and hybridization prediction", Nucleic Acids Research, vol. 31, No. 13, pp. 3406-3415, (2003).

International Search Report dated May 10, 2007 for PCT application No. PCT/US2006/030617.

Liu, J. et al., "Adenosine-dependent assembly of aptazyme-functionalized gold nanoparticles and its application as a colorimetric biosensor", Analytical Chemistry, vol. 76, No. 6, pp. 1627-1632, (2004).

Liu, J. et al., "Smart nanomaterials responsive to multiple chemical stimuli with controllable cooperativity", Advanced Materials, vol. 18, No. 13, pp. 1667-1671, (2006).

Nutiu, R. et al., "Signaling aptamers for monitoring enzymatic activity and for inhibitor screening", Chembiochem—A European Journal of Chemical Biology, vol. 5, No. 8, pp. 1139-1144, (2004).

Nutiu, R. et al., "Structure-switching signaling aptamers: Transducing molecular recognition into fluorescence signaling", Chemistry—A European Journal, vol. 10, No. 8, pp. 1868-1876, (2004).

International Search Report dated Jul. 31, 2007 for PCT application No. PCT/US2007/064055.

Ahern, H., "Biochemical, reagent kits offer scientists good return on investment", The Scientist, vol. 9, No. 15, pp. 20-22, (1995).

Homann, M. et al., "Dissociation of long-chain duplex RNA can occur via strand displacement in vitro: biological implication", Nucleic Acids Research, vol. 24, No. 22, pp. 4395-4400, (1996).

Alivisatos, A.P. et al., "Quantum dots as cellular probes", Annual Review Biomed. Eng, vol. 7, pp. 55-76, (2005).

Dyadyusha, L. et al., "Quenching of CdSe quantum dot emission, a new approach for biosensing", Chemical Communication, pp. 3201-3203, (2005).

Ellington, A.D. et al., "In vitro selection of RNA molecules that bind specific ligands", Nature, vol. 346, pp. 818-822, (1990).

Gerion, D. et al., "Room-temperature single-nucleotide polymorphism and multiallele DNA detection using fluorescent nanocrystals and microarrays", Analytical Chemistry, vol. 75, No. 18, pp. 4766-4772, (2003).

Goldman, E.R. et al., "Multiplexed toxin analysis using four colors of quantum dot fluororeagents", Analytical Chemistry, vol. 76, No. 3, pp. 684-688, (2004).

Gueroui, Z. et al., "Single-molecule measurements of gold-quenched quantum dots", Physical Review Letters, vol. 93, No. 16, pp. 166108/1-166108/4, (2004).

Han, M. et al., "Quantum-dot-tagged microbeads for multiplexed optical coding of biomolecules", Nature Biotechnology, vol. 19, pp. 631-635, (2001).

Hansen, J.A. et al., "Quantum-dot/Aptamer-based ultrasensitive multi-analyte electrochemical biosensor", Journal of the American Chemical Society, vol. 128, No. 7, pp. 2228-2229, (2006).

Hartig, J.S. et al., "Protein-dependent ribozymes report molecular interactions in real time", Nature Biotechnology, vol. 20, pp. 717-722, (2002).

Herman, T. et al., "Adaptive recognition by nucleic acid aptamers", Science, vol. 287, pp. 820-825, (2000).

Kurreck, J., "Antisense technologies Improvement through novel chemical modifications", Eur. J. Biochem, vol. 270, pp. 1628-1644, (2003).

Lee, J.F. et al., "Aptamer database", Nucleic Acids Research, vol. 32, Database Issue, pp. D95-D100, (2004).

Levy, M. et al., "Quantum-dot aptamer beacons for the detection of proteins", ChemBioChem, vol. 6, pp. 2163-2166, (2005).

Liu, J. et al., "Smart nanomaterials responsive to multiple chemical stimuli with controllable cooperativity", Advanced Materials, vol. 18, pp. 1667-1671, (2006).

Liu, J. et al., "Preparation of aptamer-linked gold nanoparticle purple aggregates for colorimetric sensing of analytes", Nature Protocols, vol. 1, No. 1, pp. 246-252, (2006).

Medintz, I.L. et al., "Quantum dot bioconjugates for imaging, labeling and sensing", Nature Materials, vol. 4, pp. 435-446, (2005).

Miduturu, C.V. et al., "Modulation of DNA constraints that control macromolecular folding", Angew. Chem. Int. Ed., vol. 45, pp. 1918-1921, (2006).

Mitchell, G.P. et al., "Programmed assembly of DNA functionalized quantum dots", Journal of the American Chemical Society, vol. 121, No. 35, pp. 8122-8123, (1999).

Nutiu, R. et al., "Structure-switching signaling aptamers: Transducing molecular recognition into fluorescence signaling", Chem. Eur. J., vol. 10, pp. 1868-1876, (2004).

Oh, E. et al., "Inhibition assay of biomolecules based on fluorescence resonance energy transfer (FRET) between quantum dots and gold nanoparticles", Journal of the American Chemical Society, vol. 127, No. 10, pp. 3270-3271, (2005).

Rajendran, M. et al., "In vitro selection of molecular beacons", Nucleic Acids Research, vol. 31, No. 19, pp. 5700-5713, (2003).

Vet, J.A.M. et al., "Multiplex detection of four pathogenic retroviruses using molecular beacons", Proceedings of the National Academy of Science, USA., vol. 96, pp. 6394-6399, (1999).

Wargnier, R. et al., "Energy transfer in aqueous solutions of oppositely charged CdSe/ZnS core/shell quantum dot-nanogold assemblies", Nano Letters, vol. 4, No. 3, pp. 451-457, (2004).

Wilson, R. et al., "Encoded microcarriers for high-throughput multiplexed detection", Angewandte Chemie International Edition, vol. 45, pp. 6104-6117, (2006).

Winkler, W.C. et al., "Regulation of bacterial gene expression by riboswitches", The Annual Review of Microbiology, vol. 59, pp. 487-517, (2005).

Yang, C.J. et al., "Light-switching excimer probes for rapid protein monitoring in complex biological fluids", PNAS, vol. 102, No. 48, pp. 17278-17283, (2005).

Liu, J. et al., "Quantum dot encoding of aptamer-linked nanostructures for one-pot simultaneous detection of multiple analytes", Analytical Chemistry, vol. 79, No. 11, pp. 4120-4125, (2007).

Lu, Y. et al., "Smart nanomaterials inspired by biology: Dynamic assembly of error-free nanomaterials in response to multiple chemical and biological stimuli", Accounts of Chemical Research, vol. 40, No. 5, pp. 315-323, (2007).

Allen, M.J. et al., "Magnetic resonance contrast agents for medical and molecular imaging", Met. Ions Biol. Syst., vol. 42, pp. 1-38, (2004).

Artemov, D. et al., "MR molecular imaging of the Her-2/neu receptor in breast cancer cells using targeted iron oxide nanoparticles", Magnetic Resonance in Medicine, vol. 49, pp. 403-408, (2003).

Buerger, C. et al., "Sequence-specific peptide aptamers, interacting with the intracellular domain of the epidermal growth factor receptor, interfere with stat3 activation and inhibit the growth of tumor cells", The Journal of Biological Chemistry, vol. 278, No. 39, pp. 37610-37621, (2003).

Buerger, C. et al., "Bifunctional recombinant proteins in cancer therapy: cell penetrating peptide aptamers as inhibitors of growth factor signaling", J. Cancer Research Clin. Oncol., vol. 129, pp. 669-675, (2003).

Carr, D.H. et al., "Gadolinium-DTPA as a contrast agent in MRI: initial clinical experience in 20 patients", American Journal of Roentfenol., vol. 143, pp. 215-224, (1984).

Chen, Y. et al., "An autonomous DNA nanomotor powered by a DNA enzyme", Angew. Chem. Int. Ed., vol. 43, pp. 3554-3557, (2004).

Corot, C. et al., "Macrophage imaging in central nervous system and in carotid atherosclerotic plaque using ultrasmall superparamagnetic iron oxide in magnetic resonance imaging", Investigative Radiology, vol. 39, No. 10, pp. 619-625, (2004).

Dodd, C.H. et al., "Normal T-cell response and in vivo magnetic resonance imaging of T cells loaded with HIV transactivator-peptide-derived superparamagnetic nanoparticles", Journal of Immunological Methods, vol. 256, pp. 89-105, (2001).

Drolet, D.W. et al., "An enzyme-linked oligonucleotide assay", Nature Biotechnology, vol. 14, pp. 1021-1025, (1996).

Enochs, W.S. et al., "Improved delineation of human brain tumors on MR images using a long-circulating, superparamagnetic iron oxide agent", Journal of Magnetic Resonance Imaging, vol. 9, pp. 228-232, (1999).

Famulok, M. et al., "Nucleic acid aptamers-from selection in vitro to applications in vivo", Accounts of Chemical research, vol. 33, No. 9, pp. 591-599, (2000).

Fang, X. et al., "Molecular aptamer for real-time oncoprotein platelet-derived growth factor monitoring by fluorescence anisotropy", Analytical Chemistry, vol. 73, No. 23, pp. 5752-5757, (2001).

Frullano, L. et al., "Synthesis and characterization of a doxorubicin-Gd(III) contrast agent conjugate: A new approach toward prodrug-procontrast complexes", Inorganic Chemistry, vol. 45, No. 21, pp. 8489-8491, (2006).

Hamaguchi, N. et al., "Aptamer beacons for the direct detection of proteins", Analytical Biochemistry, vol. 294, pp. 126-131, (2001).

Harisinghani, M.G. et al., "Noninvasive detection of clinically occult lymph-node metastases in prostate cancer", The New England Journal of Medicine, vol. 348, No. 25, pp. 2491-2499, (2003).

Hermann, T. et al., "Adaptive recognition by nucleic acid aptamers", Science, vol. 287, pp. 820-825, (2000).

Hoppe-Seyler, F. et al., "Peptide aptamers: Specific inhibitors of protein function", Current Molecular Medicine, vol. 4, pp. 529-538, (2004).

Huang, C-C. et al., "Aptamer-modified gold nanoparticles for colorimetric determination of platelet-derived growth factors and their receptors", Analytical Chemistry, vol. 77, No. 17, pp. 5735-5741, (2005).

Josephson, L. et al., "High-efficiency intracellular magnetic labeling with novel superparamagnetic-tat peptide conjugates", Bioconjugate Chem., vol. 10, No. 2, pp. 186-191, (1999).

Josephson, L. et al., "The effects of iron oxides on proton relaxivity", Magnetic Resonance Imaging, vol. 6, pp. 647-653, (1988).

Josephson, L. et al., "Magnetic nanosensors for the detection of oligonucleotide sequences", Angew. Chem. Int. Ed., vol. 40, No. 17, pp. 3204-3206, (2001).

Kabalka, G. et al., "Gadolinium-labeled liposomes: Targeted MR contrast agents for the liver and spleen", Radiology, vol. 163, pp. 255-258, (1987).

Kooi, M.E. et al., "Accumulation of ultrasmall superparamagnetic particles of iron oxide in human atherosclerotic plaques can be detected by in vivo magnetic resonance imaging", Circulation, vol. 107, pp. 2453-2458, (2003).

Kresse, M. et al., "Targeting of ultrasmall superparamagnetic iron oxide (USPIO) particles to tumor cells in vivo by using transferring receptor pathways", Magn. Reson. Med., vol. 40, pp. 236-242, (1998).

Lee, J. et al., "A steroid-conjugated contrast agent for magnetic resonance imaging of cell signaling", Journal of American Chemical Society, vol. 127, No. 38, pp. 13164-13166, (2005).

Lewin, M. et al., "Tat peptide-derivatized magnetic nanoparticles allow in vivo tracking and recovery of progenitor cells", Nature Biotechnology, vol. 18, pp. 410-414, (2000).

Li, J.J. et al., "Molecular aptamer beacons for real-time protein recognition", Biochemical and Biophysical Research Communications, vol. 292, No. 1, pp. 31-40, (2002).

Li, W-H. et al., "A calcium-sensitive magnetic resonance imaging contrast agent", Journal of the American Chemical Society, vol. 121, No. 6, pp. 1413-1414, (1999).

Lin, C.H. et al., "Structural basis of DNA folding and recognition in an AMP-DNA aptamer complex: distinct architectures but common recognition motifs for DNA and RNA aptamers complexed to AMP", Chemistry and Biology, vol. 4, pp. 817-832, (1997).

Liss, M. et al., "An aptamer-based quartz crystal protein biosensor", Analytical Chemistry, vol. 74, No. 17, pp. 4488-4495, (2002).

Liu, Y. et al., "Aptamer-directed self-assembly of protein arrays on a DNA nanostructure", Angew. Chem. Int. Ed., vol. 44, pp. 4333-4338, (2005).

Macaya, R.F. et al., "Thrombin-binding DNA aptamer forms a unimolecular quadruplex structure in solution", Proceedings of the National Academy of Science USA, vol. 90, pp. 3745-3749, (1993).

Nagel-Wolfrum, K. et al., "The interaction of specific peptide aptamers with the DNA binding domain and the dimerization domain of the transcription factor stat3 inhibits transactivation and induces apoptosis in tumor cells", Molecular Cancer Research, vol. 2, pp. 170-182, (2004).

Nitin, N. et al., "Functionalization and pepride-based delivery of magnetic nanoparticles as an intracellular MRI contrast agent", J. Biol. Inorg. Chem., vol. 9, pp. 706-712, (2004).

Nutiu, R. et al., "Engineering DNA aptamers and DNA enzymes with fluorescence-signaling properties", Pure Appl. Chem., vol. 76, Nos. 7-8, pp. 1547-1561, (2004).

Nutiu, R. et al., "Structure-switching signaling aptamers: Transducing molecular recognition into fluorescence signaling", Chem. Eur. J., vol. 10, pp. 1868-1876, (2004).

Padmanabhan, K. et al., "The structure of a-thrombin inhibited by a 15-mer single-stranded DNA aptamer", The Journal of Biological Chemistry, vol. 268, No. 24, pp. 17651-17654, (1993).

Pavlov, V. et al., "Aptamer-functionalized au nanoparticles for the amplified optical detection of thrombin", The Journal of the American Chemical Society, vol. 126, No. 38, pp. 11768-11769, (2004).

Pendergrast, P.S. et al., "Nucleic acid aptamers for target validation and therapeutic applications", Journal of Biomolecular Techniques, vol. 16, issue 3, pp. 224-234, (2005).

Perez, J.M. et al., "Use of magnetic nanoparticles as nanosensors to probe for molecular interactions", ChemBioChem, vol. 5, pp. 261-264, (2004).

Perez, J.M. et al., "Viral-induced self-assembly of magnetic nanoparticles allows the detection of viral particles in biological media", Journal of the American Chemical Society, vol. 125, No. 34, pp. 10192-10193, (2003).

Radi, A.E. et al., "Reagentless, reusable, ultrasensitive electrochemical molecular beacon aptasensor", Journal of the American Chemical Society, vol. 128, No. 1, pp. 117-124, (2006).

Saeed, M. et al., "Occlusive and reperfused myocardial infarcts: differentiation with Mn-DPDP-enhanced MR imaging", Radiology, vol. 172, pp. 59-64, (1989).

Shen, T. et al., "Monocrystalline iron oxide nanocompounds (MION): Physicochemical properties", Magn. Reson. Med., vol. 29, pp. 599-604, (1993).

Soriaga, M.P. et al., "Determination of the orientation of adsorbed molecules at solid-liquid interfaces by thin-layer electrochemistry: Aromatic compounds at platinum electrodes", Journal of the American Chemical Society, vol. 104, pp. 2735-2742, (1982).

Soriaga, M.P. et al., "Determination of the orientation of aromatic molecules adsorbed on platinum electrodes: The influence of iodide a surface-active anion", Journal of the American Chemical Society, vol. 104, pp. 2742-2747, (1982).

Soriaga, M.P. et al., "Determination of the orientation of aromatic molecules adsorbed on platinum electrodes: The effect of solute concentration", Journal of the American Chemical Society, vol. 104, pp. 3937-3945, (1982).

Sosnovik, D.E. et al., "Emerging concepts in molecular MRI", Current Opinion in Biotechnology, vol. 18, pp. 4-10, (2007).

Taboada, E. et al., "Relaometric and magnetic characterization of ultrasmall iron oxide nanoparticles with high magnetization. Evaluation as potential T1 magnetic resonance imaging contrast agents for molecular imaging", Langmuir, vol. 23, No. 8, pp. 4583-4588, (2007).

Tasset, D.M. et al., "Oligonucleotide inhibitors of human thrombin that bind distinct epitopes", J. Mol. Biol., vol. 272, pp. 688-698, (1997).

Tian, Y. et al., "DNAzyme amplification of molecular beacon signal", Talanta, vol. 67, pp. 532-537, (2005).

Tompkins, H.G. et al., "The study of the gas-solid interaction of acetic acid with a cuprous oxide surface using reflection-absorption spectroscopy", Journal of colloid and interface science, vol. 49, No. 3, pp. 410-421, (1974).

Tsourkas, A. et al., "Magnetic relaxation switch immunosensors detect enantiomeric impurities", Angew. Chem. Int. Ed., vol. 43, pp. 2395-2399, (2004).

Wang, S. et al., "Core/shell quantum dots with high relaxivity and photoluminescence for multimodality imaging", Journal of the American Chemical Society, vol. 129, No. 13, pp. 3848-3856, (2007).

Weissleder, R. et al., "MR imaging of splenic metastases: Ferrite-enhanced detection in rats", American Journal Roentgenol., vol. 149, pp. 723-726, (1987).

Xiao, Y. et al., "Label-free electronic detection of thrombin in blood serum by using an aptamer-based sensor", Angew. Chem. Int. Ed., vol. 44, pp. 5456-5459, (2005).

Xiao, Y. et al., "A reagentless signal-on architecture for electronic, aptamer-based sensors via target-induced strand displacement", Journal of the American Chemical Society, vol. 127, No. 51, pp. 17990-17991, (2005).

Xu, D. et al., "Label-free electrochemical detection for aptamer-based array electrodes", Analytical Chemistry, vol. 77, No. 16, pp. 6218-6224, (2005).

Yamamoto, R. et al., "Molecular beacon aptamer fluoresces in the presence of Tat protein of HIV-1", Genes to Cells, vol. 5, pp. 389-396, (2000).

Zhao, M. et al., "Magnetic sensors for protease assays", Angew. Chem. Int. Ed., vol. 42, No. 12, pp. 1375-1378, (2003).

Zhao, M. et al., "Differential conjugation of tat peptide to superparamagnetic nanoparticles and its effect on cellular uptake", Bioconjugate Chem., vol. 13, pp. 840-844, (2002).

Liu, J. et al., "Colorimetric $Cu^{2+}$ detection with a ligation DNAzyme and nanoparticles", Chemical Communications, Advance Articles, DOI: 10.1039/b712421j, 6 pages, Oct. 24, 2007.

Liu, J. et al., "Non-Base pairing DNA provides a new dimension for controlling aptamer-linked nanoparticles and sensors", Journal of the American Chemical Society, vol. 129, No. 27, pp. 8634-8643, (2007).

Liu, J. et al., Supporting Information for "Colorimetric $Cu^{2+}$ detection with a ligation DNAzyme and nanoparticles", Chemical Communications, Advance Articles, 4 pages, Oct. 24, 2007.

Stratagene Catolog, "Gene Characterization Kits", 2 pages, (1988).

Fahlman, R.P. et al., "DNA conformational switches as sensitive electronic sensors of analytes", Journal of the American Chemical Society, vol. 124, 4610-4616, (2002).

* cited by examiner

```
Zn-DNA

5'- CTGCAGAATTCTAATACGACTCACTATAGGAAGAGATGGCGAC

Class I (used for reselection)
#5,6,7,9,21,25,29,43,47
      ATCTC TTTTGTCAGCGACTCGAAATAGTGTGTTGAAGCAGCTCTA GTGAC Class II
2,10,17,20,24,31,37,39
      AGCCA -TAGTTCTACCAGCGGTTCGAAATAGTGAAGTGTTCGTGA CTATC
#3    GGCCA -TAGTTCTACCAGCGGTTCGAAATAGTGAAATGTTCGTGA CTATC
4    GCCAGATTAGTTCTACCAGCGGTTCGAAATAGTGAAATGTTCGTGA CTATC Class III
15,18,19,34,35,38,50
      ATCTC CAAAGATGCCAGCATGCTATTCTCCGAGCCGGTCGAAATA GTGAC
14   ATCTC CAAAGATGCCTGCATGCTATTCTCCGAGCCGGTCGAAATA GTGAC Unclassified
36   ATCTC GTCTCCGAGCCGGTCGAAATAGTCAGGTGTTTCTATTCGG GTGAC
#40   ATCAC CTTCTCCGAGCCGGTCGAAATAGTAGTTTTTAGTATATCT GTGAC
#42   ATCTC AGGTGTTGGCTGCTCTCGCGGTGGCGAGAGGTAGGGTGAT GTGAC

GGTAAGCTTGGCAC-3'
```

FIG. 2

Co-DNA

5'-CTGCAGAATTCTAATACGACGCACTATAGGAAGAGATCGCGAC

Class I (used for reselection)
18,15,34
```
        ATCTC TTGTATTAGCTACACTGTTAGTGGATCGGGTCTAATCTCG  GTGAC
#1      GTCTC TTGTATTAGCTACACTGTTAGTGGATCGGGTCTAATCTCG  GTGAC
#25     ATCTC CTGTATTAGCTACACTGTTAGTGGATCGGGTCTAATCTCG  GTGAC
#16     ATCTC TTGTATTAGCTACACTGTTAGTGGGAACGTTATCAT-TCG  GTGAC
```

Class II
2,4,7,23,26
```
        ATCTC TTGACCCAAGAAGGGGTGTCAATCTAATCCGT CAACCATG
#8      ATCTC TTGACCCAAGAAGGGGTGTCAATCAAATCCGT CAACCATG
#17     ATCTC TTGACCCAAGAAGGGGTGTCAATCTAATCCGTACAACCATG ACGGTAAG
#27     ATCTC TTGACCCAAGAAGGGGTGTCAATCTAATCCGT CAAGGATG  CGGTAAG
```

Class III
```
#5      ATCTC AGGTGTTGGCTGCTCCCGCGGTGGCGGGAGGTAGGGTGAT GTGAC
#11     ATCTC AGGTGTTGGCATCTCCCGCGGTGGCGAGAGGTAGGGTGAT GTGAC
#6      ATCTC AGGTGTTGGCTGCTCTCGCGGTGGCGAGAGGTAGGGTCAT GTGAC
```

Unclassified
```
#21     ATCTC GCAGTCGAAGCTTCACTGTTAGTGCGGACGGGTAGACTTC GTGAC
#29     ATTTC TTCTGAATCCTCAATGTTAGTGGACCTAGTCGTAGTCGAT GTGAC
#12     ATCTC GGAGCCAGTTAGCATAATCTTCTGAATCCTCAATGTTAGT GTGAC
#10     ATCTC GGTGTTGGCTGGATAGAGCCGGTAGGCCCTATCGTAGGGT GTGAC
#3      GTCTC TTTTGTCCGCGACTCGAAATAGTGTGTTGAAGCAGCTCTA GTGAC
#28     AGCCA TAGTTCTACCAGCGGTTCGAAATAGTGAAGTGTTCGTGACTATCG GTAA
```

GGTAAGCTTGGCAC-3'

SIMPLE CATALYTIC DNA BIOSENSORS FOR IONS BASED ON COLOR CHANGES

FEDERALLY SPONSORED RESEARCH OR DEVELOPMENT

The U.S. Government may have rights in the present invention pursuant to the terms of grant number DEFG02-01ER63179 awarded by the Department of Energy.

BACKGROUND

Many metals pose a risk as environmental contaminants. A well-known example is lead. Low level lead exposure can lead to a number of adverse health effects, with as many as 9-25% of pre-school children presently at risk. The level of lead in the blood considered toxic is $\geq 10$ μg/dL (480 nM). Current methods for lead analysis, such as atomic absorption spectrometry, inductively coupled plasma mass spectrometry, and anodic stripping voltammetry, often require sophisticated equipment, sample pre-treatment, and skilled operators.

Simple, rapid, inexpensive, selective and sensitive methods that permit real time detection of $Pb^{2+}$ and other metal ions are very important in fields such as environmental monitoring, clinical toxicology, wastewater treatment, and industrial process monitoring. Furthermore, methods are needed for monitoring free or bioavailable, instead of total, metal ions in industrial and biological systems.

Many fluorescent chemosensors, including fluorophore-labeled organic chelators (Rurack, et al., 2000; Hennrich et al., 1999; Winkler et al., 1998; Oehme & Wolfbeis, 1997) and peptides (Walkup & Imperiali, 1996; Deo & Godwin, 2000; Pearce et al., 1998), have been developed for metal ion detection. These ion sensors are usually composed of an ion-binding motif and a fluorophore. Metal detection using these fluorescent chemosensors relies on the modulation of the fluorescent properties of the fluorophore by the metal-binding event. Detection limits on the level of micromolar and even nanomolar concentrations have been achieved for heavy metal ions including $Zn^{2+}$, $Cu^{2+}$, $Hg^{2+}$, $Cd^{2+}$ and $Ag^+$. The design and synthesis of a chemosensor that exhibits highly selective and sensitive binding of the metal ion of choice in aqueous solution is still a big challenge, although the metal binding and the fluorescent moieties of the sensor can be systematically varied to achieve desired properties. Although fluorescence spectroscopy is a technique well suited for detecting very small concentrations of analytes, a fluorometer is required to generate and detect the emitted signal. Thus, the need for expensive instrumentation and complicated operation procedures make this method impractical for applications such as household use, field testing or small clinic testing.

Nucleic acid molecules have previously been adapted to sense the presence of nucleic acids and to detect gene mutations from inherited diseases or chemical damages. In recent years, the molecular recognition and catalytic function of nucleic acids have been extensively explored. This exploration has lead to the development of aptamers and nucleic acid enzymes.

Aptamers are single-stranded oligonucleotides derived from an in vitro evolution protocol called systematic evolution of ligands by exponential enrichment (SELEX). Nucleic acid aptamers have been isolated from random sequence pools and can selectively bind to non-nucleic acid targets, such as small organic molecules or proteins, with affinities as high as $10^{-14}$ M (Uphoff et al., 1996; Famulok, 1999). Most aptamers undergo a conformational change when binding their cognate ligands. With this property, several DNA and RNA aptamers have been engineered to sense L-adenosine or thrombin through an internally labeled fluorescent reporter group (Jhaveri et al., 2000). Here, the conformational change in the aptamer upon binding leads to a change in fluorescence.

Nucleic acid enzymes are nucleic acid molecules that catalyze a chemical reaction. In vitro selection of nucleic acid enzymes from a library of $10^{14}$-$10^{15}$ random nucleic acid sequences offers considerable opportunity for developing enzymes with desired characteristics (Breaker & Joyce, 1994; Breaker, 1997). Compared with combinatorial searches of chemo- and peptidyl-sensors, in vitro selection of DNA/RNA is capable of sampling a larger pool of sequences, amplifying the desired sequences by polymerase chain reactions (PCR), and introducing mutations to improve performance by mutagenic PCR.

Allosteric ribozymes (or aptazymes), which combine the features of both aptamer and catalytic RNA, also hold promises for sensing small molecules (Potyrailo et al., 1998; Koizumi et al., 1999; Robertson & Ellington, 1999, 2000). Their reactivity is modulated through the conformational changes caused by the binding of small organic molecules to an allosteric aptamer domain. Therefore, the signal of ligand binding can be transformed into a signal related to chemical reaction.

Divalent metal ions can be considered as a special class of cofactors controlling the activity of nucleic acid enzymes. The reaction rate of the nucleic acid enzymes depends on the type and concentration of the metal ion in solution. Several RNA and DNA enzymes obtained through in vitro selection are highly specific for $Cu^{2+}$, $Zn^{2+}$, and $Pb^{2+}$, with metal ion requirements on the level of micromolar concentrations (Breaker & Joyce, 1994; Pan & Uhlenbeck, 1992; Carmi et al., 1996; Pan et al., 1994; Cuenoud & Szotak, 1995; Li et al., 2000; Santoro et al., 2000).

A variety of methods have been developed for assembling metal and semiconductor colloids into nanomaterials. These methods have focused on the use of covalent linker molecules that possess functionalities at opposing ends with chemical affinities for the colloids of interest. One of the most successful approaches to date, (Brust et al., (1995)), involves the use of gold colloids and well-established thiol adsorption chemistry (Bain & Whitesides, (1989); Dubois & Nuzzo (1992)). In this approach, linear alkanedithiols are used as the particle linker molecules. The thiol groups at each end of the linker molecule covalently attach themselves to the colloidal particles to form aggregate structures. The drawbacks of this method are that the process is difficult to control and the assemblies are formed irreversibly. Methods for systematically controlling the assembly process are needed if the materials properties of these structures are to be exploited fully.

The potential utility of DNA for the preparation of biomaterials and in nanofabrication methods has been recognized. Researchers have focused on using the sequence-specific molecular recognition properties of oligonucleotides to design impressive structures with well-defined geometric shapes and sizes. Shekhtman et al., (1993); Shaw & Wang, (1993); Chen et al., (1989); Chen & Seeman, (1991); Smith and Feigon (1992); Wang et al., (1993); Chen et al., (1994); Marsh et al., (1995); Mirkin (1994); Wells (1988); Wang et al., (1991). However, the theory of producing DNA structures is well ahead of experimental confirmation. Seeman et al., New J. Chem., 17, 739-755 (1993).

Agglutation assays are well known for the detection of various analytes. The basic principle of an agglutination assay is the formation of clumps (agglutination or aggregation) of small particles coated with a binding reagent when exposed to a multi-valent binding partner specific for the binding reagent. Particles routinely used in agglutation assays include, for example, latex particles, erythrocytes (RBCs), or bacterial cells (often stained to make the clumps visible). Typically, a binding reagent, such as an antibody, is attached to the particles. A sample thought to contain the analyte of interest is contacted with a suspension of such coated particles. If the analyte is present, cross linking of the particles occurs due to bond formation between the antibodies on the particles and the analyte in the sample. Such binding results in the agglutation of the particles which can be detected either visually or with the aid of simple instrumentation. In an alternative protocol, an antigen is attached to the particles and the presence of an antibody specific for the antigen detected in the sample.

More recently, metal, semiconductor and magnetic particles have been used in aggregation assays. For example, particles comprising metal (e.g., gold, silver, copper and platinum), semiconductor (e.g., CdSe, CdS, and CdS or CdSe coated with ZnS) and magnetic (e.g., ferromagnetite) colloidal materials have been described. Other particle types include ZnS, ZnO, $TiO_2$, AgI, AgBr, $HgI_2$, PbS, PbSe, ZnTe, CdTe, $In_2 S_3$, $In_2 Se_3$, $Cd_3 P_2$, $Cd_3 As_2$, InAs, and GaAs.

Mirkin et al. (U.S. Pat. No. 6,361,944) describes aggregation assays for detecting a nucleic acid in a sample. This method involves incubating a sample thought to contain a nucleic acid with particles having oligonucleotides attached to the surface (particle-oligonucleotide conjugates). The oligonucleotides on each particle have an oligonucleotide complementary to one of the sequences of at least two portions of the nucleic acid. Alternatively, at least two types of particles having oligonucleotides attached may be used. The oligonucleotides on the first type of particles having a sequence complementary to one portion of the nucleic acid and the oligonucleotides on the second type of particles have a sequence complementary to a second portion of the sequence of the nucleic acid. The incubation takes place under conditions effective to allow hybridization of the oligonucleotides on the particles with the nucleic acid in the sample. Such a hybridization results in an aggregation of the particles. This produces a color change which may be detected visually or with simple instrumentation. For example, the aggregation of gold particles results in a color change from red to purple (Mirkin (U.S. Pat. No. 6,361,944)).

Methods of detection based on observing such a color change with the naked eye are cheap, fast, simple, robust (the reagents are stable) and do not require specialized or expensive equipment. This makes such methods particularly suitable for use in applications such as the detection of lead in paint or heavy metals in water.

BRIEF SUMMARY

The present invention provides a method of detecting the presence of an ion in a sample. A new class of DNA enzyme-based biosensor for ions is provided. This combines the high selectivity of DNA enzymes with the convenience of particle aggregation-based detection. Such selectivity and convenience provides for semi-quantitative and quantitative detection of ions over a concentration range of several orders of magnitude.

The sample may be any solution that may contain an ion (before or after pre-treatment). The sample may contain an unknown concentration of an ion and may contain other ions. For example, the sample may be paint that is tested for lead content. The sample may be diluted yet still remains a sample. The sample may be obtained from the natural environment, such as a lake, pond, or ocean, an industrial environment, such as a pool or waste stream, a research lab, common household, or a biological environment, such as blood.

In one embodiment, the invention provides a nucleic acid enzyme, a substrate and particles. The nucleic acid enzyme, a substrate and particles are provided as, or form an aggregate. The method for detection of the ion comprises contacting the aggregate with the ion wherein the nucleic acid enzyme causes cleavage of the substrate in the presence of the ion. The method for detection of the ion may be performed in the presence of other ions.

In a preferred embodiment, the particles are gold particles and the presence of the ion in detected by observing a color change resulting from a breakdown of the aggregate.

In another aspect, the invention provides kits for the detection of an ion.

BRIEF DESCRIPTION OF THE DRAWINGS

FIG. 1. Selection scheme for RNA-cleaving deoxyribozymes.

FIG. 2. (SEQ ID NOS 13-23, respectively, in order of appearance) Sequence classes of the cloned Zn-DNA. The numbers on the left are the clone-numbers randomly assigned to the sequences during the cloning and sequencing process. The highly conserved sequences (Region-20nt) are in bold. The covariant nucleotides are underlined. The 5'- and the 3'-primer binding sequences are shown in italic.

FIG. 3. (SEQ ID NOS 24-42, respectively, in order of appearance) Sequence classes of the cloned Co-DNA. The clone-numbers are listed on the left. The 5' and the 3' primer binding sequences are in italic.

FIG. 4. (SEQ ID NOS 43-70, respectively, in order of appearance) Sequence alignment of the N40 region of the reselected Zn-DNAs. The wild-type sequence is listed on the top, followed by the reselected Zn-DNA sequences. Only the point mutations are shown for the reselected sequences, while the nucleotides that are identical to the wild type at the corresponding positions are omitted. Numbers listed on the left are clone-numbers. The rate constants ($k_{obs}$) of several reselected Zn-DNA in 100 μM $Zn^{2+}$ are shown on the right.

FIG. 7. Comparison of G3 deoxyribozyme with class II Co-DNA.

X represents variable sequences. The boxed region was also found in class II Co-DNA.

DETAILED DESCRIPTION

Figure 1A:
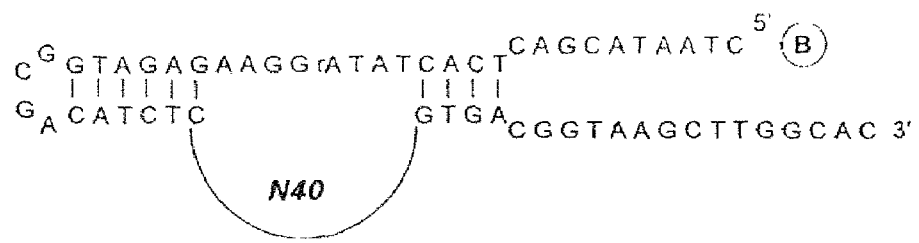
FIG. 1A. (SEQ ID NO: 12) Starting pool of random-sequenced DNAs, engineered to contain two substrate-binding domains. Each member of the pool contains a 5'-terminal biotin (encircled B), a single embedded ribonucleotide (rA) and a 40-nucleotide random sequence domain (N40).

The invention described herein represents a new class of DNA enzyme-based biosensor for ions. It combines the high selectivity of DNA enzymes with the convenience of particle aggregation-based detection. Such selectivity and convenience provides for semi-quantitative and quantitative detection of ions over a concentration range of several orders of magnitude. In a preferred embodiment, the aggregation-based detection domain is decoupled from the ion-recognition/catalysis domain, and therefore the sensitivity and selectivity of this system may be manipulated by a careful choice of particles and aggregation method, and by performing in vitro selection of ion-binding domains to not only keep sequences reactive with the ion of choice, but also remove sequences that also respond to other ions.

Nucleic Acid Enzymes

A growing number of nucleic acid enzymes have been discovered or developed showing a great diversity in catalytic activity (Table 1 and Table 2). Many if not all of the enzymes are dependent on one or more ion cofactors. In vitro selection may be used to "enhance" selectivity and sensitivity for a particular ion. Such enzymes find particular utility in the compositions and methods of the present invention. For example, nucleic acid enzymes that catalyze molecular association (ligation, phophorylation, and amide bond formation) or dissociation (cleavage or transfer) are particularly useful.

In preferred embodiments, a nucleic acid enzyme that catalyzes the cleavage of a nucleic acid in the presence of an ion is used. The nucleic acid enzyme may be RNA (ribozyme), DNA (deoxyribozyme), a DNA/RNA hybrid enzyme, or a peptide nucleic acid (PNA) enzyme. PNAs comprise a polyamide backbone and the bases found in naturally occurring nucleosides and are commercially available from, e.g., Biosearch, Inc. (Bedford, Mass.).

Ribozymes that may be used in the present invention include, but are not limited to, group I and group II introns, the RNA component of the bacterial ribonuclease P, hammerhead, hairpin, hepatitis delta virus and Neurospora VS ribozymes. Also included are in vitro selected ribozymes, such as those isolated by Tang and Breaker (2000).

One limitation of using a ribozyme is that they tend to be less stable than deoxyribozymes. Thus, in preferred embodiments, the nucleic acid enzyme is a deoxyribozyme. Preferred deoxyribozymes include those shown in FIGS. 6A-6F and deoxyribozymes with extended chemical functionality (Santoro et al., 2000).

TABLE 1

Reactions catalyzed by ribozymes that were isolated from in vitro selection experiments.

| Reaction | $k_{cat}$ (min$^{-1}$) | $K_m$ (μM) | $k_{cat}/k_{uncat}$[a] | Reference |
| --- | --- | --- | --- | --- |
| Phosphoester centers | | | | |
| Cleavage | 0.1 | 0.03 | $10^5$ | Vaish, 1998 |
| Transfer | 0.3 | 0.02 | $10^{13}$ | Tsang, 1996 |
| Ligation | 100 | 9 | $10^9$ | Ekland, 1995 |
| Phosphorylation | 0.3 | 40 | $>10^5$ | Lorsch, 1994 |
| Mononucleotide polymerization | 0.3 | 5000 | $>10^7$ | Ekland, 1996 |
| Carbon centers | | | | |
| Aminoacylation | 1 | 9000 | $10^6$ | Illangasekare, 1997 |
| Aminoacyl ester hydrolysis | 0.02 | 0.5 | 10 | Piccirilli, 1992 |
| Aminoacyl transfer | 0.2 | 0.05 | $10^3$ | Lohse, 1996 |
| N-alkylation | 0.6 | 1000 | $10^7$ | Wilson, 1995 |
| S-alkylation | $4 \times 10^{-3}$ | 370 | $10^3$ | Wecker, 1996 |
| Amide bond cleavage | $1 \times 10^{-5}$ | | $10^2$ | Dai, 1995 |
| Amide bond formation | 0.04 | 2 | $10^5$ | Wiegand, 1997 |
| Peptide bond formation | 0.05 | 200 | $10^6$ | Zhang, 1997 |
| Diels-Alder cycloaddition | >0.1 | >500 | $10^3$ | Tarasow, 1997 |
| Others | | | | |
| Biphenyl isomerization | $3 \times 10^5$ | 500 | $10^2$ | Prudent, 1994 |
| Porphyrin metallation | 0.9 | 10 | $10^3$ | Conn, 1996 |

[a]Reactions catalyzed by ribozymes that were isolated from in vitro selection experiments. kcat/kuncat is the rate enhancement over uncatalyzed reaction.

TABLE 2

Deoxyribozymes isolated through in vitro selection.

| Reaction | Cofactor | $k_{max}$ (min$^{-1}$)[a] | $k_{cat}/k_{uncat}$ | Reference |
| --- | --- | --- | --- | --- |
| RNA transesterification | $Pb^{2+}$ | 1 | $10^5$ | Breaker, 1994 |
| | $Mg^{2+}$ | 0.01 | $10^5$ | Breaker, 1995 |
| | $Ca^{2+}$ | 0.08 | $10^5$ | Faulhammer, 1997 |
| | $Mg^{2+}$ | 10 | $>10^5$ | Santoro, 1997 |
| | None | 0.01 | $10^8$ | Geyer, 1997 |
| | L-histidine | 0.2 | $10^6$ | Roth, 1998 |
| | $Zn^{2+}$ | ~40 | $>10^5$ | Li, J., 2000 |
| DNA cleavage | $Cu^{2+}$ | 0.2 | $>10^6$ | Carmi, 1996 |
| DNA ligation | $Cu^{2+}$ or $Zn^{2+}$ | 0.07 | $10^5$ | Cuenod, 1995 |
| DNA phosphorylation | $Ca^{2+}$ | 0.01 | $10^9$ | Li, Y., 1999 |

TABLE 2-continued

Deoxyribozymes isolated through in vitro selection.

| Reaction | Cofactor | $k_{max}$ (min$^{-1}$)$^a$ | $k_{cat}/k_{uncat}$ | Reference |
|---|---|---|---|---|
| 5',5'-pyrophophate formation | Cu$^{2+}$ | $5 \times 10^{-3}$ | $>10^{10}$ | Li, Y., 2000 |
| Porphyrin metalation | None | 1.3 | $10^3$ | Li, Y., 1996 |

$^a k_{max}$ is the maximal rate constant obtained under optimized conditions.

An advantage of ribozymes and deoxyribozymes is that they may be produced and reproduced using biological enzymes and appropriate templates. However, the present invention is not limited to ribozymes and deoxyribozymes. Nucleic acid enzymes that are produced by chemical oligo-synthesis methods are also included. Thus, nucleic acids including nucleotides containing modified bases, phosphate, or sugars may be used in the compositions and methods of the present invention. Modified bases are well known in the art and include inosine, nebularine, 2-aminopurine riboside, $N^7$-denzaadenosine, and $O^6$-methylguanosine (Earnshaw & Gait, 1998). Modified sugars and phosphates are also well known and include 2'-deoxynucleoside, abasic, propyl, phosphorothioate, and 2'-O-allyl nucleoside (Earnshaw & Gait, 1998). DNA/RNA hybrids and PNAs may be used in the compositions and methods of the present invention. The stability of PNAs and relative resistance to cellular nucleases make PNA enzymes amenable to in vivo applications.

In certain embodiments, the substrate for the nucleic acid enzyme and the enzyme itself are contained in the same nucleic acid strand. Such enzymes are cis-acting enzymes. Examples include the $Zn^{2+}$-dependent deoxyribozymes (Zn-DNA) created in Example 2 (FIG. 1A and FIG. 2).

Figure 5:
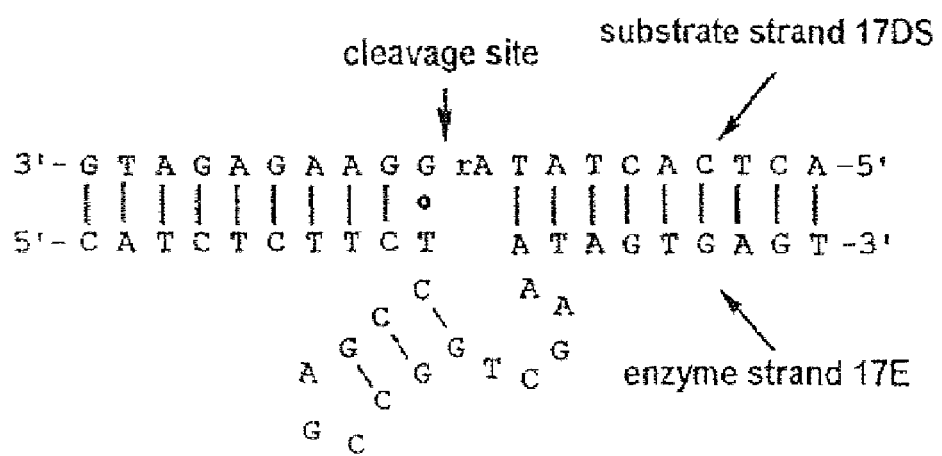
FIG. 5. (SEQ ID NOS 1 & 2) Proposed secondary structure of the Zn(II)-dependent trans-cleaving deoxyribozyme.

In preferred embodiments, the nucleic acid enzyme cleaves a nucleic acid strand that is separate from the strand comprising the enzyme (trans-acting). One advantage of utilizing trans-activity is that, after cleavage, the product is removed and additional substrate may be cleaved by the enzymatic strand. A preferred nucleic acid enzyme is 5'-CATCTCT-TCTCCGAGCCGGTCGAAATAGTGAGT-3' (17E; FIG. 5; SEQ ID NO: 1). The corresponding preferred substrate to 17E is 5'-ACTCACTATrAGGAAGAGATG-3' (17DS; FIG. 5; SEQ ID NO: 2), where rA denotes a single ribonucleotide.

It may be beneficial to use directed mutation to change one or more properties of a nucleic acid enzyme or its substrate. Using 17E and 17DS as an example, one may wish to alter the avidity of the two arms of the hybridized enzyme and substrate. The "arms" are those areas displaying Watson-Crick base pairing in FIG. 5. To alter avidity, one may increase or decrease the length of the arms. Increasing the length of the arms increases the number of Watson-Crick bonds, thus increasing the avidity. The opposite is true for decreasing the length of the arms. Decreasing the avidity of the arms facilitates the removal of substrate from the enzyme, thus allowing faster enzymatic turnover.

Another method of decreasing avidity includes creating mismatches between the enzyme and the substrate. Alternatively, the G-C content of the arms may be altered. Of course, the effect of any directed change should be monitored to ensure that the enzyme retains its desired activity, including ion sensitivity and selectivity. In light of the present disclosure, one of skill in the art would understand how to monitor for a desired enzymatic activity. For example, to ensure that the mutated enzyme maintained sensitivity and selectivity for $Pb^{2+}$, one would test to determine if the mutated enzyme remained reactive in the presence of lead (sensitivity) and maintained its lower level of activity in the presence of other ions (selectivity).

The nucleic acid enzyme is sensitive and selective for a single ion. The ion may be any anion, for example, arsenate ($AsO_4^{3-}$), or cation. The ion may be monovalent, divalent, trivalent, or polyvalent. Examples of monovalent cations include $K^+$, $Na^+$, $Li^+$, $Tl^+$, $NH_4^+$ and $Ag^+$. Examples of divalent cations include $Mg^{2+}$, $Ca^{2+}$, $Mn^{2+}$, $Co^{2+}$, $Ni^{2+}$, $Zn^{2+}$, $Cd^{2+}$, $Cu^{2+}$, $Pb^{2+}$, $Hg^{2+}$, $Pt^{2+}$, $Ra^{2+}$, $Ba^{2+}$, $UO_2^{2+}$ and $Sr^{2+}$. Examples of trivalent cations include $Co^{3+}$, $Cr^{3+}$, and lanthanide ions ($Ln^{3+}$). Polyvalent cations include $Ce^{4+}$, $Cr^{6+}$, spermine, and spermidine. The ion detected by the biosensor also includes ions having a metal in a variety of oxidation states. Examples include K(I), Na(I), Li(I), Tl(I), Ag(I), Hg(I), Mg(II), Ca(II), Mn(II), Co(II), Ni(II), Zn(II), Cd(II), Pb(II), Hg(II), Pt(II), Ra(II), Ba(II), Sr(II), Co(III), Cr(III), Ln(III), Ce(IV), Cr(VI) and U(VI).

The biosensors of the present invention may be used to monitor contaminants in the environment; in such a case preferred ions are those that are toxic to living organisms, e.g. $Ag^+$, $Pb^{2+}$ and $Hg^{2+}$.

Often the nucleic acid enzymes that have activity with one ion also have at least some activity with one or more other ions. Such multi-sensitive enzymes may still be used in the compositions and methods of the present invention. However, it should be understood that use of a multi-sensitive enzyme may lead to uncertainty as to which of the ions is present. In such cases, measuring the rate of enzymatic activity, using serial dilutions, or using an array of nucleic acid enzymes may be helpful in deciphering which ion is present.

In Vitro Selection of Nucleic Acid Enzymes

Many nucleic acid enzymes that are dependent on ions, particularly metal ions, for activity are known in the art (Breaker & Joyce, 1994; Pan & Uhlenbeck, 1992; Cuenoud & Szostak, 1995; Carmi et al., 1996; Li et al., 2000; Santoro et al., 2000). In light of the present disclosure, one of skill in the art would understand how to utilize a known nucleic acid enzyme in the methods and biosensors of the present invention. Furthermore, the present invention may include a nucleic acid enzyme created by in vitro selection. Methods of in vitro selection of nucleic acid enzymes are known in the art and described herein.

In vitro selection is a technique in which RNA or DNA molecules with certain functions are isolated from a large number of sequence variants through multiple cycles of selection and amplification (Joyce, 1994; Chapman et al., 1994). The concept of in vitro selection of catalytic RNA molecules was first introduced in the late 1980's. Since then, it has been widely applied to obtain ribozymes with maximized activities or novel catalytic abilities, and to identify oligonucleotides (called aptamers) that bind to certain proteins or small molecules with high affinity. The process for aptamers selection is sometimes referred as systematic evolution of ligands by exponential enrichment (SELEX)(Tuerk & Gold, 1990).

The first catalytic DNA (deoxyribozyme) was isolated by Breaker and Joyce in 1994 through in vitro selection. This deoxyribozyme is able to catalyze phosphodiester cleavage reaction in the presence of $Pb^{2+}$. Unlike RNA-based catalysts, DNA molecules with catalytic functions have not been encountered in nature, where DNA exists primarily as base-paired duplex and serves mainly as the carrier of genetic information. The identification of DNA molecules with catalytic functions further demonstrated the power of in vitro selection.

In vitro selection is typically initiated with a large collection of randomized sequences. A typical DNA or RNA library for selection contains $10^{13}$-$10^{16}$ sequence variants. The construction of a completely randomized pool is accomplished by chemical synthesis of a set of degenerated oligonucleotides using standard phosphoramidite chemistry. The 3'-phosphoramidite compounds of four nucleosides (A, C, G, and T) are premixed before being supplied to an automated DNA synthesizer to produce oligonucleotides. By controlling the ratio of four phosphoroamidites, the identity at each nucleotide position can be either completely random, i.e. with equal chance for each base, or biased toward a single base. Other strategies for creating a randomized DNA library include applying mutagenic polymerase chain reaction (PCR) and template-directed mutagenesis (Tsang and Joyce, 1996; Cadwell and Joyce, 1992, 1994). For the purpose of in vitro selection of functional RNA molecules, the randomized DNA library is converted to an RNA library through in vitro transcription.

In vitro selection takes advantage of a unique property of RNA and DNA, i.e., the same molecule can possess both genotype (coding information) and phenotype (encoded function). The DNA or RNA molecules in the randomized library are screened simultaneously. Those sequences that exhibit a desired function (phenotype) are separated from the inactive molecules. Usually the separation is performed through affinity column chromatography, being linked to or released from a solid support, gel electrophoresis separation, or selective amplification of a tagged reaction intermediate. The genotype of the active molecules are then copied and amplified, normally through polymerase chain reaction (PCR) for DNA or isothermal amplification reaction for RNA. Mutations can be performed with mutagenic PCR to reintroduce diversity to the evolving system. These three steps—selection, amplification and mutation, are repeated, often with increasing selection stringency, until sequences with the desired activity dominate the pool.

Novel nucleic acid enzymes isolated from random sequences in vitro have extended the catalytic repertoire of RNA and DNA far beyond what has been found in nature. The selected ribozymes are capable of catalyzing a wide range of reactions at both phosphate and non-phosphate centers (Table 1). The reactions that are catalyzed by deoxyribozymes are less diverse, compared with the ribozymes (Table 2). However, the catalytic rate ($k_{cat}$) of most deoxyribozymes is comparable to that of the ribozymes catalyzing the same reaction. In certain cases, the catalytic efficiency ($k_{cat}/K_m$) of nucleic acid enzymes even exceeds that of the protein enzymes.

Figure 6A:
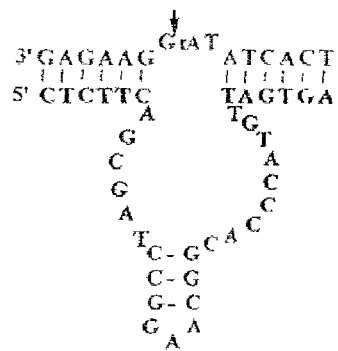
FIG. 6A (SEQ ID NOS 71 & 72) and FIG. 6B (SEQ ID NOS 73 & 74). The deoxyribozyme selected using $Mg^{2+}$ or $Pb^{2+}$ as cofactor (Breaker & Joyce, 1994, 1995).
Figure 6B:
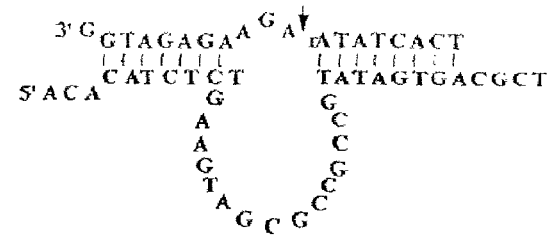
FIG. 6. Sequences and proposed secondary-structures of several RNA-cleaving deoxyribozymes.
FIG. 6C (SEQ ID NOS 75 & 76) and FIG. 6D (SEQ ID NOS 77 & 78). The 10̃23 and the 8̃17 deoxyribozymes selected in $Mg^{2+}$ to cleave all-RNA substrate (Santoro & Joyce, 1997).
FIG. 6E (SEQ ID NOS 79 & 80). A deoxyribozyme selected using L-histidine as cofactor.
FIG. 6F (SEQ ID NOS 81 & 82). The 17E deoxyribozyme selected in $Zn^{2+}$. In each structure, the upper strand is the substrate and the lower strand is the enzyme. Arrows identify the site of RNA transesterification.
Figure 6C:
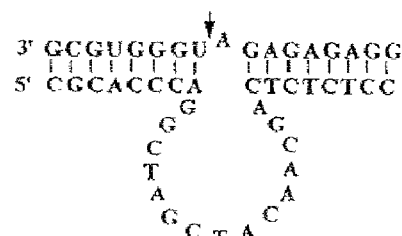
Figure 6D:
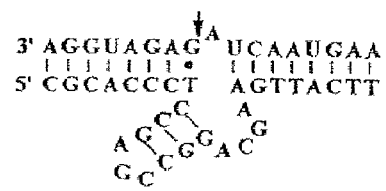
Figure 6E:
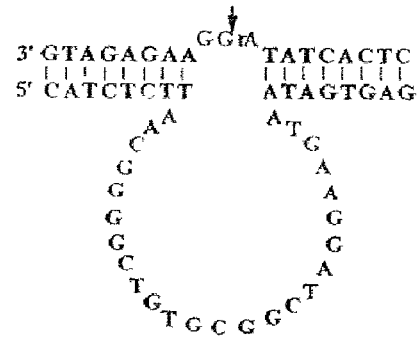
Figure 6F:
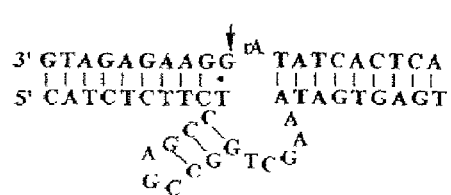

In vitro selection can be used to change the ion specificity or binding affinity of existing ribozymes, or to obtain nucleic acid enzymes specific for desired ions. For example, in vitro-selected variants of the group I intron (Lehman & Joyce, 1993) and the RNase P ribozyme (Frank & Pace, 1997) have greatly improved activity in $Ca^{2+}$, which is not an active metal ion cofactor for native ribozymes. The $Mg^{2+}$ concentration required for optimal hammerhead ribozyme activity has been lowered using in vitro selection to improve the enzyme performance under physiological conditions (Conaty et al., 1999; Zillman et al., 1997). Breaker and Joyce have isolated several RNA-cleaving deoxyribozymes using $Mg^{2+}$, $Mn^{2+}$, $Zn^{2+}$, or $Pb^{2+}$ as the cofactor (Breaker & Joyce, 1994, 1995). Only the sequence and structure of the $Pb^{2+}$-dependent and the $Mg^{2+}$-dependent deoxyribozymes were reported (FIG. 6A and 6B). Other examples of metal-specific RNA/DNA enzymes obtained through in vitro selection include a $Pb^{2+}$-specific RNA-cleaving ribozyme (called leadzyme)(Pan & Uhlenbeck, 1992), a $Cu^{2+}$-specific DNA-cleaving deoxyribozyme (Carmi et al., 1996), and a DNA ligase active in $Zn^{2+}$ and $Cu^{2+}$ (Cuonod & Szostak, 1995).

Often nucleic acid enzymes developed for a specific metal ion by in vitro selection will have activity in the presence of other metal ions. For example, 17E deoxyribozyme was developed by in vitro selection for activity in the presence of $Zn^{2+}$. Surprisingly, the enzyme showed greater activity in the presence of $Pb^{2+}$ than $Zn^{2+}$. Thus, although produced in a process looking for $Zn^{2+}$-related activity, 17E may be used as a sensitive and selective sensor of $Pb^{2+}$.

To produce nucleic acid enzymes with greater selectivity, a negative selection step may be included in the process. For Example, $Pb^{2+}$-specific deoxyribozymes may be isolated using a similar selection scheme as for the selection of $Co^{2+}$- and $Zn^{2+}$-dependent DNA enzymes described in Example 2. In order to obtain deoxyribozymes with high specificity for $Pb^{2+}$, negative-selections may be carried out in addition to the positive selections in the presence of $Pb^{2+}$.

For negative selection, the DNA pool is selected against a "metal soup", which contains various divalent metal ions (e.g. $Mg^{2+}$, $Ca^{2+}$, $Mn^{2+}$, $Zn^{2+}$, $Cd^{2+}$, $Co^{2+}$, $Cu^{2+}$, etc.). Those sequences that undergo self-cleavage in the presence of divalent metal ions other than $Pb^{2+}$ are then washed off the column. The remaining sequences are further selected with $Pb^{2+}$ as the cofactor. $Pb^{2+}$-dependent deoxyribozymes with different affinities for $Pb^{2+}$ can be obtained by controlling the reaction stringency ($Pb^{2+}$ concentration). Besides the oligonucleotide sequences discussed here, other sequences shall be useful in the practicing of this invention. Such sequences are described in U.S patent application Ser. No. 09/605558, filed Jun. 27, 2000, the contents of which are incorporated by this reference.

DNA Coated Particles

Methods of making metal, semiconductor and magnetic particles are well-known in the art. Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs particles are also known. See, e.g., Mirkin et al. U.S. Pat. No. 6,361,944. Suitable particles are also commercially available from, e.g., Amersham Biosciences, (Piscataway, N.J.) (gold) and Nanoprobes, Inc. (Yaphank, N.Y.) (gold).

In addition, other types of particles may be used in the present invention. For example, polystyrene latex particles or latex particles containing dye may be used. The critical requirement is that a detectable change must occur upon aggregation/aggregate breakdown. In addition, the composition of the particles must be such that the particles do not interfere with the cleavage of the substrate by the nucleic acid enzyme in the presence of the metal ion.

Gold colloidal particles are preferred for use in detecting metal ions. Gold colloidal particles have high extinction coefficients for the bands that give rise to their intense colors. These colors vary with particle size, concentration, interparticle distance, and extent of aggregation and shape of the aggregates, making these materials particularly useful for calorimetric assays. For instance, hybridization of oligonucleotides attached to gold particles with oligonucleotides and nucleic acids results in an immediate color change visible to the naked eye (see, e.g., Mirkin et al. U.S. Pat. No. 6,361,944).

Gold particles, oligonucleotides or both are functionalized in order to attach the oligonucleotides to the particles. Such methods are known in the art. For instance, oligonucleotides functionalized with alkanethiols at their 3'-termini or 5'-termini readily attach to gold particles. See Whitesides (1995). See also, Mucic et al. (1996) (describes a method of attaching 3' thiol DNA to flat gold surfaces; this method can be used to attach oligonucleotides to particles). The alkanethiol method can also be used to attach oligonucleotides to other metal, semiconductor and magnetic colloids and to the other particles listed above. Other functional groups for attaching oligonucleotides to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell (1974) and Matteucci and Caruthers (1981) for binding of oligonucleotides to silica and glass surfaces, and Grabar et al., (1995) for binding of aminoalkylsiloxanes and for similar binding of mercaptoakly-lylsiloxanes). Oligonucleotides terminated with a 5' thionucleoside or a 3' thionucleoside may also be used for attaching oligonucleotides to solid surfaces. Gold particles may be attached to oligonucleotides using biotin-labeled oligonucleotides and streptavidin-gold conjugate colloids; the biotin-streptavidin interaction attaches the colloids to the oligonucleotide. Shaiu et al., (1993). The following references describe other methods which may be employed to attached oligonucleotides to particles: Nuzzo et al., (1987) (disulfides on gold); Allara and Nuzzo (1985) (carboxylic acids on aluminum); Allara and Tompkins (1974) (carboxylic acids on copper); Iler, (1979) (carboxylic acids on silica); Timmons and Zisman, (1965) (carboxylic acids on platinum); Soriaga and Hubbard, (1982) (aromatic ring compounds on platinum); Maoz and Sagiv, (1987) (silanes on silica).

Each particle will have a plurality of oligonucleotides attached to it. As a result, each particle-oligonucleotide conjugate can bind to a plurality of oligonucleotides or nucleic acids having the complementary sequence.

Oligonucleotides of defined sequences are used for a variety of purposes in the practice of the invention. Methods of making oligonucleotides of a predetermined sequence are well-known. See, e.g., Sambrook et al., (1989) and F. Eckstein (1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

Biosensors

Described herein are nucleic acid enzymes that are dependent on the presence of a specific ion for activity. Using particle labeling, it is possible to measure enzymatic activity, and hence ion concentration, without the need of complex instrumentation. These qualities make the compositions of the present invention excellent for use in biosensors for detecting ions.

Many biosensors utilizing nucleic acids are known in the art. For example, biosensors using aptamers have been developed for detecting molecules such as thrombin or adenosine (Potyrailo et al., 1999; Lee & Walt, 2000). In light of the present disclosure, one of ordinary skill in the art would know how to modify the nucleic acid biosensors to include nucleic acid enzymes.

In a simple embodiment, a biosensor of the present invention comprises a nucleic acid enzyme, a cleavable substrate for the nucleic acid enzyme, and particles labeled with oligoribonucleotides complementary to at least two portions of the cleavable substrate. Preferably, the substrate is modified, for example, by extension of the 3' and 5' ends by a number of bases which act as "sticky end" for annealing to the complementary DNA strand on the particles. Modification of the substrate allows complexes comprising of substrate linked particles to be formed without inhibiting the nucleic acid enzyme/cleavable substrate interaction. However, where the substrate contains regions not critical for interaction with the nucleic acid enzyme, modification may not be necessary.

Figure 8:
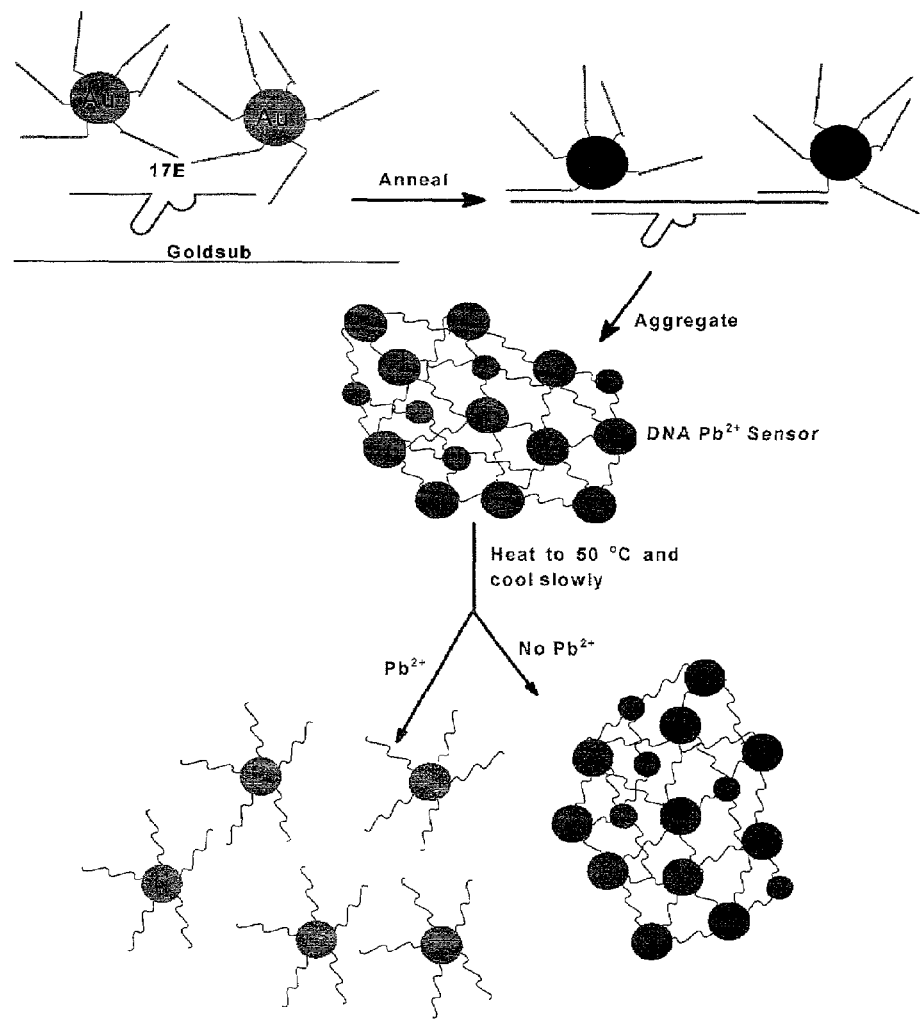
FIG. 8. Figure showing an assay protocol for particle based DNA assay for $Pb^{++}$.

In a method using this embodiment the nucleic acid enzyme, cleavable substrate, and labeled particles are combined to form aggregated complexes. Such aggregates are contacted with a sample suspected of containing an ion to which the enzyme is sensitive. In the presence of the ion, the enzyme cleaves the substrate causing a break-up of the aggregates. An example of such an assay protocol is shown in FIG. 8. In some embodiments, heating of the aggregates to a temperature above the "melting point" of the complex may be necessary. In such an embodiment, the presence of the ion allows the enzyme to cleave the substrate, preventing "re-aggregation" of the complex. However, in certain embodiments, heating is not required (see, for example, Example 8).

A change in the aggregation state of the particles may be detected by observing an color change which accompanies the change in state. For example, the a breakdown of aggregation of gold particles results in a color change from purple to red. Furthermore, the amount of substrate cleavage depends on the concentration of the ion. A low concentration of ion results in only partial cleavage of the substrate, producing a mixture of single particles and aggregates with different degree of aggregations. Hence, this simple color test can be used as a semi-qualitative or qualitative way to detect an ion, for example, $Pb^{2+}$. The color difference can be amplified to improve the sensitivity of the method. For example, this may be achieved by spotting the resulting solution onto an alumina TLC plate. Different degrees of color change are produced, depending on the amount of ion present. Alternatively, a quantitative assay can be achieved by measuring the optical spectra of the assay mixture.

The detectable change that occurs upon a change in the aggregation state of the particles may be a color change, the formation of aggregates of the particles, or the precipitation of the aggregated particles. The color changes can be observed with the naked eye or spectroscopically. The formation of aggregates of the particles can be observed by electron microscopy or by nephelometry. The precipitation of the aggregated particles can be observed with the naked eye or microscopically. However, changes observable with the naked eye are preferred, particularly a color change observable with the naked eye.

The observation of a color change with the naked eye can be made more readily against a background of a contrasting color. For instance, when gold particles are used, the observation of a color change is facilitated by spotting a sample of the hybridization solution on a solid white surface (such as silica or alumina TLC plates, filter paper, cellulose nitrate membranes, and nylon membranes) and allowing the spot to dry. Initially, the spot retains the color of the hybridization solution (which ranges from pink/red, in the absence of aggregation, to purplish-red/purple, if there has been aggregation). On drying, a blue spot develops if aggregation is present prior to spotting. In the absence of aggregation (e.g., because the target ion is present), the spot is pink. The blue and the pink spots are stable and do not change on subsequent cooling or heating or over time. They provide a convenient permanent record of the test. No other steps are necessary to observe the color change.

Alternatively, assay results may be visualized by spotting a sample onto a glass fiber filter (e.g., Borosilicate Microfiber Filter, 0.7 micron pore size, grade FG75, for use with gold particles 13 nm in size), while drawing the liquid through the filter. Subsequent rinsing with water washes the excess, non-hybridized probes through the filter, leaving behind an observable spot comprising the aggregates. Additional methods useful in visualizing assay results are described in Mirkin et al. U.S. Pat. No. 6,361,944.

The above methods allow the ion to be detected in a variety or sample types, including a bodily fluids, and in the presence of other ions. Various techniques may be employed to improve the accuracy and precision of the above method of observation. Standards containing known amounts of ion may be assayed along side the unknown sample and the color changes compared. Alternatively, standard color charts, similar to those used with pH papers, may be provided.

Many variants of these simple embodiments are included within the scope of the invention. The specificity of the nucleic acid enzyme may be varied to allow specific detection of a wide range of ions. In addition, the composition, size and surface properties of the particles may be optimized to obtain preferred aggregation and visual properties. Similarly, parameters such as the particle/oligonucleotide probe coupling technology, and the length and sequence of the oligonucleotide probes and substrate may be varied to optimize the performance of the assay.

The invention also provides kits for detecting ions. In one embodiment, the kit comprises at least one container, the container holding at least one type of particles having oligonucleotides attached thereto; a cleavable substrate; and a nucleic acid enzyme. The oligonucleotides on the particles have a sequence complementary to the sequence of at least a first and a second portion of the cleavable substrate. The first and second portions of the cleavable substrate are separated by a third portion of the substrate that is cleaved by the nucleic acid enzyme in the presence of the ion. The above components may be supplied in an aggregated state.

In a second embodiment, the above kit comprises at least two types of particles having oligonucleotides attached thereto. A first type of particles has oligonucleotides which have a sequence complementary to the sequence of a first portion of the cleavable substrate. A second type of particles has oligonucleotides which have a sequence complementary to the sequence of a second portion of the cleavable substrate. The first and second portions of the cleavable substrate are separated by a third portion of the substrate that is cleaved by the nucleic acid enzyme in the presence of the ion.

When a kit is supplied, the different components of the composition may be packaged in separate containers and admixed immediately before use. Such packaging of the components separately may permit long-term storage of the active components. For example, one of more of the particles having oligonucleotides attached thereto; the cleavable substrate; and the nucleic acid enzyme are supplied in separate containers.

The reagents included in the kits can be supplied in containers of any sort such that the life of the different components are preserved and are not adsorbed or altered by the materials of the container. For example, sealed glass ampules may contain one of more of the above reagents, or buffers that have been packaged under a neutral, non-reacting gas, such as nitrogen. Ampules may consist of any suitable material, such as glass, organic polymers, such as polycarbonate, polystyrene, etc.; ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

The kits may also contain other reagents and items useful for detecting ions. The reagents may standard solutions containing known quantities of the ion, dilution and other buffers, pretreatment reagents, etc. Other items which may be provided as part of the kit include a solid surface (for visualizing aggregate break down) such as a TLC silica plate, microporous materials, syringes, pipettes, cuvettes and containers. Standard charts indicating the appearance of the particles in various aggregation states, corresponding to the presence of different amounts of the ion under test, may be provided.

Kits may also be supplied with instructional materials. Instructions may be printed on paper or other substrate, and/or may be supplied as an electronic-readable medium, such as a floppy disc, CD-ROM, DVD–ROM, Zip disc, videotape, audiotape, etc. Detailed instructions may not be physically associated with the kit; instead, a user may be directed to an internet web site specified by the manufacturer or distributor of the kit, or supplied as electronic mail.

EXAMPLES

The following examples are included to demonstrate embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain like or similar results without departing from the spirit and scope of the invention.

Example 1

Preparation of Gold Particles

Gold colloids (13 nm diameter) were prepared by reduction of $HAuCl_4$ with citrate as described in Mirkin, U.S. Pat. No. 6,361,944, Frens, (1973) and Grabar, (1995). Briefly, all glassware was cleaned in aqua regia (3 parts HCl, 1 part $HNO_3$), rinsed with Nanopure $H_2O$, then oven dried prior to use. $HAuCl_4$ and sodium citrate were purchased from Aldrich Chemical Company. Aqueous $HAuCl_4$ (1 mM, 500 mL) was brought to reflux while stirring and 38.8 mM sodium citrate (50 mL) added quickly. The solution color changed from pale yellow to burgundy. Refluxing was continued for 15 min. After cooling to room temperature, the red solution was filtered through a Micron Separations Inc. 1 micron filter. Gold colloids were characterized by UV-vis spectroscopy using a Hewlett Packard 8452A diode array spectrophotometer and by Transmission Electron Microscopy (TEM) using a JEOL 2010 transmission electron microscope.

Example 2

In-vitro Selection of an Ion-dependent Deoxyribozyme

A partially random DNA library was used to obtain deoxyribozymes that cleave RNA in the presence of $Zn^{2+}$ or $Co^{2+}$.

Oligonucleotides

DNA oligonucleotides were purchased from Integrated DNA Technologies Inc., Coralville, Iowa. Sequences of the random DNA template and the primers (P1, P2 and P3) used in PCR amplifications are listed below:

```
P1:                                    (SEQ ID NO:3)
5'-GTGCCAAGCTTACCG-3'

P2:                                    (SEQ ID NO:4)
5'-CTGCAGAATTCTAATACGACTCACTATAGGAAGAGATGGCGAC-3'

P3:                                    (SEQ ID NO:5)
5'-GGGACGAATTCTAATACGACTCACTATrA-3'

Template for random DNA pool:          (SEQ ID NO:6)
5'-GTGCCAAGCTTACCGTCAC-N40-GAGATCTCGCCATCTCTTCCTAT
AGTGAGTCGTATTAG-3'
```

Primer P1b and P3b are the 5'-biotinylated version of primers P1 and P3. Primer P1a and P3a were prepared by 5'-labeling P1 and P3 with [□-$^{32}$P] ATP (Amersham) and T4 polynucleotide kinase (Gibco). The DNA/RNA chimeric substrate (17DS) for trans-cleavage assays has the sequence 5'-ACTCACTATrAGGAAGAGATG-3' (SEQ ID NO: 2), where rA denotes a single ribonucleotide. The all-RNA substrate (17RS) with the same sequence was purchased from Dharmacon Research Inc. The trans-cleaving deoxyribozyme 17E has the sequence 5'-CATCTCTTCTCCGAGC-CGGTCGAAATAGTGAGT-3' (SEQ ID NO:1). The deoxyribozyme named 17E1 is a variant of 17E with the sequence 5'-CATCTCTTTTGTCAGCGACTCGAAATAGTGAGT-3' (SEQ ID NO:7). All oligonucleotides were purified using denaturing polyacrylamide gel electrophoresis and desalted with the SepPak nucleic acid purification cartridges (Waters) before use.

Preparation of Random DNA Pool

The initial pool for DNA selection was prepared by template-directed extension followed by PCR amplification. The extension was carried out with 200 pmol of DNA template containing a 40-nucleotide random sequence region, and 400 pmol of primer P3b in 20×100 µl reaction mixtures for four thermal-cycles (1 min at 92° C., 1 min at 52° C., and 1 min at 72° C.). Reaction buffer also included 0.05 U/µl Taq polymerase (Gibco), 1.5 mM MgCl$_2$, 50 mM KCl, 10 mM Tris-HCl (pH 8.3 at 25° C.), 0.01% gelatin and 0.2 mM of each dNTP. Subsequently, 1 nmol each of P1 and P3b were added to the extension product to allow four more cycles of PCR amplification. The products were precipitated with ethanol and dissolved in 0.5 mL of buffer A, which contains 50 mM HEPES (pH 7.0), 500 mM (for Zn-DNA selection) or 1 M (for Co-DNA selection) NaCl. About 20 µM EDTA was also added to the buffer to chelate trace amount of divalent metal ion contaminants.

In Vitro Selection

The random DNA pool was immobilized on a NeutrAvidin column (Pierce) by incubating with the column materials for 30 minutes. The mixture was gently vortex-mixed a few times during the incubation. The unbound DNA strands were eluted with at least 5×100 µl of buffer A. The non-biotinylated strands of immobilized DNA were washed off the column with 5×100 µl of freshly prepared 0.2 M NaOH and 20 µM EDTA. The column was then neutralized with 5×100 µl of buffer A. The cleavage reaction was carried out by incubating the immobilized single-stranded DNA containing the single ribonucleotide (rA) with 3×20 µl of reaction buffer (buffer A plus 1 mM ZnCl$_2$ or CoCl$_2$) over 1 h. The eluted DNA molecules were pooled and precipitated with ethanol. A fraction of the selected DNA was amplified in 100 µl PCR reaction with 40 pmol each of primers P1 and P2 over 10$\tilde{~}$20 thermal cycles. One tenth of the PCR product was further amplified for six cycles with 50 pmol of primers P1 and P3b. The final PCR product was ethanol precipitated and used to initiate the next round of selection. During the selection of Zn(II)-dependent deoxyribozymes (called Zn-DNA hereafter), the concentration of ZnCl$_2$ was kept constant at 100 µM in the reaction buffer for the following rounds of selection. Reaction time was gradually decreased from 1 h to 30 s within 12 rounds of selection. For the selection of Co(II)-dependent deoxyribozymes (called Co-DNA hereafter), the concentration of CoCl$_2$ was gradually decreased from 1 mM to 100 µM and the reaction time from 1 h to 1 min within 10 rounds of selection. The twelfth generation of selectively amplified Zn-DNA and the tenth generation of Co-DNA were cloned using TA TOPO Cloning Kit (Invitrogen) and sequenced with T7 Sequenase 2.0 Quick-denatured Plasmid Sequencing Kit (Amersham).

Reselection

Based on the sequence of class I Zn-DNA or Co-DNA, partially degenerate DNA template libraries for reselection were synthesized (Integrated DNA Technology Inc., Coralville, Iowa) with 20% degeneracy at the N40 region. In other words, during the oligonucleotide synthesis of the N40 region, the wild type sequence was introduced at a probability of 80% at each position, while the other three nucleotides each occurred at a probability of 6.67%. The reselection pool was prepared with 10 pmol of template and 100 pmol of primers P1 and P3b using the same protocol previously described. With 10 pmol (number of molecules S=6×10$^{12}$) of partially randomized template, the statistic parameters of the DNA library used for reselection were calculated based on the following equations.

$$P(k,n,d)=[n!/(\tilde{n}k)!k!]d^k(\tilde{1}d)^{\tilde{n}k} \quad (1)$$

$$N(k)=[n!/(\tilde{n}k)!k!]3^k \quad (2)$$

$$C(n,k)=SP(k,n,d)/N(k) \quad (3)$$

P(k,n,d) is the probability of having k mutations within n (number of randomized positions, n=40) nucleotide positions that have been randomized at a degeneracy of d. N(k) is the number of distinct sequences that have k mutations with respect to the prototype sequence. C(n,k) is the number of copies for each sequence that has k mutations. The reselection pool was expected to contain the wild type sequence, all possible sequences with $\tilde{1}$8 point mutations, and a sampling of the sequences with >8 point mutations. More than half of the population contains $\geq$8 point-mutations. The protocol for reselection was the same as the primary selection, except that the reaction time was decreased from 20 min to 1 min and the concentration of ZnCl$_2$ or CoCl$_2$ was decreased from 20 µM to 5 µM over six generations. The sixth generation of reselected Zn- or Co-DNA were cloned and sequenced as previously described.

Kinetic Assays of the Reselected Cis-Cleaving DNA

The 5'$^{32}$P-labeled precursor DNA for cis-cleavage assay was prepared by PCR-amplification of the selected DNA population or the cloned DNA plasmid with primer 1b and 3a. The double-stranded product was immobilized on a NeutrAvidin column through the biotin moiety on primer P1b. The catalytic strand of DNA was eluted off the column with 3×20 µl freshly prepared 0.2 N NaOH and neutralized with 8 µl of 3 M sodium acetate (pH 5.3) in the presence of 50 µg/ml bovine serum albumin (Sigma). Following ethanol precipitation, the single-stranded DNA was purified on an 8% denaturing polyacrylamide gel and desalted with SepPak nucleic acid purification cartridge. Bovine serum albumin (50 µg/ml) was added to the gel-soaking buffer (0.2 M NaCl, 20 µM EDTA, 10 mM TRisHCl, pH 7.5) to prevent the DNA from adhering to the tube. The concentration of the DNA was determined by scintillation counting the radioactivity.

The precursor DNA was dissolved in buffer A and incubated at room temperature for 10 min before $CoCl_2$ or $ZnCl_2$ was added. The reaction was stopped with 50 mM EDTA, 90% formamide and 0.02% bromophenol blue. Reaction products were separated on an 8% denaturing polyacrylamide gel and quantified with a Molecular Dynamic phosphorimager.

In Vitro Selection of Zn(II)- or Co(II)-Dependent Deoxyribozymes

The DNA molecules capable of cleaving an RNA bond in the presence of $Co^{2+}$ or $Zn^{2+}$ were obtained through in vitro selection. The initial DNA library for selection contains ~$10^{14}$ out of the possible $10^{24}$ (=$4^{40}$) DNA sequences. These molecules consist of a random sequence domain of 40 nucleotides flanked by two conserved primer-binding regions. The sequence of the conserved region was designed in such a way that they could form two potential substrate-binding regions (FIG. 1A). A ribonucleic adenosine was embedded in the 5'-conserved sequence region and was intended to be the cleavage site, since an RNA bond is more susceptible than a DNA bond toward hydrolytic cleavage. The intrinsic half-life of the phosphodiester linkage in RNA at pH 7 and 25° C. is estimated to be 1,000 years. The corresponding value for DNA is 200 million years.

Figure 1B:
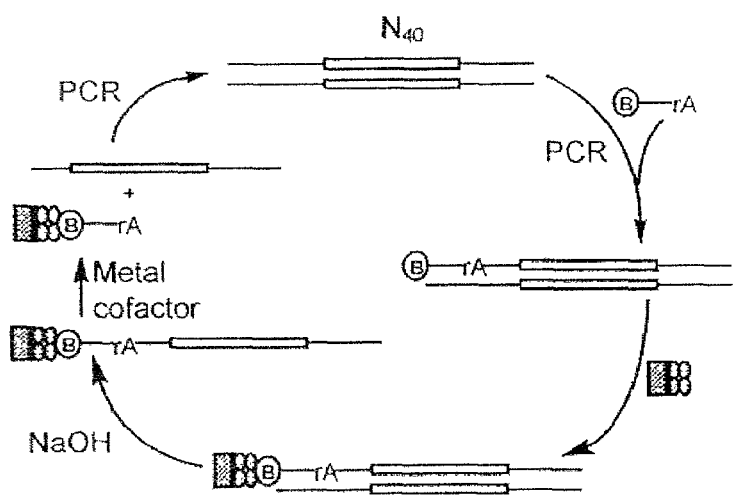
FIG. 1B. Selective amplification scheme for isolation of DNA that catalyzes the metal cofactor ($Co^{2+}$ or $Zn^{2+}$) dependent cleavage of an RNA phosphodiester.

The DNA pool was immobilized on a NeutrAvidin column through the biotin moiety on the 5' terminus of the DNA. Biotin and Avidin bind strongly with an association constant of $K_a=10^{15}$ $M^{-1}$. The sequences that underwent self-cleavage in the presence of $Co^{2+}$ or $Zn^{2+}$ were eluted off the column, amplified and used to seed the next round of selection (FIG. 1B). The selection stringency was increased during the selection process with shorter reaction time and less available divalent metal ions. The activity of the selected Zn-DNA gradually increased until the twelfth generation and declined thereafter, while the highest activity was achieved with the tenth generation of Co-DNA. Therefore the twelfth generation of Zn-DNA and the tenth generation of Co-DNA were cloned and sequenced. The cloned sequences can be divided into different classes based on sequence similarity (FIG. 2 and FIG. 3).

Individual sequences of the cloned Zn-DNA and Co-DNA were randomly chosen and sampled for activity. Under the selection conditions (100 µM $Zn^{2+}$, 500 mM NaCl, 50 mM HEPES, pH 7.0, 25° C.), the observed rate constants of Zn-DNAs from sequence-classes I and II were 0.1̃0.2 $min^{-1}$, while class III sequences were less active, with $k_{obs}$ around 0.02 $min^{-1}$. The cleavage rate of the initial pool was $2 \times 10^{-7}$ $min^{-1}$. Therefore, a $10^{-5}10^6$ fold increase in cleavage rate has been achieve for Zn-DNA selection. The cleavage rates of all the randomly picked Co-DNA sequences were <0.02 $min^{-1}$ under the conditions for Co-DNA selections (100 µM $Co^{2+}$, 1 M NaCl, 50 mM HEPES, pH 7.0, 25° C.). Interestingly, even in the buffer (1 M NaCl, 50 mM HEPES, pH 7.0) alone, the class II Co-DNA exhibited similar activity as in the presence of 100 µM $Co^{2+}$ or $Zn^{2+}$.

Clone #5 of Zn-DNA (Zn-5) and clone #18 of Co-DNA (Co-18) showed relatively high activity, as well as high frequency of occurrence, within their lineages. The $k_{obs}$ were 0.17 $min^{-1}$ for Zn-5 (in 100 µM $Zn^{2+}$) and 0.02 $min^-$ for Co-18 (in 100 µM $Co^{2+}$). The sequences of Zn-5 and Co-18 were partially randomized (see Material and Methods for details) and subjected to reselection in order to further improve the reactivity and metal-binding affinity, and to explore the sequence requirement of the conserved catalytic motif. Based on equations (1)(3), the reselection pool was expected to contain the wild type sequence, all possible sequences with 1̃8 point mutations, and a sampling of the sequences with >8 point mutations. More than half of the population should contain ≧8 point mutations. Six rounds of reselection were carried out with 5̃20 µM $Zn^{2+}$ or $Co^{2+}$, however the activity of the reselected DNA was similar to the activity of the wild type sequences. Sequencing of the Zn-DNA from both the initial selection and reselection revealed a highly conserved sequence region. Therefore the lack of activity improvement after reselection likely reflects a sequence pool dominated by a few highly reactive sequences.

Sequence Alignment and Structure Analysis of Zn-DNA

The sequences of thirty individual clones of initially selected Zn-DNA can be divided into three major classes based on sequence similarity. Differences among members of each class were limited to a few point mutations (FIG. 2). A highly conserved sequence region of 20 nt, 5'-TX$_1$X$_2$X$_3$AGCY$_1$Y$_2$Y$_3$TCGAAATAGT-3' (SEQ ID NO:8) (Region-20 nt), was observed in all but one sequence albeit at different locations. The sequences of 5'-X$_1$X$_2$X$_3$-3' and 3'-Y$_3$Y$_2$Y$_1$-5' are complimentary and covariant, indicating that they form base pair with each other:

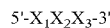

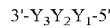

The secondary structures of the sequenced Zn-DNA were predicted using Zuker's DNA mfold program (see http://mfold.wustl.edu/~folder/dna/form1.cgi) through minimization of folding energy. The most stable structures predicted for those containing Region-20nt all contained a similar structure motif. This common motif consists of a pistol-shaped three-way helical junction formed by a 3 bp hairpin, an 8 bp hairpin and a double helix linking to the rest of the molecule. The 3 bp hairpin and its adjacent single-stranded regions are part of the Region-20nt. The ribonucleic adenosine is unpaired and positioned opposite of the 3 bp hairpin.

Figure 4:
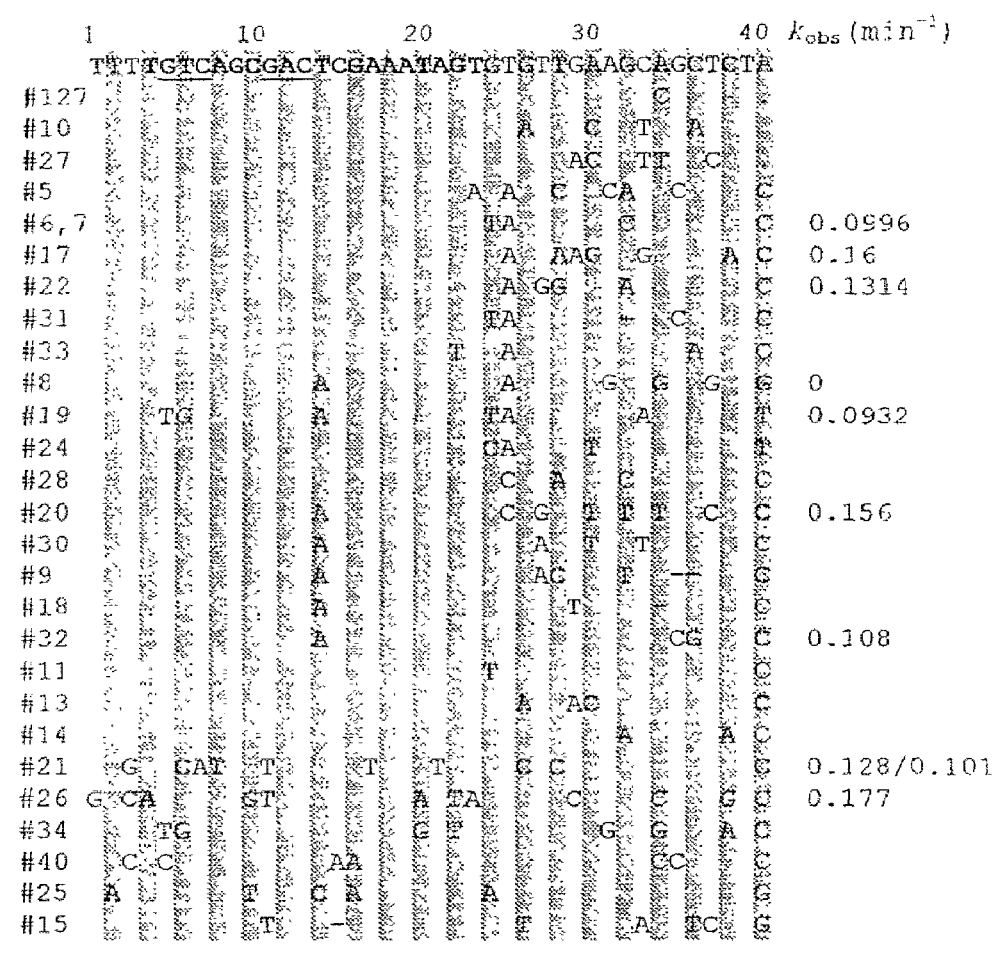

After reselection, twenty-eight Zn-DNA clones were sequenced (FIG. 4). When compared with the parental wild type sequence (class I Zn-DNA), the reselected Zn-DNA contained point mutations mostly outside of Region-20nt. About one third of these sequences have a T→A mutation at position 73, converting the T̃T mismatch in the wild type sequence to a WatsoñCrick base pair. In one fourth of the reselected DNAs, the 5 nucleotide single-stranded bulge of the three-way junction has the sequence 5'-ACGAA-3', corresponding to 5'-TCGAA-3' in the wild type. Clone #17 (named ZnR17) of the reselected Zn-DNA is most active under selection conditions (FIG. 4). Structural analysis of ZnR17 revealed two completed base-paired helices in the three-way junction. Therefore, it was engineered into a trans-cleaving deoxyribozyme by deleting the sequences outside of the three-way junction and the loop of the 8 bp hairpin. Such truncation resulted in two individual stands, which hybridize with each other through two 9-10 bp helices. The strand containing the single ribonucleotide residue (rA) is considered as the substrate (named 17DS), while the other strand as the enzyme (named 17E). The catalytic core, which was highly conserved during selection, consists of a 3 bp hairpin and a 5 nt single-stranded bulge (FIG. 5).

Although ZnR17 was selected in $Zn^{2+}$, it does not contain structure motifs that were discovered in several Zn(II)-binding RNA molecules (Ciesiolka et al., 1995; Ciesiolka & Yarus, 1996). However, the conserved region of ZnR17 is very similar to that of the $\widetilde{8}17$ deoxyribozymes selected by Santoro and Joyce using $Mg^{2+}$ as cofactor (Santoro & Joyce, 1997). The unpaired bulge region in the $\widetilde{8}17$ DNA enzyme has the sequence 5'-WCGR-3' or 5'-WCGAA-3' (W=A or T; R=A or G). The highest activity was observed with the sequence containing 5'-TCGAA-3'. Among the Zn(II)-dependent deoxyribozymes we obtained after reselection, 85% of them fell within the 5'-WCGAA-3' regime (W=A or T). However, the sequence of the two double helices flanking the catalytic core is different between the $\widetilde{8}17$ (FIG. 6D) and the 17E deoxyribozymes (FIG. 6F), reflecting their different designs of the selection pool. Similar sequence motif was also observed in an RNA-cleaving deoxyribozyme (named Mg5) selected by Faulhammer and Famulok using 50 mM histidine and 0.5 mM $Mg^{2+}$ as cofactors (Faulhammer & Famulok, 1997). The homologous region in 31 out of the 44 sequenced clones had the sequence 5'-$TX_1X_2X_3AGCY_1Y_2Y_3ACGAA$-3' (SEQ ID NO:9), falling within the WCGAA-3' regime. The authors predicted a secondary structure different from the $\widetilde{8}17$ or 17E motif based on chemical modification analysis. However, a structure containing a three-way junction similar to that of the 17E and $\widetilde{8}17$ deoxyribozymes is consistent with the chemical mapping results.

Sequence Alignment and Structure Analysis of Co-DNA

The sequences of the cis-cleaving deoxyribozyme selected in the presence of $Co^{2+}$ are more diverse than the Zn-DNA. They can be divided into three major classes based on sequence similarity (FIG. 3). There is no consensus sequence region among different classes. The secondary structure of each sequence class of Co-DNA was predicted with DNA mfold program. The minimal conserved sequence motif of class I Co-DNA includes a bulged duplex. The cleavage site is within the 13 nt single-stranded bulge. A 4 bp hairpin is also highly conserved and linked to the bulged duplex through 3 unpaired nucleotides. The folding of the sequences outside of this minimal motif was highly variable and resulted in structures with a wide range of stabilization energy.

Figure 7A:
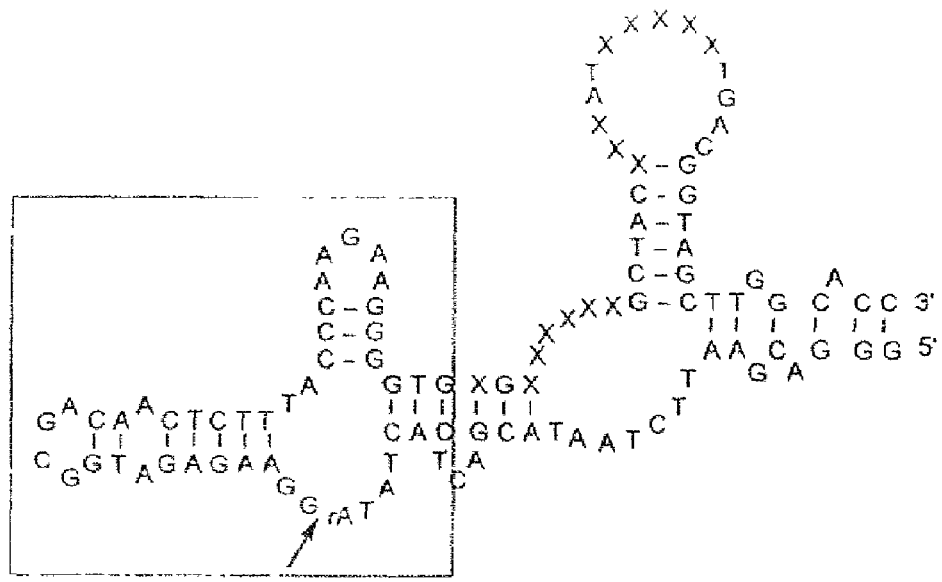
FIG. 7A. (SEQ ID NO: 83) The predicted secondary structure of the G3 deoxyribozyme (Geyer & Sen, 1997).
Figure 7B:
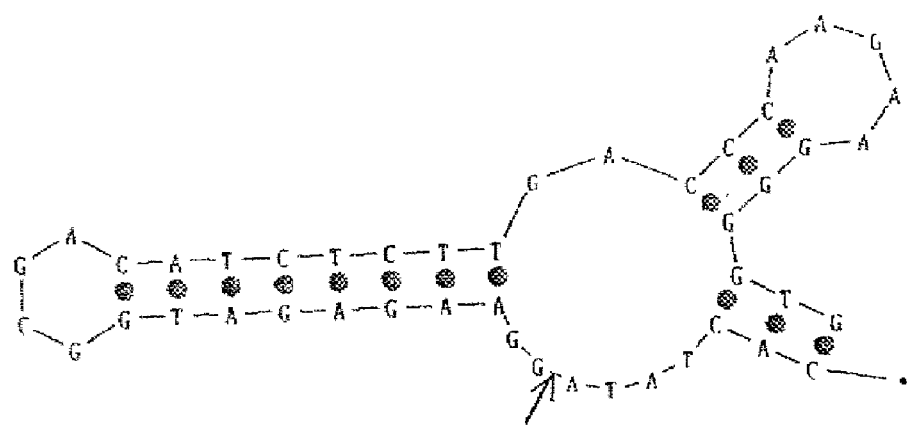
FIG. 7B. (SEQ ID NO: 84) The minimal structure motif of the class II Co-DNA predicted by mfold program. The arrows indicate the cleavage sites.

The class II Co-DNA contains a sequence region (5'-ACCAAGAAGGGGTG-3' (SEQ ID NO:10)) that was also found in an RNA-cleaving deoxyribozyme (termed G3) selected by Geyer and Sen (1997) (FIG. 7A and 7B). The minimal motif predicted for class II Co-DNA shows similarity to that proposed for the G3 deoxyribozyme as well. The G3 deoxyribozyme was believed to be fully active in the absence of any divalent metal ions. Copious use of divalent metal chelating agents, such as EDTA, and accurate trace-metal analysis of the reaction solutions were used to rule out the need of the G3 deoxyribozyme for contaminating levels of divalent metals. As mentioned earlier, the activity of class II Co-DNA was the same in buffer alone or with added $Co^{2+}$ or $Zn^{2+}$, suggesting that this class of Co-DNA most likely contain the divalent metal-independent structure motif.

Effect of Metal Ions on the Activity of the Cis-Cleaving Deoxyribozymes

ZnR17 and Co-18 were examined for their activity dependence on monovalent ions and divalent metal ions other than $Zn^{2+}$ and $Co^{2+}$. In the presence of 1 mM EDTA and without added $Zn^{2+}$ ions, no cleavage was observed with ZnR17 even after two days, strongly suggesting that divalent metal ions are required for the activity of ZnR17. Although the cis-cleaving Zn-DNA was selected in the presence of 500 mM NaCl, NaCl was actually inhibitory to enzymatic activity. With 0-2 M NaCl added to the reaction buffer (100 μM $Zn^{2+}$, 50 mM HEPES, pH 7.0), $k_{obs}$ decreased with increasing NaCl concentration. The deleterious effect of NaCl was also manifested by lowered final percentage of cleavage products. For instance, only 50% of ZnR17 could be cleaved in the presence of 2 M NaCl even after long incubation times, while >95% of the DNA was cleavable in the absence of extra NaCl. Contrary to the Zn-DNA, the activity of Co-18 relies on NaCl and no cleavage was observed in the absence of NaCl. With 1 M NaCl, 8% of Co-18 molecules were cleaved within 5 min, while <0.2% were cleaved in the absence of extra NaCl.

Although the deoxyribozymes were selected using either zinc or cobalt as cofactor, they are also active in other transition metal ions and in $Pb^{2+}$. The cleavage efficiency of ZnR17 followed the trend of $Pb^{2+}$>$Zn^{2+}$>$Mn^{2+}$~$Co^{2+}$~$Ca^{2+}$~$Cd^{2+}$>>$Ni^{2+}$>$Mg^{2+}$. It is noteworthy that the cleavage rate in $Ca^{2+}$ was much higher than in $Mg^{2+}$, a similar trend was observed with the Mg5 deoxyribozyme. The order of Co-18 activity is as follow: $Zn^{2+}$>$Pb^{2+}$~$Co^{2+}$>$Ni^{2+}$>$Cd^{2+}$~$Mn^{2+}$>$Mg^{2+}$~$Ca^{2+}$. In general, both ZnR17 and Co-18 are more active in transition metal ions than in alkaline-earth metals, and higher activities were achieved with $Pb^{2+}$, $Co^{2+}$ and $Zn^{2+}$. The preference of the selected deoxyribozymes for $Co^{2+}$ and $Zn^{2+}$ reflected their selection criteria. A similar trend ($Pb^{2+}$>$Zn^{2+}$>$Mn^{2+}$>$Mg^{2+}$) was also observed with all four RNA-cleaving deoxyribozymes selected in parallel by Breaker and Joyce using one of the four metal ions ($Pb^{2+}$, $Zn^{2+}$, $Mn^{2+}$, $Mg^{2+}$) as cofactor (1995). The proposed secondary structures of the deoxyribozymes selected in $Pb^{2+}$ and $Mg^{2+}$ have been reported (Breaker & Joyce, 1994, 1995). No structure similarity was observed between ZnR17 and those RNA-cleaving deoxyribozymes.

SUMMARY

Using in vitro selection technique, several groups of RNA-cleaving deoxyribozymes were isolated using $Zn^{2+}$ or $Co^{2+}$ as cofactor. No common sequence or structural features were observed between the Co(II)-dependent and the Zn(II)-dependent deoxyribozymes, in spite of the chemical similarities between these two transition metal ions. The deoxyribozymes selected in $Zn^{2+}$ share a common motif with the $\widetilde{8}17$ and the Mg5 deoxyribozymes isolated under different conditions, including the use of different cofactors. Both the Co-DNA and the Zn-DNA exhibited higher activity in the presence of transition metal ions than in alkaline earth metal ions, which are the most commonly adopted metal cofactors by naturally occurring ribozymes.

Example 3

Deoxyribozyme Based Biosensor for $Pb^{2+}$ Detection

This Example describes a particle-based biosensor for the detection of $Pb^{2+}$. The biosensor utilizes the deoxyribozyme developed in Example 2 (termed 17E) combined with particle technology to allow quantitative and real time measurements of catalytic activity. Because catalytic activity is dependent on $Pb^{2+}$, the biosensor provides real-time, quantitative, and sensitive measurements of $Pb^{2+}$ concentrations.

DNA/RNA Chimera Oligonucleotide Cleavable Substrate.

The oligonucleotides were purchased from Integrated DNA Technology, Inc, Coralville, Iowa. The cleavable substrate is a 44 base DNA/RNA chimera oligonucleotide with the sequence 5'-TGTCAACTCGTG-ACTCACTATrAG-GAAGAGATG-TGTCAACTCGTG-3'(SEQ ID NO:85) ), in which rA represents a ribonucleotide adenosine. The cleavable substrate strand is derived from the substrate 17DS 5'-ACTCACTATrAGGAAGAGATG-3' (SEQ ID NO:2) (See Example 2). 17DS has been extended on both the 3' and 5' ends for twelve bases, which act as "sticky end" for annealing to a complementary DNA strand on the gold particles.

Thiol-Modified DNA Gold Particles.

Thiol-modified oligonucleotides were purchased from Integrated DNA Technology, Inc, Coralville, Iowa. A thiol-modified 12mer DNA primer, 5'-SH—$(CH_2)_6$-CACGAGT-TGACA-3'(SEQ ID NO:86) was attached to the 13 nm diameter gold particles (produced as in Example 1) by adding the 3.6 µM thiol-modified DNA to the gold colloid. The solution was allowed to sit for 24 hrs, and then diluted to give a final concentration of 100 mM NaCl and 25 mM Tris-acetate buffer, pH 7.2. After another 24 hrs, the DNA attached gold particles were centrifuged at 14,000 rpm for one hour. The supernatant was removed and the concentrated gold particles washed with 100 mM NaCl buffer. After another centrifuge at 14,000 rpm, the particles were stored in 300 mM NaCl, 25 mM Tris-acetate buffer.

Preparation of Agglutinated Gold Particles.

500 pmol cleavable substrate and 1,000 pmol trans-cleaving deoxyribozyme (17-E) were added to DNA linked gold particles (absorption of 2.2 at 522 nm) to a final volume of 3 mL. The sample was buffered at pH 7.2 using 25 mM Tris-acetate (TA) and 500 mM NaCl. The mixture was heated to 70° C. and allowed to cool slowly to room temperature. A dark purple precipitation was formed at the bottom of the tube. This is due to the aggregation of 13 nm gold particles by the DNA linker. After centrifugation for one minute, the precipitation were collected and resuspended in 4 mL of 300 mM NaCl, 25 mM TA buffer pH7.2.

The trans-cleaving deoxyribozyme is required for aggregate formation. Without the deoxyribozyme, the DNA modified gold particles and cleavable substrate did not aggregate. A deoxyribozyme titration experiment was performed to determine the optimum ratio of deoxyribozyme and cleavable substrate. The extinction at 522 nm was shown to represent the relative amount of separated gold particles while the extinction at 700 nm was shown to represent the relative amount of gold particle aggregates. Hence, the ratio of extinction at 700 nm to 522 nm was used to monitor the degree of aggregation. This procedure minimized artifacts due to concentration differences. Aggregation increased with deoxyribozyme concentration until the ratio of deoxyribozyme to µ reached one.

UV-Vis Extinction Spectrum of Separated and Aggregated Gold Particles

The UV-vis extinction spectrum of separated and aggregated gold particles was determined as follows. Gold particles were prepared as in Example 1. Aggregated gold particles were prepared as in Example 3. UV-vis extinction spectra were obtained by monitoring the surface plasmon band of gold nanoparticles. For an non-aggregated particles, the extinction peak is 522 nm and decreases rapidly at longer wavelengths, giving the suspension a deep red color. When the particles are in the aggregated state, the extinction peak shifts to a longer wavelength and falls off less quickly. A suspension of aggregated particles develops a purple color.

Example 4

Color Change of the $Pb^{2+}$ Sensor in the Presence of $Pb^{2+}$ Due to Enzymatic Substrate Cleavage To verify that the cleavage is carried out by the deoxyribozyme 17E and using $Pb^{2+}$ only as a cofactor, a control experiment replacing 17E with an inactive deoxyribozyme 17E-C: 5'-CATCTCTTCCCCGAGCCGGTCGAAAT-AGTGAGT-3' (SEQ ID NO:87) was performed. Previous kinetics assays have shown that the activity of 17E was complete lost when the G•T wobble pair was replaced by a G•C Watson-Crick base pair. (Santoro, S. W. & Joyce, G. F. (1997); Faulhammer, D. & Famulok, M. (1997).) 17E-C is an inactive version of 17E by changing the important T base to a C base. Since only one base is changed, the structure of the substrate-17E duplex is very similar to the duplex formed by the substrate and 17E-C.

Aggregated particles were prepared as in Example 3. In addition, aggregated particles containing the inactive deoxyribozyme, 17E-C instead of the active deoxyribozyme were also prepared using the same method. A $Pb^{2+}$ assay was then performed as follows. 48 µL of particle suspension was pipetted into microcentrifuge tubes. 2 µL of a 5 µM$Pb^{2+}$ standard ($Pb(OAc)_2$ (Aldrich, St. Louis, Mo.) in water) was added to each tube and the tubes heated above 50° C. for 5 minutes. The melting temperature of the aggregated particles was previously determined by measuring the extinction at 260 nm. The DNA linked gold particles showed a sharp melting temperature (46° C.). Thus, heating the aggregated particles to a temperature higher than 50° C. resulted in the fully melting of the aggregate.

The tubes were allowed to cool naturally to room temperature and UV-vis spectra measured. When active deoxyribozyme was present, cleavage of the substrate was observed at 5 µM $Pb^{2+}$. However, with inactive deoxyribozyme, cleavage was not observed, even in the presence of 5 µM $Pb^{2+}$.

Example 5

Semi-quantitative and Quantitative DNA $Pb^{2+}$ Assays

Semi-quantitative protocol—An assay was performed as in the previous example. After the tubes cooled at room temperature, a 10 µL sample was removed and used to spot on an alumina TLC plate (Analtech, Newark, Del.). A color progression from purple (no lead present) to red (high lead concentration) was observed. Hence, the $Pb^{2+}$ concentration in a sample may be determined by comparing the color obtained with the sample with that obtained for standard $Pb^{2+}$ solutions or with a standard color Quantitative protocol—After the tubes cooled at room temperature UV-vis spectra were obtained using a Hewlett-Packard 8453 spectrophotometer. To eliminate the effect of concentration, the ratio of extinction at 522 nm and 700 nm was used to monitor the degree of aggregation of particles. These two wavelengths were chosen to represent the relative amount of aggregated and free gold particles.

Example 6

Detection Range of a DNA $Pb^{2+}$ Assay

Agglutinated gold particles were prepared as in Example 3 except that a 1 to 1 ratio of deoxyribozyme to substrate was used. A $Pb^{2+}$ assay was performed as in Example 4. $Pb^{2+}$ standards in the range 0-5 µM were tested and the results visualized on a TLC plate and by UV-vis extinction spectroscopy. $Pb^{2+}$ standards in the range from 250 nM to 1 µM were distinguishable visually on the plate. A second assay was performed using a 1 to 20 mixture of active and inactive deoxyribozyme. Here, the assay the detection region was from 10 µM-200 µM. Hence, by simply varying the amount of active deoxyribozyme, the detection range of the assay may be varied to adopt to different detection requirements. In addition to visual detection, results were determined quantitatively using the ratio of extinction at 522 nm and 700 nm.

Example 7

Cross-reactivity Characteristics of a DNA $Pb^{2+}$ Assay

Standards containing 5 µM $Pb^{2+}$, $Mg^{2+}$, $Mn^{2+}$, $Co^{2+}$, $Ni^{2+}$, $Cu^{2+}$, $Zn^{2+}$ and $Cd^{2+}$ ions in water were prepared by dissolving $Pb(OAc)_2$, $MgCl_2$, $MnCl_2$, $CoI_2$, $NiCl_2$, $CuCl_2$, $ZnCl_2$, and $Cd(OAc)_2$ (Aldrich, St. Louis, Mo.) in water. A $Pb^{2+}$ assay was performed as in Example 4 to determine the cross-reactivity of 5 µM $Mg^{2+}$, $Mn^{2+}$, $Co^{2+}$, $Ni^{2+}$, $Cu^{2+}$, $Zn^{2+}$ and $Cd^{2+}$. The standards containing these ions were tested along with the standard containing 5 µM $Pb^{2+}$. These divalent metal ions are chosen for assay because they have shown relative high activities as a metal cofactor for enzymatic cleavage. At 5 µM, all seven metal ions give a blue color on a TLC plate. However, 0.5 µM $Pb^{2+}$ developed a purple color. In addition, results were determined quantitatively using the ratio of extinction at 522 nm and 700 nm. The results obtained with $Mg^{2+}$, $Co^{2+}$, and $Zn^{2+}$ are shown in Table 3. Of the ions tested, $Zn^{2+}$ and $Co^{2+}$ showed the highest cross reactivity.

TABLE 3

Detection of $Pb^{2+}$ in the presence of $Mg^{2+}$, $Co^{2+}$, and $Zn^{2+}$ ions.

| Sample Name | Extinction at 522 nm | Extinction at 700 nm | E522/E700 |
|---|---|---|---|
| pure water | 0.91982 | 0.43821 | 2.099 |
| 1 µM $Pb^{2+}$ | 1.0839 | 0.17929 | 6.045 |
| 1 µM $Pb^{2+}$ + 1 µM $Co^{2+}$ | 1.0844 | 0.1582 | 6.854 |
| 1 µM $Pb^{2+}$ + 1 µM $Mg^{2+}$ | 1.0911 | 0.1739 | 6.274 |
| 1 µM $Pb^{2+}$ + 1 µM $Zn^{2+}$ | 1.1691 | 0.12972 | 9.0124 |

Example 8

Room Temperature DNA $Pb^{2+}$ Assay. (Prophetic)

This example describes a room temperature DNA $Pb^{2+}$ Assay. Thiol-modified oligonucleotides may be purchased from Integrated DNA Technology, Inc., Coralville, Iowa. The thiol-modified 12mer DNA primer, 5'-SH—$(CH_2)_6$-CAC-GAGTTGACA-3'(SEQ ID NO:88) is used to modify gold particles as in Example 3. In addition, a second type to modified gold particles are produced using the same primer sequence but with a 3'-thiol linkage. Agglutinated gold particles are prepared using the method described in Example 3 except that a 1:1 mixture of 3'-thiol and 5'-thiol DNA linked particles is used.

A $Pb^{2+}$ assay is then performed as follows. 48 µL of particle suspension is pipetted into microcentrifuge tubes. 2 µL of a $Pb^{2+}$ standard is added to each tube and the tubes incubated at room temperature. The UV-vis extinction spectra are then determined. A breakdown of aggregation is observed with increasing $Pb^{2+}$ concentration. Thus, the modified assay does not require the heating and cooling steps of the unmodified assay.

Example 9

Detection of Pb2+ in Leaded Paint

The DNA based sensor was used to detect $Pb^{2+}$ in leaded paint. Leaded paint containing various concentrations of lead was simulated by adding basic lead carbonate 0%, 0.5%, 1%, 2%, 3%, 5% 10% by weight of $PbCO_3.Pb(OH)_2$ (Aldrich, St. Louis, Mo.) to a commercial white paint containing a $TiO_2$ pigment. (Exterior white paint, Glidden, Cleveland, Ohio). The leaded paint was dissolved in 10% HOAc. After diluting this solution 150000 times in water, a $Pb^{2+}$ assay was performed. Results were determined in a modified semi-quantitative protocol. Briefly, 2 µL of 50 times concentrated aggregated particles (prepared as in Example 3) were added to 98 µL of the diluted paint solution. This mixture was then heated to 50° C. for 5 minutes and allowed to cool slowly to room temperature. A 10 µL sample was spotted onto a TLC plate. A color pattern developed on the TLC plate showing a color transition between 2 and 3% indicating that the $Pb^{2+}$ concentrations in the original solutions is approximately 500 nM. With the knowledge of the times of dilution, the concentration of the original soaking solution can be calculated.

REFERENCES

Allara and Nuzzo, Langmuir, 1, 45 (1985).
Allara and Tompkins, (1974) J. Colloid Interface Sci., 49, 410-421.
Bain & Whitesides, (1989) Angew. Chem. Rev. Ed. Eng., 28, 506-512.
Breaker, R. R.; Joyce, G. F. Chem. Biol. 1995, 2, 655-660.
Breaker, R. R. & Joyce, G. F. (1994) A DNA enzyme that cleaves RNA. Chem. Biol. 1, 223-229.
Breaker, R. R. (1997) DNA enzymes. Nat. Biotechnol. 15, 427-431.
Brust et al., (1995) Adv. Mater., 7, 795-797.
Burwell, (1974) Chemical Technology, 4, 370-377.
Cadwell, R. C.; Joyce, G. F. PCR Methods Appl. 1992, 2, 28-33.
Cadwell, R. C.; Joyce, G. F. PCR Methods Appl. 1994, 3, S136-S140.
Carmi, N., Shultz, L. A. & Breaker, R. R. (1996) In vitro selection of self-cleaving DNAs. Chem. Biol. 3, 1039-1046.
Chapman, K. B.; Szostak, J. W. Curr. Opin. Struct. Biol. 1994, 4, 618-622.
Chen et al., J. Am Chem. Soc., (1989) 111, 6402-6407.
Chen & Seeman, Nature, (1991) 350, 631-633.
Chen et al., (1994) Biochem., 33, 13540-13546.
Ciesiolka, J.; Gorski, J.; Yarus, M. RNA 1995,1, 538-550.
Ciesiolka, J.; Yarus, M. RNA 1996, 2, 785-793.
Conaty, J.; Hendry, P.; Lockett, T. Nucleic Acids Res. 1999, 27, 2400-2407.
Conn, M. M.; Prudent, J. R.; Schultz, P. G. J. Am. Chem. Soc. 1996, 118, 7012-7013.
Cuenoud, B. & Szostak, J. W. A DNA metalloenzyme with DNA ligase activity. Nature 375, 611-614 (1995).

Dai, X.; De Mesmaeker, A.; Joyce, G. F. *Science* 1995, 267, 237-240.

Deo, S. & Godwin, H. A. A Selective, Ratiometric Fluorescent Sensor for $Pb^{2+}$. *J. Am. Chem. Soc.* 122, 174-175 (2000).

Dubois & Nuzzo, (1992) Annu. Rev. Phys. Chem., 43, 437-464.

Earnshaw & Gait, "Modified Oligoribonucleotides as site-specific probes of RNA structure and function," *Biopolymers* (John Wiley & Sons, Inc.) 48:39-55, 1998.

Ekland, E. H.; Szostak, J. W.; Bartel, D. P. *Science* 1995, 269, 364-370.

Ekland, E. H.; Bartel, D. P. *Nature* 1996, 382, 373-376.

Famulok, M. *Curr. Opin. Struct. Biol.* 1999, 9, 324-329.

Faulhammer, D.; Famulok, M. *Angew. Chem., Int. Ed. Engl.* 1997, 35, 2837-2841.

Frank, D. N.; Pace, N. R. *Proc. Natl. Acad. Sci. U. S. A.* 1997, 94, 14355-14360.

Frens, (1973) Nature Phys. Sci., 241, 20.

Geyer, C. R.; Sen, D. *Chem. Biol.* 1997, 4, 579-593.

Grabar, K. C. et al., (1995) Anal. Chem., 67(4), 735-743.

Hennrich, G.; Sonnenschein, H.; Resch-Genger, U. *J. Am. Chem. Soc.* 1999, 121, 5073-5074.

Iler, The Chemistry Of Silica, Chapter 6, (Wiley 1979).

Illangasekare, M.; Yarus, M. *J. Mol. Biol.* 1997, 268, 631-639.

Jhaveri, et al., Designed Signaling Aptamers that Transduce Molecular Recognition to Changes in Fluorescence Intensity, *Journal of the American Chemical Society;* 2000; 122(11); 2469-2473.

Joyce, G. F. *Curr. Opin. Struct. Biol.* 1994, 4, 331-336.

Koizumi, M.; Soukup, G. A.; Kerr, J. N. Q.; Breaker, R. R. *Nat. Struct. Biol.* 1999, 6, 1062-1071.

Lee, M., & Walt, D. R. A fiber-optic microarray biosensor using aptamers as receptors. *Anal Biochem* 282(1):142-146, 2000.

Lehman, N.; Joyce, G. F. *Nature* 1993, 361, 182-185.

Li, J., Zheng, W., Kwon, A. H. & Lu, Y. In vitro selection and characterization of a highly efficient Zn(II)-dependent RNA-cleaving deoxyribozyme. *Nucleic Acids Res.* 28, 481-488 (2000).

Li, Y.; Sen, D. *Nat. Struct. Biol.* 1996, 3, 743-747.

Li, Y.; Breaker, R. R. *Proc. Natl. Acad. Sci. U S. A.* 1999, 96, 2746-2751.

Li, Y.; Liu, Y.; Breaker, R. R. *Biochemistry* 2000, 39, 3106-3114.

Lohse, P. A.; Szostak, J. W. *Nature* 1996, 381, 442-444.

Lorsch, J. R.; Szostak, J. W. *Nature* 1994, 371, 31-36.

Maoz and Sagiv, (1987) Langmuir, 3, 1034.

Marsh et al., (1995) Nucleic Acids Res., 23, 696-700.

Matteucci and Caruthers, (1981) J. Am. Chem. Soc., 103, 3185-3191.

Mirkin et al. (U.S. Pat. No. 6,361,944)

Mirkin, (1994) Annu. Review Biophys. Biomol. Struct., 23, 541-576.

Mucic et al., (1996) Chem. Commun. 555-557.

Nuzzo et al., J. Am. Chem. Soc., 109, 2358 (1987).

Oehme, I. & Wolfbeis, O. S. Optical sensors for determination of heavy metal ions. *Mikrochim. Acta* 126, 177-192 (1997).

Pan, T. & Uhlenbeck, O. C. A small metalloribozyme with a two-step mechanism. *Nature* 358, 560-563 (1992).

Pan, T.; Dichtl, B.; Uhlenbeck, O. C. Biochemistry 1994, 33, 9561-9565.

Pearce, D. A.; Walkup, G. K.; Imperiali, B. *Bioorg. Med Chem. Lett.* 1998, 8, 1963-1968.

Piccirilli, J. A.; McConnell, T. S.; Zaug, A. J.; Noller, H. F.; Cech, T. R. *Science* 1992, 256, 1420-1424.

Pley, H. W.; Flaherty, K. M.; McKay, D. B. *Nature* 1994, 372, 68-74.

Potyrailo, R. A.; Conrad, R. C.; Ellington, A. D.; Hieftje, G. M. *Anal. Chem.* 1998, 70, 3419-3425.

Potyrailo, R. A., Conrad, R. C., Ellington, A. D. & Hieftje, G. M. (1999). Adapting Selected Nucleic Acid Ligands (Aptamers) to Biosensors. *Anal. Chem.* 70: 3419-3425.

Prudent, J. R.; Uno, T.; Schultz, P. G. *Science* 1994, 264, 1924-1927.

Robertson, M. P.; Ellington, A. D. *Nat. Biotechnol.* 1999, 17, 62-66.

Robertson, M. P.; Ellington, A. D. *Nucleic Acids Res.* 2000, 28, 1751-1759.

Roth, A.; Breaker, R. R. *Proc. Natl. Acad Sci. U. S. A.* 1998, 95, 6027-6031.

Rurack, K., Kollmannsberger, M., Resch-Genger, U. & Daub, J. A Selective and Sensitive Fluoroionophore for HgII, AgI, and CuII with Virtually Decoupled Fluorophore and Receptor Units. *J. Am. Chem. Soc.* 122, 968-969 (2000).

Sambrook et al., Molecular Cloning: A Laboratory Manual (2nd ed. 1989)

F. Eckstein (ed.) Oligonucleotides and Analogues, 1st Ed. (Oxford University Press, New York, 1991).

Santoro, S. W.; Joyce, G. F. *Proc. Natl. Acad. Sci. U. S. A.* 1997, 94, 4262-4266.

Santoro, S. W., Joyce, G. F., Sakthivel, K., Gramatikova, S. & Barbas, C. F., III RNA Cleavage by a DNA Enzyme with Extended Chemical Functionality. *J. Am. Chem. Soc.* 122, 2433-2439 (2000).

Seeman et al., (1993) New J. Chem., 17, 739-755.

Shaiu et al., (1993) Nuc. Acids Res., 21, 99.

Shaw & Wang, (1993) Science, 260, 533-536.

Shekhtman et al., (1993) New J. Chem., 17, 757-763.

Smith and Feigon, Nature, (1992) 356, 164-168.

Soriaga and Hubbard, (1982) J. Am. Chem. Soc., 104, 3937.

Tang and Breaker, *Proc. Natl. Acad. Sci. USA,* 97, 5784-5789 (2000).

Tarasow, T. M.; Tarasow, S. L.; Eaton, B. E. *Nature* 1997, 389, 54-57.

Timmons and Zisman, (1965) J. Phys. Chem., 69, 984-990.

Tsang, J.; Joyce, G. F. *Methods Enzymol.* 1996, 267, 410-426.

Tuerk, C.; Gold, L. *Science* 1990, 249, 505-510.

Uphoff, K. W.; Bell, S. D.; Ellington, A. D. *Curr. Opin. Struct. Biol.* 1996, 6, 281-288.

Vaish, N. K.; Heaton, P. A.; Fedorova, O.; Eckstein, F. *Proc. Natl. Acad. Sci. U. S. A.* 1998, 95, 2158-2162.

Walkup, G. K. & Imperiali, B. Design and Evaluation of a Peptidyl Fluorescent Chemosensor for Divalent Zinc. *J. Am. Chem. Soc.* 118, 3053-3054 (1996).

Wang et al., Biochem., (1993) 32, 1899-1904.

Wang et al., (1991) Biochem., 30, 5667-5674.

Wecker, M.; Smith, D.; Gold, L. *RNA* 1996, 2, 982-994.

Wells, J. Biol. (1988) Chem., 263, 1095-1098.

Whitesides (1995) Proceedings of the Robert A. Welch Foundation 39th Conference On Chemical Research Nanophase Chemistry, Houston, Tex., pages 109-121.

Wiegand, T. W.; Janssen, R. C.; Eaton, B. E. *Chem. Biol.* 1997, 4, 675-683.

Wilson, C.; Szostak, J. W. *Nature* 1995, 374, 777-782.

Winkler, J. D., Bowen, C. M. & Michelet, V. Photodynamic Fluorescent Metal Ion Sensors with Parts per Billion Sensitivity. *J. Am. Chem. Soc.* 120, 3237-3242 (1998).

Zhang, B.; Cech, T. R. *Nature* 1997, 390, 96-100.

Zillmann, M.; Limauro, S. E.; Goodchild, J. *RNA* 1997, 3, 734-747.

The invention claimed is:

1. A method of detecting the presence of an ion in a sample, comprising:
   (a) forming a mixture comprising:
      (i) the sample; and
      (ii) an aggregate, wherein the aggregate comprises a plurality of complexes,
      wherein each complex comprises
         (I) a nucleic acid enzyme;
         (II) particles;
         (III) a first oligonucleotide attached to a solid surface of the particles;
         (IV) a second oligonucleotide attached to the solid surface of the particles; and
         (V) a substrate for the nucleic acid enzyme, wherein the substrate hybridizes to the first oligonucleotide and the second oligonucleotide,
      wherein the nucleic acid enzyme depends on the ion to cause cleavage of the substrate and cleavage of the substrate followed by heating to 50° C. results in de-aggregation of the aggregate; and
   (b) detecting deaggregation of the aggregate.

2. The method of claim 1, wherein the ion is $AsO_4^{3-}$.

3. The method of claim 1, wherein the ion is selected from the group consisting of $K^+$, $Na^+$, $Li^+$, $Tl^+$, $NH4^+$, $Ag^+$, $Mg^{2+}$, $Ca^{2+}$, $Mn^{2+}$, $Co^{2+}$, $Ni^{2+}$, $Zn^{2+}$, $Cd^{2+}$, $Pb^{2+}$, $Hg^{2+}$, $Hg_2^{2+}$, $Pt^{2+}$, $Ra^{2+}$, $Ba^{2+}$, $UO_2^{2+}$, $Sr^{2+}$, $Co^{3+}$, $Cr^{3+}$, $Ln^{3+}$, $Ce^{4+}$, and $Cr^{6+}$.

4. The method of claim 1, wherein the ion comprises a member selected from the group consisting of K (I), Na(I), Li(I), Tl(I), Ag(I), Hg(I), Mg (II), Ca (II), Mn (II), Co(II), Ni (II), Zn (II), Cd (II), Pb(II), Hg (II), Pt (II), Ra (II), Ba (II), Sr (II), Co (III), Cr (III), Ln (III), Ce (IV), Cr (VI) and U (VI).

5. A sensor for detecting the presence of an ion in a sample, comprising:
(i) an aggregate, wherein the aggregate comprises a plurality of complexes,
wherein each complex comprises
(I) a nucleic acid enzyme;
(II) particles;
(III) a first oligonucleotide attached to a solid surface of the particles;
(IV) a second oligonucleotide attached to the solid surface of the particles; and
(V) a substrate for the nucleic acid enzyme, wherein the substrate hybridizes to the first oligonucleotide and the second oligonucleotide,
wherein the nucleic acid enzyme depends on the ion to cause cleavage of the substrate and cleavage of the substrate results in deaggregation of the aggregate.

6. The sensor of claim 5, wherein the particles are gold particles.

7. The sensor of claim 5, wherein the particles comprise at least two sets, wherein:
(a) a first oligonucleotide is linked to a first set of particles and a second oligonucleotide is linked to a second set of particles; and
(b) the base sequence of the first oligonucleotide is different from the base sequence of the second oligonucleotide.

* * * * *

SEQUENCE LISTING

<160> NUMBER OF SEQ ID NOS: 88

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence:
      Trans-cleaving deoxyribozyme 17E

<400> SEQUENCE: 1
catctcttct ccgagccggt cgaaatagtg agt                                    33

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 2
actcactata ggaagagatg                                                   20

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 3
gtgccaagct taccg                                                        15

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 4
ctgcagaatt ctaatacgac tcactatagg aagagatggc gac                         43

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Description of Combined DNA/RNA Molecule:
      Primer

<400> SEQUENCE: 5
gggacgaatt ctaatacgac tcactata                                          28

<210> SEQ ID NO 6
<211> LENGTH: 97
<212> TYPE: DNA
<213> ORGANISM: Artificial Sequence
<220> FEATURE:
<223> OTHER INFORMATION: Description of Artificial Sequence: Synthetic

```
            DNA Template
<220> FEATURE:
<221> NAME/KEY: modified_base
<222> LOCATION: (20)..(59)
<223> OTHER INFORMATION: variable nucleotide

<400> SEQUENCE: 6
gtgccaagct taccgtcacn nnnnnnnnnn nnnnnnnnnn nnnnnnnnnn nnnnnnnng      60 agatctcgcc atctcttcct atagtgagtc gtattag                              97

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Variant of
      deoxyribozyme named 17E1

<400> SEQUENCE: 7
catctctttt gtcagcgact cgaaatagtg agt                                  33

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      Zn-DNA
<220> FEATURE:
<221> NAME/KEY: modified_base
<222> LOCATION: (2)..(4)
<223> OTHER INFORMATION: variable base complementary and covariant to
      positions 8-10
<220> FEATURE:
<221> NAME/KEY: modified_base
<222> LOCATION: (8)..(10)
<223> OTHER INFORMATION: variable base complementary and covariant to
      positions 2-4

<400> SEQUENCE: 8
tnnnagcnnn tcgaaatagt                                                 20

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      Zn-DNA
<220> FEATURE:
<221> NAME/KEY: modified_base
<222> LOCATION: (2)..(4)
<223> OTHER INFORMATION: variable base complementary and covariant to
      positions 8-10
<220> FEATURE:
<221> NAME/KEY: modified_base
<222> LOCATION: (8)..(10)
<223> OTHER INFORMATION: variable base complementary and covariant to
      positions 2-4

<400> SEQUENCE: 9
tnnnagcnnn acgaa                                                      15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      Class II Co-DNA
```

<400> SEQUENCE: 10
acccaagaag gggtg                                                              15

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      Rh-17DDS

<400> SEQUENCE: 11
actcactata ggaagagatg                                                         20

<210> SEQ ID NO 12
<211> LENGTH: 97
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate
<220> FEATURE:
<221> NAME/KEY: modified_base
<222> LOCATION: (39)..(78)
<223> OTHER INFORMATION: variable nucleotide

<400> SEQUENCE: 12
ctaatacgac tcactatagg aagagatggc gacatctcnn nnnnnnnnn nnnnnnnnn               60 nnnnnnnnnn nnnnnnnngt gacggtaagc ttggcac                                     97

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 13
ctgcagaatt ctaatacgac tcactatagg aagagatggc gac                              43

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 14
atctcttttg tcagcgactc gaaatagtgt gttgaagcag ctctagtgac                       50

<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 15
agccatagtt ctaccagcgg ttcgaaatag tgaagtgttc gtgactatc                        49

-continued

```
<210> SEQ ID NO 16
<211> LENGTH: 49
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 16
ggccatagtt ctaccagcgg ttcgaaatag tgaaatgttc gtgactatc                    49

<210> SEQ ID NO 17
<211> LENGTH: 51
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 17
gccagattag ttctaccagc ggttcgaaat agtgaaatgt tcgtgactat c                 51

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 18
atctccaaag atgccagcat gctattctcc gagccggtcg aaatagtgac                   50

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 19
atctccaaag atgcctgcat gctattctcc gagccggtcg aaatagtgac                   50

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 20
atctcgtctc cgagccggtc gaaatagtca ggtgtttcta ttcgggtgac                   50

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 21
atcaccttct ccgagccggt cgaaatagta gttttagta tatctgtgac                    50
```

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 22
atctcaggtg ttggctgctc tcgcggtggc gagaggtagg gtgatgtgac            50

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 23
ggtaagcttg gcac                                                  14

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 24
ctgcagaatt ctaatacgac gcactatagg aagagatggc gac                  43

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 25
atctcttgta ttagctacac tgttagtgga tcgggtctaa tctcggtgac            50

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 26
gtctcttgta ttagctacac tgttagtgga tcgggtctaa tctcggtgac            50

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 27
atctcctgta ttagctacac tgttagtgga tcgggtctaa tctcggtgac            50

<210> SEQ ID NO 28

```
<211> LENGTH: 49
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 28
atctcttgta ttagctacac tgttagtggg aacgttatca ttcggtgac            49

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 29
atctcttgac ccaagaaggg gtgtcaatct aatccgtcaa ccatg                45

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 30
atctcttgac ccaagaaggg gtgtcaatca aatccgtcaa ccatg                45

<210> SEQ ID NO 31
<211> LENGTH: 54
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 31
atctcttgac ccaagaaggg gtgtcaatct aatccgtaca accatgacgg taag      54

<210> SEQ ID NO 32
<211> LENGTH: 52
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 32
atctcttgac ccaagaaggg gtgtcaatct aatccgtcaa ggatgcggta ag        52

<210> SEQ ID NO 33
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 33
atctcaggtg ttggctgctc ccgcggtggc gggaggtagg gtgatgtgac            50

<210> SEQ ID NO 34
<211> LENGTH: 50
```

```
<210> SEQ ID NO 34
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 34
atctcaggtg ttggcatctc ccgcggtggc gagaggtagg gtgatgtgac              50

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 35
atctcaggtg ttggctgctc tcgcggtggc gagaggtagg gtcatgtgac              50

<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 36
atctcgcagt cgaagcttca ctgttagtgc ggacgggtag acttcgtgac              50

<210> SEQ ID NO 37
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 37
atttcttctg aatcctcaat gttagtggac ctagtcgtag tcgatgtgac              50

<210> SEQ ID NO 38
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 38
atctcggagc cagttagcat aatcttctga atcctcaatg ttagtgtgac              50

<210> SEQ ID NO 39
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 39
atctcggtgt tggctggata gagccggtag gccctatcgt agggtgtgac              50

<210> SEQ ID NO 40
<211> LENGTH: 50
<212> TYPE: DNA
```

```
<213> ORGANISM: Artificial Sequence
<220> FEATURE:
<223> OTHER INFORMATION: Description of Artificial Sequence: Synthetic
      Co-DNA

<400> SEQUENCE: 40
gtctcttttg tccgcgactc gaaatagtgt gttgaagcag ctctagtgac            50

<210> SEQ ID NO 41
<211> LENGTH: 54
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 41
agccatagtt ctaccagcgg ttcgaaatag tgaagtgttc gtgactatcg gtaa       54

<210> SEQ ID NO 42
<211> LENGTH: 14
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 42
ggtaagcttg gcac                                                  14

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 43
ttttgtcagc gactcgaaat agtgtgttga agcagctcta                      40

<210> SEQ ID NO 44
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 44
ttttgtcagc gactcgaaat agtgtgttga agccgctcta                      40

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 45
ttttgtcagc gactcgaaat agtgtattgc agtagatcta                      40

<210> SEQ ID NO 46
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      Zn-DNA

<400> SEQUENCE: 46
ttttgtcagc gactcgaaat agtgtgttac agttgcccta                               40

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 47
ttttgtcagc gactcgaaat agagagtcga caccctctc                                40

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 48
ttttgtcagc gactcgaaat agttagttga accagctctc                               40

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 49
ttttgtcagc gactcgaaat agtgagtaag aggagctatc                               40

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 50
ttttgtcagc gactcgaaat agtgagggga aacagctctc                               40

<210> SEQ ID NO 51
<211> LENGTH: 39
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 51
ttttgtcagc gactcgaaat agttagttga acacctctc                                39

<210> SEQ ID NO 52
<211> LENGTH: 40
<212> TYPE: DNA
<213> ORGANISM: Artificial Sequence
<220> FEATURE:
```

-continued

```
<223> OTHER INFORMATION: Description of Artificial Sequence: Synthetic
      Zn-DNA

<400> SEQUENCE: 52
ttttgtcagc gactcgaaat attgagttga agcagatctc                               40

<210> SEQ ID NO 53
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 53
ttttgtcagc gacacgaaat agtgagttga ggcggcgctg                               40

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 54
tttttgcagc gacacgaaat agttagttga agaagctctt                               40

<210> SEQ ID NO 55
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 55
ttttgtcagc gactcgaaat agtcagttgt agcagctctt                               40

<210> SEQ ID NO 56
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 56
ttttgtcagc gactcgaaat agtgcgtaga accagctctc                               40

<210> SEQ ID NO 57
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 57
ttttgtcagc gacacgaaat agtgcggtgt atctgccctc                               40

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Synthetic
```

Zn-DNA

<400> SEQUENCE: 58
ttttgtcagc gacacgaaat agtgtgatgt agtagctctc            40

<210> SEQ ID NO 59
<211> LENGTH: 38
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 59
ttttgtcagc gacacgaaat agtgtgacga atcatctc               38

<210> SEQ ID NO 60
<211> LENGTH: 39
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 60
ttttgtcagc gacacgaaat agtgtgttta agcgctctc              39

<210> SEQ ID NO 61
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 61
ttttgtcagc gacacgaaat agtgtgttga agcacgtctc            40

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 62
ttttgtcagc gactcgaaat agtttgttga agcagctctc            40

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 63
ttttgtcagc gactcgaaat agtgtattac agcagctctc            40

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

```
<400> SEQUENCE: 64
ttttgtcagc gactcgaaat agtgtgttga aacagctatc                                40

<210> SEQ ID NO 65
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 65
ttgtgcatgc tactcgtaat tgtgtctcga agcagctctc                                40

<210> SEQ ID NO 66
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 66
gtcagtcagg tactcgaaaa atagtgttca agccgctgtc                                40

<210> SEQ ID NO 67
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 67
tttttgcagc gactcgaaag attgtgttga ggcggctatc                                40

<210> SEQ ID NO 68
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 68
ttctctcagc gactaaaaat agtgtgttga agcccctctc                                40

<210> SEQ ID NO 69
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 69
tattgtcagt gacccaaaat agtatgttga agcagctctg                                40

<210> SEQ ID NO 70
<211> LENGTH: 39
<212> TYPE: DNA
<213> ORGANISM: Artificial Sequence
<220> FEATURE:
<223> OTHER INFORMATION: Description of Artificial Sequence: Synthetic
      Zn-DNA
```

```
<400> SEQUENCE: 70
ttttgtcagc tactgaaata gtgttttgaa gaagtcctg                              39

<210> SEQ ID NO 71
<211> LENGTH: 15
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 71
tcactatagg aagag                                                       15

<210> SEQ ID NO 72
<211> LENGTH: 36
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 72
ctcttcagcg atccggaacg gcacccatgt tagtga                                36

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 73
tcactataag aagagatgg                                                   19

<210> SEQ ID NO 74
<211> LENGTH: 37
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 74
acacatctct gaagtagcgc cgccgtatag tgacgct                               37

<210> SEQ ID NO 75
<211> LENGTH: 17
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate
```

<400> SEQUENCE: 75
ggagagagau gggugcg                                                  17

<210> SEQ ID NO 76
<211> LENGTH: 31
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 76
cgcacccagg ctagctacaa cgactctctc c                                  31

<210> SEQ ID NO 77
<211> LENGTH: 17
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 77
aaguaacuag agaugga                                                  17

<210> SEQ ID NO 78
<211> LENGTH: 29
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 78
cgcaccctcc gagccggacg aagttactt                                     29

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 79
ctcactatag gaagagatg                                                19

<210> SEQ ID NO 80
<211> LENGTH: 41
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:

Synthetic chimeric substrate

<400> SEQUENCE: 80
catctcttaa cggggctgtg cggctaggaa gtaatagtga g         41

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 81
actcactata ggaagagatg         20

<210> SEQ ID NO 82
<211> LENGTH: 33
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 82
catctcttct ccgagccggt cgaaatagtg agt         33

<210> SEQ ID NO 83
<211> LENGTH: 107
<212> TYPE: DNA
<213> ORGANISM: Artificial Sequence
<220> FEATURE:
<223> OTHER INFORMATION: Description of Artificial Sequence: Predicted
      secondary structure of the G3 deoxyribozyme
<220> FEATURE:
<221> NAME/KEY: modified_base
<222> LOCATION: (67)
<223> OTHER INFORMATION: variable nucleotide
<220> FEATURE:
<221> NAME/KEY: modified_base
<222> LOCATION: (69)..(74)
<223> OTHER INFORMATION: variable nucleotide
<220> FEATURE:
<221> NAME/KEY: modified_base
<222> LOCATION: (80)..(82)
<223> OTHER INFORMATION: variable nucleotide
<220> FEATURE:
<221> NAME/KEY: modified_base
<222> LOCATION: (85)..(89)
<223> OTHER INFORMATION: variable nucleotide

<400> SEQUENCE: 83
gggacgaatt ctaatacgac tcactatagg aagagatggc gacaactctt tacccaagaa         60
ggggtgngnn nnnngctacn nnatnnnnnt gacggtagct tggcacc         107

<210> SEQ ID NO 84
<211> LENGTH: 45
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 84

```
cactatagga agagatggcg acatctcttg acccaagaag gggtg                    45

<210> SEQ ID NO 85
<211> LENGTH: 44
<212> TYPE: DNA
<213> ORGANISM: Artificial Sequence
<220> FEATURE:
<223> OTHER INFORMATION: Description of Artificial Sequence: Synthetic
      chimeric oligonucleotide
<220> FEATURE:
<223> OTHER INFORMATION: Description of Combined DNA/RNA Molecule:
      Synthetic chimeric oligonucleotide

<400> SEQUENCE: 85
tgtcaactcg tgactcacta taggaagaga tgtgtcaact cgtg                    44

<210> SEQ ID NO 86
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 86
cacgagttga ca                                                        12

<210> SEQ ID NO 87
<211> LENGTH: 33
<212> TYPE: DNA
<213> ORGANISM: Artificial Sequence
<220> FEATURE:
<223> OTHER INFORMATION: Description of Artificial Sequence: Inactive
      deoxyribozyme 17E-C

<400> SEQUENCE: 87
catctcttcc ccgagccggt cgaaatagtg agt                                 33

<210> SEQ ID NO 88
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 88
cacgagttga ca                                                        12
```